(12) United States Patent
Smith et al.

(10) Patent No.: US 10,752,670 B2
(45) Date of Patent: Aug. 25, 2020

(54) ANTI-GD3 SPECIFIC CHIMERIC ANTIGEN RECEPTORS FOR CANCER IMMUNOTHERAPY

(71) Applicant: Cellectis, Paris (FR)

(72) Inventors: Julianne Smith, New York, NY (US); Cècile Schiffer-Mannioui, Villiers-sur-Marne (FR)

(73) Assignee: CELLECTIS, Paris (FR)

( * ) Notice: Subject to any disclaimer, the term of this patent is extended or adjusted under 35 U.S.C. 154(b) by 233 days.

(21) Appl. No.: 15/575,707

(22) PCT Filed: May 20, 2016

(86) PCT No.: PCT/EP2016/061485
§ 371 (c)(1),
(2) Date: Nov. 20, 2017

(87) PCT Pub. No.: WO2016/185035
PCT Pub. Date: Nov. 24, 2016

(65) Prior Publication Data
US 2018/0291079 A1    Oct. 11, 2018

(30) Foreign Application Priority Data

May 20, 2015 (DK) .................. 2015 70296

(51) Int. Cl.
| | |
|---|---|
| C07K 14/725 | (2006.01) |
| A61K 39/00 | (2006.01) |
| C07K 14/705 | (2006.01) |
| C07K 14/735 | (2006.01) |
| C07K 16/30 | (2006.01) |
| C12N 5/0783 | (2010.01) |
| A61K 38/00 | (2006.01) |

(52) U.S. Cl.
CPC .... *C07K 14/7051* (2013.01); *C07K 14/70517* (2013.01); *C07K 14/70535* (2013.01); *C07K 14/70575* (2013.01); *C07K 16/3084* (2013.01); *C12N 5/0636* (2013.01); *A61K 38/00* (2013.01); *A61K 2039/5158* (2013.01); *C07K 2317/53* (2013.01); *C07K 2317/56* (2013.01); *C07K 2317/565* (2013.01); *C07K 2317/622* (2013.01); *C07K 2319/00* (2013.01); *C07K 2319/02* (2013.01); *C07K 2319/03* (2013.01); *C07K 2319/30* (2013.01); *C07K 2319/33* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 5,037,743 A | 8/1991 | Welch et al. |
| 5,143,830 A | 9/1992 | Holland et al. |
| 5,225,539 A | 7/1993 | Winter |
| 5,530,101 A | 6/1996 | Queen et al. |
| 5,585,089 A | 12/1996 | Queen et al. |
| 5,766,886 A | 6/1998 | Studnicka et al. |
| 5,858,358 A | 1/1999 | June et al. |
| 5,883,223 A | 3/1999 | Gray |
| 6,010,613 A | 1/2000 | Walters et al. |
| 6,352,694 B1 | 3/2002 | June et al. |
| 6,407,213 B1 | 6/2002 | Carter et al. |
| 6,534,055 B1 | 3/2003 | June et al. |
| 6,692,964 B1 | 2/2004 | June et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,067,318 B2 | 6/2006 | June et al. |
| 7,144,575 B2 | 12/2006 | June et al. |
| 7,172,869 B2 | 2/2007 | June et al. |
| 7,175,843 B2 | 2/2007 | June et al. |
| 7,232,566 B2 | 6/2007 | June et al. |
| 2002/0132983 A1* | 9/2002 | Junghans .............. C07K 16/30 530/350 |
| 2003/0105000 A1 | 6/2003 | Pero et al. |
| 2005/0042664 A1 | 2/2005 | Wu et al. |

(Continued)

FOREIGN PATENT DOCUMENTS

| | | |
|---|---|---|
| EP | 0239400 | 8/1994 |
| EP | 0592106 | 11/2004 |

(Continued)

OTHER PUBLICATIONS

Lloyd et al (Protein Engineering, Design & Selection, 22:159-168, 2009).*
Edwards et al (J Mol Biol, 14;334(1):103-118, 2003).*
Arimondo et al., "Exploring the cellular activity of camptothecin-triple-helix-fonning oligonucleotide conjugates," Mol. Cell Biol., 26(1):324-33, Jan. 2006.
Atkins et al.,"A case for "StopGo": reprogramming translation to augment codon meaning of GGN by promoting unconventional termination (Stop) after addition of glycine and then allowing continued translation (Go)," Rna., 13(6):803-10, Jun. 2007.

(Continued)

*Primary Examiner* — Brad Duffy
(74) *Attorney, Agent, or Firm* — Fish & Richardson P.C.

(57) ABSTRACT

The present invention relates to Chimeric Antigen Receptors (CAR) that are recombinant chimeric proteins able to redirect immune cell specificity and reactivity toward selected membrane antigens, and more particularly in which extracellular ligand binding is a scFV derived from a GD3 monoclonal antibody, conferring specific immunity against GD3 positive cells. The engineered immune cells endowed with such CARs are particularly suited for treating solid tumors such as melanomas, carcinomas or liquid tumor such as T-cell lymphoblastic leukemia.

12 Claims, 22 Drawing Sheets

Specification includes a Sequence Listing.

(56) References Cited

U.S. PATENT DOCUMENTS

| | | | |
|---|---|---|---|
| 2005/0048617 | A1 | 3/2005 | Wu et al. |
| 2006/0121005 | A1 | 6/2006 | Berenson et al. |
| 2007/0231333 | A1 | 10/2007 | Boghaert et al. |
| 2013/0280221 | A1 | 10/2013 | Schonfeld et al. |
| 2013/0287748 | A1 | 10/2013 | June et al. |
| 2014/0234348 | A1 | 8/2014 | Scholler et al. |
| 2015/0038684 | A1* | 2/2015 | Jensen ............... A61K 47/6849 530/391.9 |
| 2017/0283497 | A1 | 10/2017 | Schiffer-Mannioui |

FOREIGN PATENT DOCUMENTS

| | | |
|---|---|---|
| EP | 519596 | 2/2005 |
| JP | 2014/510108 | 4/2014 |
| WO | WO 91/09967 | 7/1991 |
| WO | WO 93/17105 | 9/1993 |
| WO | WO 2004/083379 | 9/2004 |
| WO | WO 2012/012695 | 1/2012 |
| WO | WO 2012/097313 | 7/2012 |
| WO | WO 2012/138927 | 10/2012 |
| WO | WO 2013/033626 | 3/2013 |
| WO | WO 2013/063419 | 5/2013 |
| WO | WO 2013/123061 | 8/2013 |
| WO | WO 2013/176915 | 11/2013 |
| WO | WO 2014/031174 | 2/2014 |
| WO | WO 2014/031687 | 2/2014 |
| WO | WO 2014/039523 | 3/2014 |

OTHER PUBLICATIONS

Baskar et al., "Unique cell surface expression of receptor tyrosine kinase ROR1 in human B-cell chronic lymphocytic leukemia," Clin. Cancer Res. Off. J. Am. Assoc. Cancer Res., 14(2):396-404, Jan. 2008.
Bicocca et al., "Crosstalk between ROR1 and the Pre-B cell receptor promotes survival of t (1; 19) acute lymphoblastic leukemia," Cancer Cell, 22(5):656-667, Nov. 2012.
Bierer et al., "Cyclosporin A and FK506: molecular mechanisms of immunosuppression and probes for transplantation biology," Curr. Opin. Immunol., 5(5):763-73, Oct. 1993.
Birkle et al., "Role of tumor-associated gangliosides in cancer progression," Biochimie., 85(3-4):455-463, Mar.-Apr. 2003.
Boch et al., "Breaking the code of DNA binding specificity of TAL-type III effectors," Science, 326(5959):1509-12, Dec. 2009.
Carsberg et al., "Metastasis-associated 5T4 oncofoetal antigen is concentrated at microvillus projections of the plasma membrane," J. Cell Sci., 108(8):2905-16, Aug. 1995.
Castro et al., "5T4 oncofetal antigen is expressed in high risk of relapse childhood pre-B acute lymphoblastic leukemia and is associated with a more invasive and chemotactic phenotype," Leukemia., 26(7):1487-98, Jul. 2012.
Choudhury et al., "Silencing of ROR1 and FMOD with siRNA results in apoptosis of CLL cells," Br. J. Haematol., 151(4):327-335, Nov. 2010.
Choulika et al., "Induction of homologous recombination in mammalian chromosomes by using the I-SceI system of *Saccharomyces cerevisiae*," Mol. Cell. Biol., 15(4):1968-73, Apr. 1995.
Christian et al., "Targeting DNA double-strand breaks with TAL effector nucleases," Genetics, 186(2):757-61, Oct. 2010.
Cong et al., "Multiplex genome engineering using CRISPR/Cas systems," Science, 339(6121):819-23, Feb. 2013.
Cooper, "L. Innovative T Cell-Targeted Therapy for Ovarian Cancer," Annual Report 2012 prepared for US Army medical research and Medical Command.
Cros et al., "Problems related to resistance to cytarabine in acute myeloid leukemia," Leukemia & Lymphoma, 45(6):1123-1132, Jun. 2004.
Daneshmanesh et al., "Ror1, a cell surface receptor tyrosine kinase is expressed in chronic lymphocytic leukemia and may serve as a putative target for therapy," Int. J. Cancer, 123(5):1190-5, Sep. 2008.

Daniotti et al., "Cloning, characterization and developmental expression of alpha2,8 sialyltransferase (GD3 synthase, ST8Sia I) gene in chick brain and retina," Int. J. Dev. Neurosci., 15(6):767-776, Oct. 1997.
Dave et al., "Restricted cell surface expression of receptor tyrosine kinase ROR1 in pediatric B-lineage acute lymphoblastic leukemia suggests targetability with therapeutic monoclonal antibodies," PLoS One., 7(12):e52655, Dec. 2012.
Deltcheva et al., "CRISPR RNA maturation by trans-encoded small RNA and host factor RNase III," Nature, 471(7340):602-7, Mar. 2011.
Donelly et al., "The cleavage activities of aphthovirus and cardiovirus 2A proteins," J. Gen. Virol., 78:13-21, Jan. 1997.
Donnelly and Elliott, "Nuclear localization and shuttling of herpes simplex virus tegument protein VP13/14," J. Virol., 75(6):2566-74, Mar. 2001.
Donnelly et al., "Analysis of the aphthovirus 2A/2B polyprotein 'cleavage' mechanism indicates not a proteolytic reaction, but a novel translational effect: a putative ribosomal 'skip'," J. Gen. Virol., 82:1013-1025, May 2001.
Doronina et al., "Site-specific release of nascent chains from ribosomes at a sense codon," Mol. Cell Biol., 28(13):4227-39, Jul. 2008.
Dotti et al., "Redirecting T-cell specificity by introducing a tumor-specific chimeric antigen receptor," Blood., 116(7):1035-1044, Aug. 2010.
Eisenschmidt et al., "Developing a programmed restriction endonuclease for highly specific DNA cleavage." Nucleic. Acids. Res., 33(22):7039-47, Jan. 2005.
Fukuda et al., "Antisera induced by infusions of autologous Ad-CD154-leukemia B cells identify ROR1 as an oncofetal antigen and receptor for Wnt5a," Proc. Natl. Acad. Sci. U.S.A., 105(8):3047-3052, Feb. 2008.
Gardin et al., "Postremission treatment of elderly patients with acute myeloid leukemia in first complete remission after intensive induction chemotherapy: results of the multicenter randomized Acute Leukemia French Association (ALFA) 9803 trial," Blood., 109(12):5129-5135, Jun. 2007.
Garneau et al., "The CRISPR/Cas bacterial immune system cleaves bacteriophage and plasmid DNA," Nature, 468(7320):67-71, Nov. 2010.
Gasiunas et al., "Cas9-crRNA ribonucleoprotein complex mediates specific DNA cleavage for adaptive immunity in bacteria," Proc. Natl. Acad. Sci. U.S.A., 109(39):E2579-86, Sep. 2012.
GenBank Association No. AAA53133.1, "4-1BB [*Homo sapiens*]," Nov. 27, 1994, 2 pages.
GenBank Association No. NP001139345.1, "T-cell surface glycoprotein CD8 alpha chain isoform 1 precursor [*Homo sapiens*]," Mar. 15, 2015, 3 pages.
GenBank Association No. NP001992.1, "high affinity immunoglobulin epsilon receptor subunit alpha precursor [*Homo sapiens*]," Jan. 15, 2016, 3 pages.
GenBank Association No. NP006130.1, "T-cell-specific surface glycoprotein CD28 isoform 1 precursor [*Homo sapiens*]," Mar. 15, 2015, 3 pages.
Gentile et al., "Ror1 is a pseudokinase that is crucial for Met-driven tumorigenesis," Cancer Res., 71(8):3132-3141, Apr. 2011.
Gravotta et al., "In vivo and in vitro expression of gangliosides in chick retina Müeller cells," J. Neurochem., 52(3):768-776, Mar. 1989.
Guest et al., "The role of extracellular spacer regions in the optimal design of chimeric immune receptors: evaluation of four different scFvs and antigens," J. Immunother., 28(3):203-211, May 2005.
Haraguchi et al., "Isolation of GD3 synthase gene by expression cloning of GM3 alpha-2,8-sialyltransferase cDNA using anti-GD2 monoclonal antibody," Proc. Natl. Acad. Sco. U.S.A., 91(22):10455-10459, Oct. 1994.
Haynes et al., "Redirecting mouse CTL against colon carcinoma: superior signaling efficacy of single-chain variable domain chimeras containing TCR-zeta vs Fc epsilon RI-gamma," J. of Immunol., 166(1):182-187, Jan. 2001.

(56) References Cited

OTHER PUBLICATIONS

Henderson et al., "Comparison of the effects of FK-506, cyclosporin A and rapamycin on IL-2 production," Immunology, 73(3):316-21, Jul. 1991.
Hole and Stern., "A 72 kD trophoblast glycoprotein defined by a monoclonal antibody," Br. J. Cancer, 57(3):239-246, Mar. 1988.
Hudecek et al., "Receptor affinity and extracellular domain modifications affect tumor recognition by ROR1-specific chimeric antigen receptor T cells," Clin Canc Res., 19(12):3153-3164, Apr. 25, 2013.
International Search Report and Written Opinion issued in PCT/EP2015/067444, dated Oct. 19, 2015.
Jena et al., "Redirecting T-cell specificity by introducing a tumor-specific chimeric antigen receptor," Blood, 116(7):1035-44, Aug. 2010.
Jinek et al., "A programmable dual-RNA—guided DNA endonuclease in adaptive bacterial immunity," Science, 337(6096):816-21, Jun. 2012.
Jun. et al., "T cells with chimeric antigen receptors have potent antitumor effects and can establish memory in patients with advanced leukemia," Sci. Transl. Med., 3(95):95ra73, Aug. 2011.
Kalish and Glazer, "Targeted genome modification via triple helix formation," Ann. N.Y. Acad. Sci., 1058(1):151-61, Nov. 2005.
Klein et al., "Gene expression profiling of B cell chronic lymphocytic leukemia reveals a homogeneous phenotype related to memory B cells," J. Exp. Med., 194:1625-1638, Dec. 2001.
Li et al., "TAL nucleases (TALNs): hybrid proteins composed of TAL effectors and FokI DNA-cleavage domain," Nucleic. Acids. Res., 39(1):359-72, Jan. 2011.
Liu et al., "Calcineurin is a common target of cyclophilin-cyclosporin A and FKBP-FK506 complexes," Cell, 66(4):807-815, Aug. 1991.
Liu et al., "Inhibition of T cell signaling by immunophilin-ligand complexes correlates with loss of calcineurin phosphatase activity," Biochemistry., 31(16):3896-901, Apr. 1992.
Lo et al., "Anti-GD3 chimeric sFv-CD28/T-cell receptor zeta designer T cells for treatment of metastatic melanoma and other neuroectodermal tumors," Clin. Cancer Res., 16(10):2769-2780, May 2010.
Mali et al., "RNA-guided human genome engineering via Cas9," Science, 339(6121):823-6, Feb. 2013.
Mannioui et al., "Treatment of B cells malignancies with anti-CD19 CAR+, TCR-, CD52-allogeneic T cells," J ImmunoTherapy Canc., BioMed Central Ltd, London UK, 1(Suppl 1):P34, Nov. 7, 2013.
Matsuda et al., "Expression of the receptor tyrosine kinase genes, Ror1 and Ror2, during mouse development," Mech. Dev., 105(1-2):153-156, Jul. 2001.
Moscou and Bogdanove, "A simple cipher governs DNA recognition by TAL effectors," Science, 326(5959):1501, Dec. 2009.
Nakayama et al., "Expression cloning of a human GT3 synthase. GD3 and GT3 are synthesized by a single enzyme," J. Biol. Chem., 271(7):3684-91, Feb. 1996.
Padlan, "A possible procedure for reducing the immunogenicity of antibody variable domains while preserving their ligand-binding properties," Mol. Immunol., 28(4-5):489-498, Apr.-May 1991.
Paques and Duchateau, "Meganucleases and DNA double-strand break-induced recombination: perspectives for gene therapy," Curr. Gene Ther., 7(1):49-66, Feb. 2007.
Park et al., "Treating cancer with genetically engineered T cells," Trends Biotechnol., 29(11):550-7, Nov. 2011.
Peipp et al., "Efficient eukaryotic expression of fluorescent scFv fusion proteins directed against CD antigens for FACS applications," J. Immunol. Methods, 285(2):265-80, Feb. 2004.
Perrin et al., "Asymmetrical recognition and activity of the I-SceI endonuclease on its site and on intron-exon junctions," Embo. J., 12(7):2939-47, Jul. 1993.
Pingoud and Silva, "Precision genome surgery," Nat. Biotechnol., 25(7):743-4, Jul. 2007.
Poirot et al., "521 multiplex genome editing of TCR a/CD52 Genes as a platform for "Off the Shelf" Adoptive T-cell immunotherapies," 17th Annual Meeting of the American-Sciety-of-Gene-and-Cell-Therapy (ASGCT), 22(Suppl. 1):S201-S202, May 1, 2014, Washington DC., USA.
Poirot et al., "T-Cell engineering for "off-the-shelf" Adoptive Immunotherapy," Blood., 122(21):1661, Nov. 15, 2013.
Porter et al., "Chimeric antigen receptor-modified T cells in chronic lymphoid leukemia," N. Engl. J. Med., 365(8):725-733, Aug. 2011.
Porteus and Carroll, "Gene targeting using zinc finger nucleases," Nat. Biotechnol., 23(8):967-73, Aug. 2005.
Reaman et al., "Anti-GD3 monoclonal antibody analysis of childhood T-cell acute lymphoblastic leukemia: detection of a target antigen for antibody-mediated cytolysis," Cancer Res., 50(1):202-205, Jan. 1990.
Reddy et al., "Localization of the human Ror1 gene (NTRKR1) to chromosome 1p31-p32 by fluorescence in situ hybridization and somatic cell hybrid analysis," Genomics, 41(2):238-5, Apr. 1997.
Rosenwald et al., "Relation of gene expression phenotype to immunoglobulin mutation genotype in B cell chronic lymphocytic leukemia," J. Exp. Med., 194(11):1639-1647, Dec. 2001.
Rouet et al., "Introduction of double-strand breaks into the genome of mouse cells by expression of a rare-cutting endonuclease," Mol. Cell Biol., 14(12):8096-106, Dec. 1994.
Sorek et al., "CRISPR-mediated adaptive immune systems in bacteria and archaea," Annu. Rev. Biochem., Jun. 2013.
Starzynska et al., "5T4 oncofetal antigen in gastric carcinoma and its clinical significance," Eur. J. Gatrerol Heptol., 10(6):479-84, Jun. 1998.
Stoddard, "Homing endonuclease structure and function," Q. Rev. Biophys., 38(1):49-95, Feb. 2005.
Studincka et al., "Human-engineered monoclonal antibodies retain full specific binding activity by preserving non-CDR complementarity-modulating residues," Protein Eng., 7(6):805-814, Jun. 1994.
Yamaguchi et al., "NKX2-1/TITF1/TTF-1-Induced ROR1 is required to sustain EGFR survival signaling in lung adenocarcinoma," Cancer Cell, 21(3):348-361, Mar. 2012.
Yun et al., "Targeting of T lymphocytes to melanoma cells through chimeric anti-GD3 immunoglobulin T-cell receptors," Neoplasia., 2(5):449-459, Sep.-Oct. 2000.
Zhang et al., "ROR1 is expressed in human breast cancer and associated with enhanced tumor-cell growth," PLoS One, 7(3):e31127, Mar. 2012.
Zhang et al., "The onco-embryonic antigen ROR1 is expressed by a variety of human cancers," Am. J. Pathol., 181(6):1903-1910, Dec. 2012.
Almagro and Fransson, "Humanization of antibodiesHumanization of antibodies," Frontiers in Bioscience, 13: 1619-33, Jan. 2008.
Banihashenni et al., "Development of specific nanobodies (VHH) for CD19 immuno-targeting of human B-lymphocytes," Iran. J. Basic. Med. Sci., 21(5):455-464, May 2018.
Burgess et al., "Possible dissociation of the heparin-binding and mitogenic activities of heparin-binding (acidic fibroblast) growth factor-1 from its receptor-binding activities by site-directed mutagenesis of a single lysine residue" J. of Cell. Biol., 111(5 Pt 1):2129-2138, Nov. 1990.
Coleman et al., "Effects of amino acid sequence changes on antibody-antigen interactions," Res. Immunol., 145(1):33-36, Jan. 1994.
Ibraginnova and Wade, "Stability of the beta-sheet of the WW domain: A molecular dynamics simulation study," Biophys. J., 77(4):2191-2198, Oct. 1999.
Rudikoff et al., "Single amino acid substitution altering antigen-binding specificity," Proc. Natl. Acad. Sci. U.S.A., 79(6):1979-1983, Mar. 1982.
Mariuzza et al., "The structural basis of antigen-antibody recognition," Annu. Rev. Biophys. Biophys. Chem., 16(1):139-159, Jun. 1987.

* cited by examiner

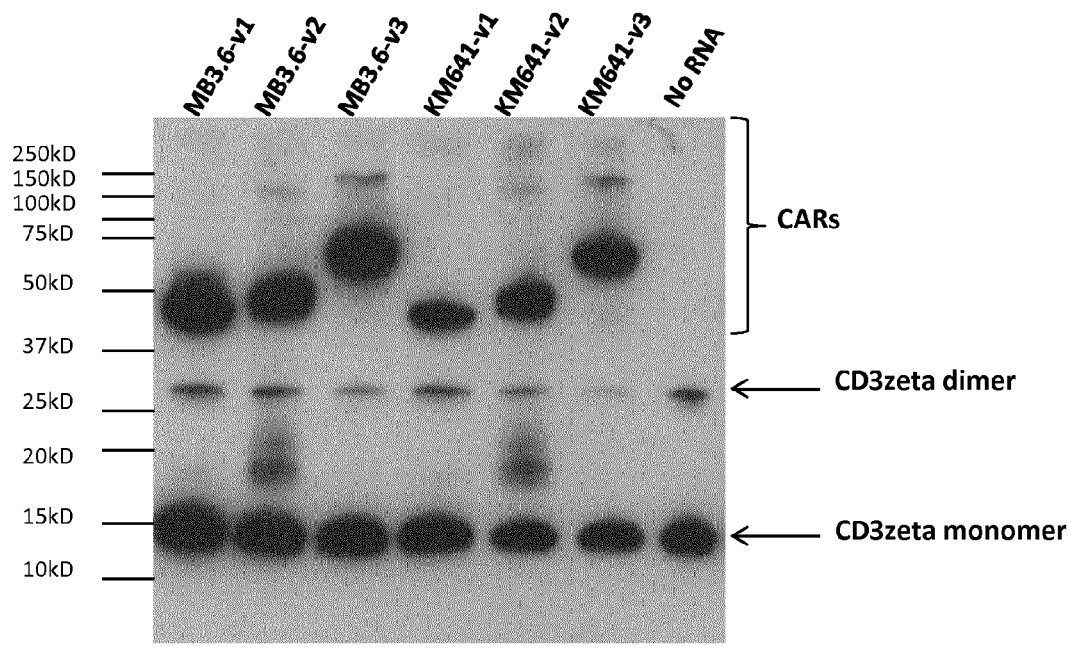
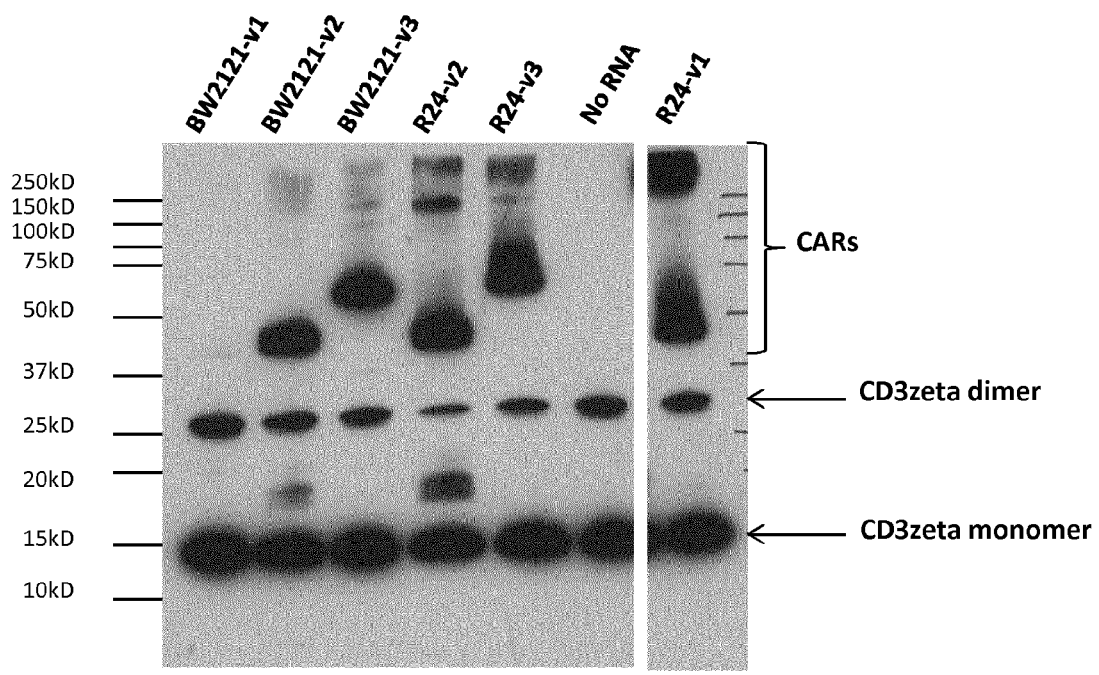
Figure 6

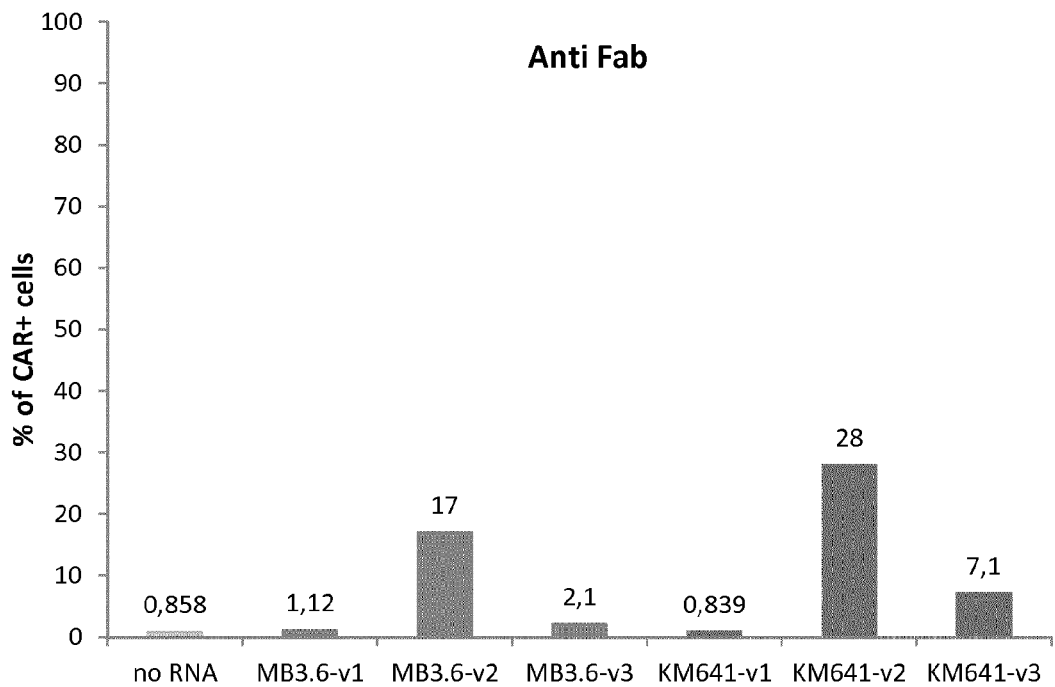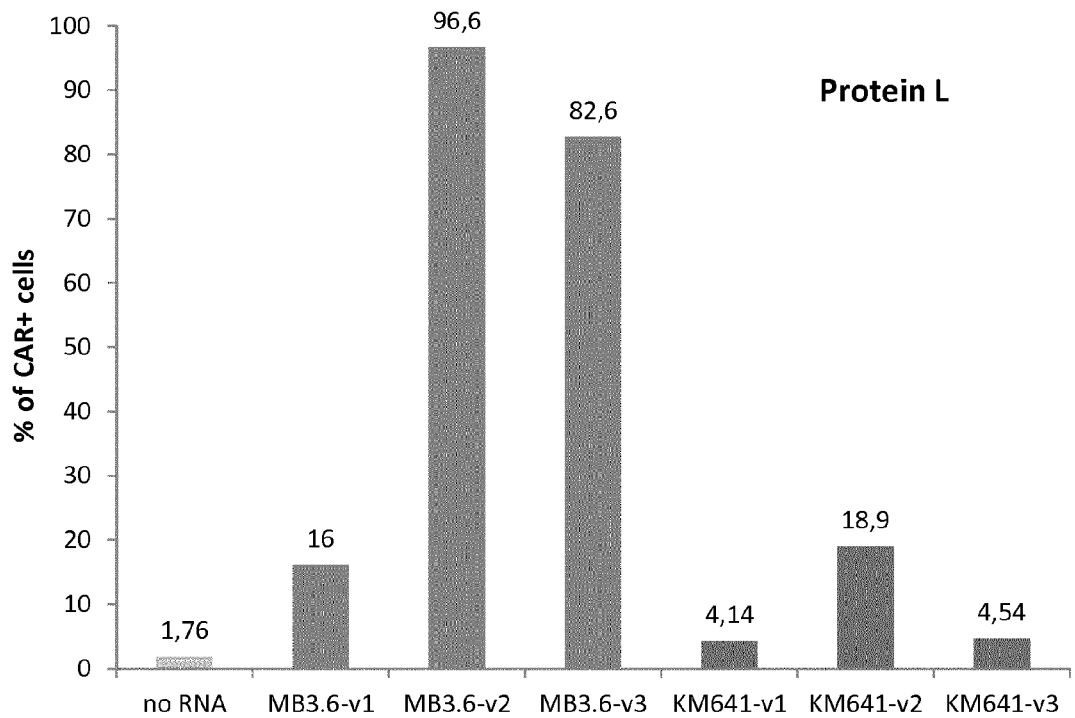
Figure 7A

Sequences alignment

```
                        CDR-H1                                    CDR-H2
R24_VH            D[V]QLVESGGGLVQPGGSRKLSCAASGFTFSNFGMHWVRQAPEKGLEWVA]YISSGGSSINY
IGHV3-NL1*01      QVQLVESGGGVVQPGGSLRLSCAASGFTFSSYGMHWVRQAPGKGLEWVSVIYSGGSSTYY
AA Differences     *                                        **      **        *
More critical AA                                                    **        *
Less critical AA   *

CDR-H3
R24_VH            ADTVKGR[F][T]S[R]D[N]PKNT[L]FLQMTSLRSEDTAIYYCTRGGTGTRSLYYFDYWGQGATLIV
IGHV3-NL1*01      ADSVKGRFTISRDNSKNTLYLQMNSLRAEDTAVYYCAK
IGHJ4*01                                                            WGQGTLVTV
AA Differences      *                    *    *             *                ****
More critical AA                              *
Less critical AA    *                    *

[Vernier zone residues]

IMGT-CDR residues
```

Sequences alignment

```
                              CDR-L1                               CDR-L2
R24_VL        DIQMTQITSSLSVSLGDRVIISCRASQDIGNFLNWYQQKPDGSLKLLIYTSRLQSGVPS
IGKV1-33*01   DIQMTQSPSSLSASVGDRVTITCQASQDISNYLNWYQQKPGKAPKLLIYDASNLETGVPS
AA Differences     **    * *  *  **  ****          *                 ***
More Critical AA      *                                              *
Less critical AA   **

CDR-L3
R24_VH        RFSGWGSGTDYSLTISNLEEEDIATFFCQQGKTLPYTFGGGTKLEIK
IGKV1-33*01   RFSGSGSGTDFTFTISSLQPEDIATYYCQQYDNLP
IGKJ2*01                                    YTFGQGTKLEIK
AA Differences    * *** *   *** ***  **    *
More Critical AA    *              *
Less critical AA  *   *       **     *

IMGT-CDR residues          Vernier zone residues
```

Figure 20

SEQUENCE LISTING

```
<160> NUMBER OF SEQ ID NOS: 61

<210> SEQ ID NO 1
<211> LENGTH: 20
<212> TYPE: PRT
<213> ORGANISM: artificial sequence
<220> FEATURE:
<223> OTHER INFORMATION: signal peptide

<400> SEQUENCE: 1

Met Glu Thr Asp Thr Leu Leu Leu Trp Val Leu Leu Leu Trp Val Pro
1               5                   10                  15

Gly Ser Thr Gly
            20

<210> SEQ ID NO 2
<211> LENGTH: 21
<212> TYPE: PRT
<213> ORGANISM: artificial sequence
<220> FEATURE:
<223> OTHER INFORMATION: signal peptide

<400> SEQUENCE: 2

Met Ala Leu Pro Val Thr Ala Leu Leu Leu Pro Leu Ala Leu Leu Leu
1               5                   10                  15
```

-continued

His Ala Ala Arg Pro
            20

<210> SEQ ID NO 3
<211> LENGTH: 16
<212> TYPE: PRT
<213> ORGANISM: homo sapiens
<220> FEATURE:
<223> OTHER INFORMATION: FcgRIIIa hinge

<400> SEQUENCE: 3

Gly Leu Ala Val Ser Thr Ile Ser Ser Phe Phe Pro Gly Tyr Gln
1               5                   10                  15

<210> SEQ ID NO 4
<211> LENGTH: 45
<212> TYPE: PRT
<213> ORGANISM: homo sapiens
<220> FEATURE:
<223> OTHER INFORMATION: CD8alpha hinge

<400> SEQUENCE: 4

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 5
<211> LENGTH: 231
<212> TYPE: PRT
<213> ORGANISM: homo sapiens
<220> FEATURE:
<223> OTHER INFORMATION: IgG1 hinge

<400> SEQUENCE: 5

Glu Pro Lys Ser Pro Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ala Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

```
Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 6
<211> LENGTH: 24
<212> TYPE: PRT
<213> ORGANISM: homo sapiens
<220> FEATURE:
<223> OTHER INFORMATION: CD8alpha transmembrane domain

<400> SEQUENCE: 6

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 7
<211> LENGTH: 27
<212> TYPE: PRT
<213> ORGANISM: homo sapiens
<220> FEATURE:
<223> OTHER INFORMATION: 41BB transmembrane domain

<400> SEQUENCE: 7

Ile Ile Ser Phe Phe Leu Ala Leu Thr Ser Thr Ala Leu Leu Phe Leu
1               5                   10                  15

Leu Phe Phe Leu Thr Leu Arg Phe Ser Val Val
            20                  25

<210> SEQ ID NO 8
<211> LENGTH: 42
<212> TYPE: PRT
<213> ORGANISM: homo sapiens
<220> FEATURE:
<223> OTHER INFORMATION: Fragment of 4-1BB (residues 214-255)

<400> SEQUENCE: 8

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 9
<211> LENGTH: 112
<212> TYPE: PRT
<213> ORGANISM: homo sapiens
<220> FEATURE:
<223> OTHER INFORMATION: fragment of T-cell surface glycoprotein CD3
      zeta chain

<400> SEQUENCE: 9

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30
```

```
Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 10
<211> LENGTH: 15
<212> TYPE: PRT
<213> ORGANISM: artificial sequence
<220> FEATURE:
<223> OTHER INFORMATION: linker sequence

<400> SEQUENCE: 10

Gly Gly Gly Gly Ser Gly Gly Gly Gly Ser Gly Gly Gly Gly Ser
1               5                   10                  15

<210> SEQ ID NO 11
<211> LENGTH: 120
<212> TYPE: PRT
<213> ORGANISM: artificial sequence
<220> FEATURE:
<223> OTHER INFORMATION: R24 heavy chain variable region

<400> SEQUENCE: 11

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Asn Phe
            20                  25                  30

Gly Met His Trp Val Arg Gln Ala Pro Glu Lys Gly Leu Glu Trp Val
        35                  40                  45

Ala Tyr Ile Ser Ser Gly Ser Ser Ile Asn Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Ile Tyr Tyr Cys
                85                  90                  95

Thr Arg Gly Gly Thr Gly Thr Arg Ser Leu Tyr Tyr Phe Asp Tyr Trp
            100                 105                 110

Gly Gln Gly Ala Thr Leu Ile Val
        115                 120

<210> SEQ ID NO 12
<211> LENGTH: 107
<212> TYPE: PRT
<213> ORGANISM: artificial sequence
<220> FEATURE:
<223> OTHER INFORMATION: R24 light chain variable region

<400> SEQUENCE: 12

Asp Ile Gln Met Thr Gln Ile Thr Ser Ser Leu Ser Val Ser Leu Gly
1               5                   10                  15

Asp Arg Val Ile Ile Ser Cys Arg Ala Ser Gln Asp Ile Gly Asn Phe
            20                  25                  30
```

Leu Asn Trp Tyr Gln Gln Lys Pro Asp Gly Ser Leu Lys Leu Leu Ile
                35                  40                  45

Tyr Tyr Thr Ser Arg Leu Gln Ser Gly Val Pro Ser Arg Phe Ser Gly
 50                  55                  60

Trp Gly Ser Gly Thr Asp Tyr Ser Leu Thr Ile Ser Asn Leu Glu Glu
 65                  70                  75                  80

Glu Asp Ile Ala Thr Phe Phe Cys Gln Gln Gly Lys Thr Leu Pro Tyr
                 85                  90                  95

Thr Phe Gly Gly Gly Thr Lys Leu Glu Ile Lys
            100                 105

<210> SEQ ID NO 13
<211> LENGTH: 121
<212> TYPE: PRT
<213> ORGANISM: artificial sequence
<220> FEATURE:
<223> OTHER INFORMATION: MB3.6 heavy chain variable region

<400> SEQUENCE: 13

Glu Val Val Val Glu Ser Gly Gly Gly Phe Val Lys Pro Gly Gly
 1               5                  10                  15

Ser Leu Lys Leu Ser Cys Ala Ala Gly Phe Thr Phe Ser Arg Tyr
                20                  25                  30

Ala Met Ser Trp Val Arg Gln Thr Pro Glu Lys Arg Leu Glu Trp Val
            35                  40                  45

Ala Thr Ile Ser Ser Gly Gly Ser His Thr Tyr Tyr Pro Asp Ser Val
 50                  55                  60

Lys Gly Arg Phe Thr Ile Ser Arg Asp Asn Ala Lys Asn Thr Leu Tyr
 65                  70                  75                  80

Leu Gln Met Ser Ser Leu Arg Ser Glu Asp Thr Ala Ile Tyr Tyr Cys
                 85                  90                  95

Ala Arg Pro Gly Tyr Asp Arg Gly Ala Trp Phe Phe Asp Val Trp Gly
            100                 105                 110

Ala Gly Thr Thr Val Thr Val Ser Ser
            115                 120

<210> SEQ ID NO 14
<211> LENGTH: 108
<212> TYPE: PRT
<213> ORGANISM: artificial sequence
<220> FEATURE:
<223> OTHER INFORMATION: MB3.6 light chain variable region

<400> SEQUENCE: 14

Asp Ile Val Leu Thr Gln Ser Pro Ala Thr Leu Ser Val Thr Pro Gly
 1               5                  10                  15

Asp Ser Val Ser Leu Ser Cys Arg Ala Ser Gln Ile Ile Ser Asn Asn
                20                  25                  30

Leu His Trp Tyr Gln Gln Lys Ser His Glu Ser Pro Arg Leu Leu Ile
            35                  40                  45

Lys Tyr Ala Ser Gln Ser Ile Ser Gly Ile Pro Ser Arg Phe Ser Gly
 50                  55                  60

Ser Gly Ser Gly Thr Asp Phe Thr Leu Ser Ile Asn Ser Val Glu Thr
 65                  70                  75                  80

Glu Asp Phe Gly Met Tyr Phe Cys Gln Gln Ser Asn Ser Trp Pro Leu
                 85                  90                  95

Thr Phe Gly Ser Gly Thr Lys Leu Glu Ile Lys Arg
            100                 105

```
<210> SEQ ID NO 15
<211> LENGTH: 119
<212> TYPE: PRT
<213> ORGANISM: artificial sequence
<220> FEATURE:
<223> OTHER INFORMATION: KM641 heavy chain variable region

<400> SEQUENCE: 15

Glu Val Thr Leu Val Glu Ser Gly Gly Asp Phe Val Lys Pro Gly Gly
1               5                   10                  15

Ser Leu Lys Val Ser Cys Ala Ala Ser Gly Phe Ala Phe Ser His Tyr
                20                  25                  30

Ala Met Ser Trp Val Arg Gln Thr Pro Ala Lys Arg Leu Glu Trp Val
            35                  40                  45

Ala Tyr Ile Ser Ser Gly Gly Ser Gly Thr Tyr Tyr Ser Asp Ser Val
        50                  55                  60

Lys Gly Arg Phe Thr Ile Ser Arg Asp Asn Ala Lys Asn Thr Leu Tyr
65                  70                  75                  80

Leu Gln Met Arg Ser Leu Arg Ser Glu Asp Ser Ala Met Tyr Phe Cys
                85                  90                  95

Thr Arg Val Lys Leu Gly Thr Tyr Tyr Phe Asp Ser Trp Gly Gln Gly
                100                 105                 110

Thr Thr Leu Thr Val Ser Ser
            115

<210> SEQ ID NO 16
<211> LENGTH: 107
<212> TYPE: PRT
<213> ORGANISM: artificial sequence
<220> FEATURE:
<223> OTHER INFORMATION: KM641 light chain variable region

<400> SEQUENCE: 16

Asp Ile Gln Met Thr Gln Thr Ala Ser Ser Leu Pro Ala Ser Leu Gly
1               5                   10                  15

Asp Arg Val Thr Ile Ser Cys Ser Ala Ser Gln Asp Ile Ser Asn Tyr
                20                  25                  30

Leu Asn Trp Tyr Gln Gln Lys Pro Asp Gly Thr Val Lys Leu Leu Ile
            35                  40                  45

Phe Tyr Ser Ser Asn Leu His Ser Gly Val Pro Ser Arg Phe Ser Gly
        50                  55                  60

Gly Gly Ser Gly Thr Asp Tyr Ser Leu Thr Ile Ser Asn Leu Glu Pro
65                  70                  75                  80

Glu Asp Ile Ala Thr Tyr Phe Cys His Gln Tyr Ser Lys Leu Pro Trp
                85                  90                  95

Thr Phe Gly Gly Gly Thr Lys Leu Glu Ile Lys
                100                 105

<210> SEQ ID NO 17
<211> LENGTH: 118
<212> TYPE: PRT
<213> ORGANISM: artificial sequence
<220> FEATURE:
<223> OTHER INFORMATION: BW2121 heavy chain variable region

<400> SEQUENCE: 17

Gln Val Gln Leu Gln Gln Ser Gly Gly Gly Leu Val Lys Pro Gly Gly
1               5                   10                  15
```

```
Ser Leu Thr Leu Ser Cys Ala Ala Ser Arg Phe Thr Phe Ser Thr Tyr
            20                  25                  30

Ala Met Ser Trp Val Arg Gln Thr Pro Ala Lys Arg Leu Glu Trp Val
        35                  40                  45

Ala Tyr Ile Ser Ser Gly Gly Ala Ser Thr Tyr Tyr Arg Asp Ser Val
50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Gly Gly Ser Arg Tyr Ala Met Asp Tyr Trp Gly Gln Gly Thr
            100                 105                 110

Thr Val Thr Val Ser Ser
            115
```

```
<210> SEQ ID NO 18
<211> LENGTH: 106
<212> TYPE: PRT
<213> ORGANISM: artificial sequence
<220> FEATURE:
<223> OTHER INFORMATION: BW2121 light chain variable region

<400> SEQUENCE: 18

Asp Ile Gln Leu Thr Gln Ser Pro Ala Ile Leu Ser Val Ser Pro Gly
1               5                   10                  15

Glu Arg Val Ser Phe Ser Cys Trp Ala Ser Gln Ser Ile Gly Thr Ser
            20                  25                  30

Ile His Trp Tyr Gln Gln Arg Thr Asn Gly Ser Pro Arg Leu Leu Ile
        35                  40                  45

Lys Tyr Ser Ser Glu Ser Ile Ser Gly Ile Pro Ser Arg Phe Ser Gly
50                  55                  60

Ser Gly Ser Gly Thr Asp Phe Thr Leu Ser Ile Asn Ser Leu Glu Ser
65                  70                  75                  80

Glu Asp Ile Ala Asp Tyr Tyr Cys Gln Gln Thr Tyr Ser Trp Pro Phe
                85                  90                  95

Thr Phe Gly Ser Gly Thr Lys Leu Glu Ile
            100                 105
```

```
<210> SEQ ID NO 19
<211> LENGTH: 456
<212> TYPE: PRT
<213> ORGANISM: artificial sequence
<220> FEATURE:
<223> OTHER INFORMATION: R24(VH VL)-FcgRIIIahinge-CD8aTM-41BB.IC-CD3z.IC

<400> SEQUENCE: 19

Met Ala Leu Pro Val Thr Ala Leu Leu Leu Pro Leu Ala Leu Leu Leu
1               5                   10                  15

His Ala Ala Arg Pro Asp Val Gln Leu Val Glu Ser Gly Gly Gly Leu
            20                  25                  30

Val Gln Pro Gly Gly Ser Arg Lys Leu Ser Cys Ala Ala Ser Gly Phe
        35                  40                  45

Thr Phe Ser Asn Phe Gly Met His Trp Val Arg Gln Ala Pro Glu Lys
50                  55                  60

Gly Leu Glu Trp Val Ala Tyr Ile Ser Ser Gly Ser Ser Ile Asn
65                  70                  75                  80

Tyr Ala Asp Thr Val Lys Gly Arg Phe Thr Ile Ser Arg Asp Asn Pro
                85                  90                  95
```

Lys Asn Thr Leu Phe Leu Gln Met Thr Ser Leu Arg Ser Glu Asp Thr
            100                 105                 110

Ala Ile Tyr Tyr Cys Thr Arg Gly Gly Thr Gly Thr Arg Ser Leu Tyr
        115                 120                 125

Tyr Phe Asp Tyr Trp Gly Gln Gly Ala Thr Leu Ile Val Gly Gly Gly
    130                 135                 140

Gly Ser Gly Gly Gly Ser Gly Gly Gly Ser Asp Ile Gln Met
145                 150                 155                 160

Thr Gln Ile Thr Ser Ser Leu Ser Val Ser Leu Gly Asp Arg Val Ile
                165                 170                 175

Ile Ser Cys Arg Ala Ser Gln Asp Ile Gly Asn Phe Leu Asn Trp Tyr
            180                 185                 190

Gln Gln Lys Pro Asp Gly Ser Leu Lys Leu Leu Ile Tyr Tyr Thr Ser
        195                 200                 205

Arg Leu Gln Ser Gly Val Pro Ser Arg Phe Ser Gly Trp Gly Ser Gly
    210                 215                 220

Thr Asp Tyr Ser Leu Thr Ile Ser Asn Leu Glu Gln Glu Asp Ile Ala
225                 230                 235                 240

Thr Phe Phe Cys Gln Gln Gly Lys Thr Leu Pro Tyr Thr Phe Gly Gly
                245                 250                 255

Gly Thr Lys Leu Glu Ile Lys Gly Leu Ala Val Ser Thr Ile Ser Ser
            260                 265                 270

Phe Phe Pro Pro Gly Tyr Gln Ile Tyr Ile Trp Ala Pro Leu Ala Gly
        275                 280                 285

Thr Cys Gly Val Leu Leu Leu Ser Leu Val Ile Thr Leu Tyr Cys Lys
    290                 295                 300

Arg Gly Arg Lys Lys Leu Leu Tyr Ile Phe Lys Gln Pro Phe Met Arg
305                 310                 315                 320

Pro Val Gln Thr Thr Gln Glu Glu Asp Gly Cys Ser Cys Arg Phe Pro
                325                 330                 335

Glu Glu Glu Glu Gly Gly Cys Glu Leu Arg Val Lys Phe Ser Arg Ser
            340                 345                 350

Ala Asp Ala Pro Ala Tyr Gln Gln Gly Gln Asn Gln Leu Tyr Asn Glu
        355                 360                 365

Leu Asn Leu Gly Arg Arg Glu Glu Tyr Asp Val Leu Asp Lys Arg Arg
    370                 375                 380

Gly Arg Asp Pro Glu Met Gly Gly Lys Pro Arg Arg Lys Asn Pro Gln
385                 390                 395                 400

Glu Gly Leu Tyr Asn Glu Leu Gln Lys Asp Lys Met Ala Glu Ala Tyr
                405                 410                 415

Ser Glu Ile Gly Met Lys Gly Glu Arg Arg Arg Gly Lys Gly His Asp
            420                 425                 430

Gly Leu Tyr Gln Gly Leu Ser Thr Ala Thr Lys Asp Thr Tyr Asp Ala
        435                 440                 445

Leu His Met Gln Ala Leu Pro Pro
    450                 455

<210> SEQ ID NO 20
<211> LENGTH: 486
<212> TYPE: PRT
<213> ORGANISM: artificial sequence
<220> FEATURE:
<223> OTHER INFORMATION: R24(VH VL)-CD8ahinge-CD8aTM-41BB.IC-CD3z.IC

<400> SEQUENCE: 20

```
Met Ala Leu Pro Val Thr Ala Leu Leu Leu Pro Leu Ala Leu Leu Leu
1               5                   10                  15

His Ala Ala Arg Pro Asp Val Gln Leu Val Glu Ser Gly Gly Gly Leu
            20                  25                  30

Val Gln Pro Gly Gly Ser Arg Lys Leu Ser Cys Ala Ala Ser Gly Phe
        35                  40                  45

Thr Phe Ser Asn Phe Gly Met His Trp Val Arg Gln Ala Pro Glu Lys
    50                  55                  60

Gly Leu Glu Trp Val Ala Tyr Ile Ser Ser Gly Ser Ser Ile Asn
65                  70                  75                  80

Tyr Ala Asp Thr Val Lys Gly Arg Phe Thr Ile Ser Arg Asp Asn Pro
                85                  90                  95

Lys Asn Thr Leu Phe Leu Gln Met Thr Ser Leu Arg Ser Glu Asp Thr
            100                 105                 110

Ala Ile Tyr Tyr Cys Thr Arg Gly Gly Thr Gly Thr Arg Ser Leu Tyr
        115                 120                 125

Tyr Phe Asp Tyr Trp Gly Gln Gly Ala Thr Leu Ile Val Gly Gly Gly
    130                 135                 140

Gly Ser Gly Gly Gly Ser Gly Gly Gly Ser Asp Ile Gln Met
145                 150                 155                 160

Thr Gln Ile Thr Ser Ser Leu Ser Val Ser Leu Gly Asp Arg Val Ile
                165                 170                 175

Ile Ser Cys Arg Ala Ser Gln Asp Ile Gly Asn Phe Leu Asn Trp Tyr
        180                 185                 190

Gln Gln Lys Pro Asp Gly Ser Leu Lys Leu Leu Ile Tyr Tyr Thr Ser
        195                 200                 205

Arg Leu Gln Ser Gly Val Pro Ser Arg Phe Ser Gly Trp Gly Ser Gly
    210                 215                 220

Thr Asp Tyr Ser Leu Thr Ile Ser Asn Leu Glu Gln Glu Asp Ile Ala
225                 230                 235                 240

Thr Phe Phe Cys Gln Gln Gly Lys Thr Leu Pro Tyr Thr Phe Gly Gly
            245                 250                 255

Gly Thr Lys Leu Glu Ile Lys Thr Thr Thr Pro Ala Pro Arg Pro Pro
        260                 265                 270

Thr Pro Ala Pro Thr Ile Ala Ser Gln Pro Leu Ser Leu Arg Pro Glu
    275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
            325                 330                 335

Lys Lys Leu Leu Tyr Ile Phe Lys Gln Pro Phe Met Arg Pro Val Gln
        340                 345                 350

Thr Thr Gln Glu Glu Asp Gly Cys Ser Cys Arg Phe Pro Glu Glu Glu
    355                 360                 365

Glu Gly Gly Cys Glu Leu Arg Val Lys Phe Ser Arg Ser Ala Asp Ala
    370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415
```

-continued

```
Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
            435                 440                 445

Gly Met Lys Gly Glu Arg Arg Arg Gly Lys Gly His Asp Gly Leu Tyr
            450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 21
<211> LENGTH: 672
<212> TYPE: PRT
<213> ORGANISM: artificial sequence
<220> FEATURE:
<223> OTHER INFORMATION: R24(VH VL)-IgG1hinge- CD8aTM-41BB.IC-CD3z.IC

<400> SEQUENCE: 21

Met Ala Leu Pro Val Thr Ala Leu Leu Leu Pro Leu Ala Leu Leu Leu
1               5                   10                  15

His Ala Ala Arg Pro Asp Val Gln Leu Val Glu Ser Gly Gly Gly Leu
            20                  25                  30

Val Gln Pro Gly Gly Ser Arg Lys Leu Ser Cys Ala Ala Ser Gly Phe
        35                  40                  45

Thr Phe Ser Asn Phe Gly Met His Trp Val Arg Gln Ala Pro Glu Lys
    50                  55                  60

Gly Leu Glu Trp Val Ala Tyr Ile Ser Ser Gly Ser Ser Ile Asn
65                  70                  75                  80

Tyr Ala Asp Thr Val Lys Gly Arg Phe Thr Ile Ser Arg Asp Asn Pro
                85                  90                  95

Lys Asn Thr Leu Phe Leu Gln Met Thr Ser Leu Arg Ser Glu Asp Thr
            100                 105                 110

Ala Ile Tyr Tyr Cys Thr Arg Gly Gly Thr Gly Thr Arg Ser Leu Tyr
        115                 120                 125

Tyr Phe Asp Tyr Trp Gly Gln Gly Ala Thr Leu Ile Val Gly Gly Gly
    130                 135                 140

Gly Ser Gly Gly Gly Gly Ser Gly Gly Gly Gly Ser Asp Ile Gln Met
145                 150                 155                 160

Thr Gln Ile Thr Ser Ser Leu Ser Val Ser Leu Gly Asp Arg Val Ile
                165                 170                 175

Ile Ser Cys Arg Ala Ser Gln Asp Ile Gly Asn Phe Leu Asn Trp Tyr
            180                 185                 190

Gln Gln Lys Pro Asp Gly Ser Leu Lys Leu Leu Ile Tyr Tyr Thr Ser
        195                 200                 205

Arg Leu Gln Ser Gly Val Pro Ser Arg Phe Ser Gly Trp Gly Ser Gly
    210                 215                 220

Thr Asp Tyr Ser Leu Thr Ile Ser Asn Leu Glu Glu Asp Ile Ala
225                 230                 235                 240

Thr Phe Phe Cys Gln Gln Gly Lys Thr Leu Pro Tyr Thr Phe Gly Gly
                245                 250                 255

Gly Thr Lys Leu Glu Ile Lys Glu Pro Lys Ser Pro Asp Lys Thr His
            260                 265                 270

Thr Cys Pro Pro Cys Pro Ala Pro Pro Val Ala Gly Pro Ser Val Phe
        275                 280                 285
```

```
Leu Phe Pro Pro Lys Pro Lys Asp Thr Leu Met Ile Ala Arg Thr Pro
    290                 295                 300

Glu Val Thr Cys Val Val Val Asp Val Ser His Glu Asp Pro Glu Val
305                 310                 315                 320

Lys Phe Asn Trp Tyr Val Asp Gly Val Glu Val His Asn Ala Lys Thr
                325                 330                 335

Lys Pro Arg Glu Glu Gln Tyr Asn Ser Thr Tyr Arg Val Val Ser Val
                340                 345                 350

Leu Thr Val Leu His Gln Asp Trp Leu Asn Gly Lys Glu Tyr Lys Cys
                355                 360                 365

Lys Val Ser Asn Lys Ala Leu Pro Ala Pro Ile Glu Lys Thr Ile Ser
370                 375                 380

Lys Ala Lys Gly Gln Pro Arg Glu Pro Gln Val Tyr Thr Leu Pro Pro
385                 390                 395                 400

Ser Arg Asp Glu Leu Thr Lys Asn Gln Val Ser Leu Thr Cys Leu Val
                405                 410                 415

Lys Gly Phe Tyr Pro Ser Asp Ile Ala Val Glu Trp Glu Ser Asn Gly
                420                 425                 430

Gln Pro Glu Asn Asn Tyr Lys Thr Thr Pro Pro Val Leu Asp Ser Asp
                435                 440                 445

Gly Ser Phe Phe Leu Tyr Ser Lys Leu Thr Val Asp Lys Ser Arg Trp
450                 455                 460

Gln Gln Gly Asn Val Phe Ser Cys Ser Val Met His Glu Ala Leu His
465                 470                 475                 480

Asn His Tyr Thr Gln Lys Ser Leu Ser Leu Ser Pro Gly Lys Ile Tyr
                485                 490                 495

Ile Trp Ala Pro Leu Ala Gly Thr Cys Gly Val Leu Leu Leu Ser Leu
                500                 505                 510

Val Ile Thr Leu Tyr Cys Lys Arg Gly Arg Lys Lys Leu Leu Tyr Ile
                515                 520                 525

Phe Lys Gln Pro Phe Met Arg Pro Val Gln Thr Thr Gln Glu Glu Asp
530                 535                 540

Gly Cys Ser Cys Arg Phe Pro Glu Glu Glu Glu Gly Gly Cys Glu Leu
545                 550                 555                 560

Arg Val Lys Phe Ser Arg Ser Ala Asp Ala Pro Ala Tyr Gln Gln Gly
                565                 570                 575

Gln Asn Gln Leu Tyr Asn Glu Leu Asn Leu Gly Arg Arg Glu Glu Tyr
                580                 585                 590

Asp Val Leu Asp Lys Arg Arg Gly Arg Asp Pro Glu Met Gly Gly Lys
                595                 600                 605

Pro Arg Arg Lys Asn Pro Gln Glu Gly Leu Tyr Asn Glu Leu Gln Lys
610                 615                 620

Asp Lys Met Ala Glu Ala Tyr Ser Glu Ile Gly Met Lys Gly Glu Arg
625                 630                 635                 640

Arg Arg Gly Lys Gly His Asp Gly Leu Tyr Gln Gly Leu Ser Thr Ala
                645                 650                 655

Thr Lys Asp Thr Tyr Asp Ala Leu His Met Gln Ala Leu Pro Pro Arg
                660                 665                 670
```

<210> SEQ ID NO 22
<211> LENGTH: 459
<212> TYPE: PRT
<213> ORGANISM: artificial sequence
<220> FEATURE:
<223> OTHER INFORMATION: MB3.6(VH VL)-FcgRIIIahinge-CD8aTM-41BB.IC- CD3z.IC

<400> SEQUENCE: 22

Met Ala Leu Pro Val Thr Ala Leu Leu Leu Pro Leu Ala Leu Leu Leu
1               5                   10                  15

His Ala Ala Arg Pro Glu Val Val Val Glu Ser Gly Gly Gly Phe
            20                  25                  30

Val Lys Pro Gly Gly Ser Leu Lys Leu Ser Cys Ala Ala Ala Gly Phe
        35                  40                  45

Thr Phe Ser Arg Tyr Ala Met Ser Trp Val Arg Gln Thr Pro Glu Lys
    50                  55                  60

Arg Leu Glu Trp Val Ala Thr Ile Ser Ser Gly Gly Ser His Thr Tyr
65                  70                  75                  80

Tyr Pro Asp Ser Val Lys Gly Arg Phe Thr Ile Ser Arg Asp Asn Ala
                85                  90                  95

Lys Asn Thr Leu Tyr Leu Gln Met Ser Ser Leu Arg Ser Glu Asp Thr
            100                 105                 110

Ala Ile Tyr Tyr Cys Ala Arg Pro Gly Tyr Asp Arg Gly Ala Trp Phe
        115                 120                 125

Phe Asp Val Trp Gly Ala Gly Thr Thr Val Thr Val Ser Ser Gly Gly
    130                 135                 140

Gly Gly Ser Gly Gly Gly Ser Gly Gly Gly Ser Asp Ile Val
145                 150                 155                 160

Leu Thr Gln Ser Pro Ala Thr Leu Ser Val Thr Pro Gly Asp Ser Val
                165                 170                 175

Ser Leu Ser Cys Arg Ala Ser Gln Ile Ile Ser Asn Asn Leu His Trp
            180                 185                 190

Tyr Gln Gln Lys Ser His Glu Ser Pro Arg Leu Leu Ile Lys Tyr Ala
        195                 200                 205

Ser Gln Ser Ile Ser Gly Ile Pro Ser Arg Phe Ser Gly Ser Gly Ser
    210                 215                 220

Gly Thr Asp Phe Thr Leu Ser Ile Asn Ser Val Glu Thr Glu Asp Phe
225                 230                 235                 240

Gly Met Tyr Phe Cys Gln Gln Ser Asn Ser Trp Pro Leu Thr Phe Gly
                245                 250                 255

Ser Gly Thr Lys Leu Glu Ile Lys Arg Gly Leu Ala Val Ser Thr Ile
            260                 265                 270

Ser Ser Phe Phe Pro Pro Gly Tyr Gln Ile Tyr Ile Trp Ala Pro Leu
        275                 280                 285

Ala Gly Thr Cys Gly Val Leu Leu Leu Ser Leu Val Ile Thr Leu Tyr
    290                 295                 300

Cys Lys Arg Gly Arg Lys Lys Leu Leu Tyr Ile Phe Lys Gln Pro Phe
305                 310                 315                 320

Met Arg Pro Val Gln Thr Thr Gln Glu Glu Asp Gly Cys Ser Cys Arg
                325                 330                 335

Phe Pro Glu Glu Glu Glu Gly Gly Cys Glu Leu Arg Val Lys Phe Ser
            340                 345                 350

Arg Ser Ala Asp Ala Pro Ala Tyr Gln Gln Gly Gln Asn Gln Leu Tyr
        355                 360                 365

Asn Glu Leu Asn Leu Gly Arg Arg Glu Glu Tyr Asp Val Leu Asp Lys
    370                 375                 380

Arg Arg Gly Arg Asp Pro Glu Met Gly Gly Lys Pro Arg Arg Lys Asn
385                 390                 395                 400

```
Pro Gln Glu Gly Leu Tyr Asn Glu Leu Gln Lys Asp Lys Met Ala Glu
                405                 410                 415

Ala Tyr Ser Glu Ile Gly Met Lys Gly Glu Arg Arg Arg Gly Lys Gly
            420                 425                 430

His Asp Gly Leu Tyr Gln Gly Leu Ser Thr Ala Thr Lys Asp Thr Tyr
        435                 440                 445

Asp Ala Leu His Met Gln Ala Leu Pro Pro Arg
    450                 455

<210> SEQ ID NO 23
<211> LENGTH: 488
<212> TYPE: PRT
<213> ORGANISM: artificial sequence
<220> FEATURE:
<223> OTHER INFORMATION: MB3.6(VH VL)-CD8ahinge-CD8aTM-41BB.IC-CD3z.IC

<400> SEQUENCE: 23

Met Ala Leu Pro Val Thr Ala Leu Leu Leu Pro Leu Ala Leu Leu Leu
1               5                   10                  15

His Ala Ala Arg Pro Glu Val Val Val Glu Ser Gly Gly Gly Phe
            20                  25                  30

Val Lys Pro Gly Gly Ser Leu Lys Leu Ser Cys Ala Ala Ala Gly Phe
        35                  40                  45

Thr Phe Ser Arg Tyr Ala Met Ser Trp Val Arg Gln Thr Pro Glu Lys
    50                  55                  60

Arg Leu Glu Trp Val Ala Thr Ile Ser Ser Gly Gly Ser His Thr Tyr
65                  70                  75                  80

Tyr Pro Asp Ser Val Lys Gly Arg Phe Thr Ile Ser Arg Asp Asn Ala
                85                  90                  95

Lys Asn Thr Leu Tyr Leu Gln Met Ser Ser Leu Arg Ser Glu Asp Thr
            100                 105                 110

Ala Ile Tyr Tyr Cys Ala Arg Pro Gly Tyr Asp Arg Gly Ala Trp Phe
        115                 120                 125

Phe Asp Val Trp Gly Ala Gly Thr Thr Val Thr Val Ser Ser Gly Gly
    130                 135                 140

Gly Gly Ser Gly Gly Gly Ser Gly Gly Gly Ser Asp Ile Val
145                 150                 155                 160

Leu Thr Gln Ser Pro Ala Thr Leu Ser Val Thr Pro Gly Asp Ser Val
                165                 170                 175

Ser Leu Ser Cys Arg Ala Ser Gln Ile Ile Ser Asn Asn Leu His Trp
            180                 185                 190

Tyr Gln Gln Lys Ser His Glu Ser Pro Arg Leu Leu Ile Lys Tyr Ala
        195                 200                 205

Ser Gln Ser Ile Ser Gly Ile Pro Ser Arg Phe Ser Gly Ser Gly Ser
    210                 215                 220

Gly Thr Asp Phe Thr Leu Ser Ile Asn Ser Val Glu Thr Glu Asp Phe
225                 230                 235                 240

Gly Met Tyr Phe Cys Gln Gln Ser Asn Ser Trp Pro Leu Thr Phe Gly
                245                 250                 255

Ser Gly Thr Lys Leu Glu Ile Lys Arg Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300
```

-continued

```
Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
            325                 330                 335

Gly Arg Lys Lys Leu Leu Tyr Ile Phe Lys Gln Pro Phe Met Arg Pro
        340                 345                 350

Val Gln Thr Thr Gln Glu Glu Asp Gly Cys Ser Cys Arg Phe Pro Glu
    355                 360                 365

Glu Glu Glu Gly Gly Cys Glu Leu Arg Val Lys Phe Ser Arg Ser Ala
    370                 375                 380

Asp Ala Pro Ala Tyr Gln Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
            405                 410                 415

Arg Asp Pro Glu Met Gly Gly Lys Pro Arg Arg Lys Asn Pro Gln Glu
        420                 425                 430

Gly Leu Tyr Asn Glu Leu Gln Lys Asp Lys Met Ala Glu Ala Tyr Ser
    435                 440                 445

Glu Ile Gly Met Lys Gly Glu Arg Arg Arg Gly Lys Gly His Asp Gly
    450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
            485

<210> SEQ ID NO 24
<211> LENGTH: 674
<212> TYPE: PRT
<213> ORGANISM: artificial sequence
<220> FEATURE:
<223> OTHER INFORMATION: MB3.6(VH VL)-IgG1hinge- CD8aTM-41BB.IC-CD3z.IC

<400> SEQUENCE: 24

Met Ala Leu Pro Val Thr Ala Leu Leu Leu Pro Leu Ala Leu Leu Leu
1               5                   10                  15

His Ala Ala Arg Pro Glu Val Val Val Glu Ser Gly Gly Gly Phe
            20                  25                  30

Val Lys Pro Gly Gly Ser Leu Lys Leu Ser Cys Ala Ala Ala Gly Phe
        35                  40                  45

Thr Phe Ser Arg Tyr Ala Met Ser Trp Val Arg Gln Thr Pro Glu Lys
    50                  55                  60

Arg Leu Glu Trp Val Ala Thr Ile Ser Ser Gly Gly Ser His Thr Tyr
65                  70                  75                  80

Tyr Pro Asp Ser Val Lys Gly Arg Phe Thr Ile Ser Arg Asp Asn Ala
            85                  90                  95

Lys Asn Thr Leu Tyr Leu Gln Met Ser Ser Leu Arg Ser Glu Asp Thr
        100                 105                 110

Ala Ile Tyr Tyr Cys Ala Arg Pro Gly Tyr Asp Arg Gly Ala Trp Phe
    115                 120                 125

Phe Asp Val Trp Gly Ala Gly Thr Thr Val Thr Val Ser Ser Gly Gly
    130                 135                 140

Gly Gly Ser Gly Gly Gly Ser Gly Gly Gly Ser Asp Ile Val
145                 150                 155                 160

Leu Thr Gln Ser Pro Ala Thr Leu Ser Val Thr Pro Gly Asp Ser Val
            165                 170                 175
```

```
Ser Leu Ser Cys Arg Ala Ser Gln Ile Ile Ser Asn Asn Leu His Trp
            180                 185                 190

Tyr Gln Gln Lys Ser His Glu Ser Pro Arg Leu Leu Ile Lys Tyr Ala
        195                 200                 205

Ser Gln Ser Ile Ser Gly Ile Pro Ser Arg Phe Ser Gly Ser Gly Ser
    210                 215                 220

Gly Thr Asp Phe Thr Leu Ser Ile Asn Ser Val Glu Thr Glu Asp Phe
225                 230                 235                 240

Gly Met Tyr Phe Cys Gln Gln Ser Asn Ser Trp Pro Leu Thr Phe Gly
                245                 250                 255

Ser Gly Thr Lys Leu Glu Ile Lys Arg Glu Pro Lys Ser Pro Asp Lys
        260                 265                 270

Thr His Thr Cys Pro Pro Cys Pro Ala Pro Pro Val Ala Gly Pro Ser
            275                 280                 285

Val Phe Leu Phe Pro Pro Lys Pro Lys Asp Thr Leu Met Ile Ala Arg
        290                 295                 300

Thr Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
                325                 330                 335

Lys Thr Lys Pro Arg Glu Glu Gln Tyr Asn Ser Thr Tyr Arg Val Val
        340                 345                 350

Ser Val Leu Thr Val Leu His Gln Asp Trp Leu Asn Gly Lys Glu Tyr
    355                 360                 365

Lys Cys Lys Val Ser Asn Lys Ala Leu Pro Ala Pro Ile Glu Lys Thr
370                 375                 380

Ile Ser Lys Ala Lys Gly Gln Pro Arg Glu Pro Gln Val Tyr Thr Leu
385                 390                 395                 400

Pro Pro Ser Arg Asp Glu Leu Thr Lys Asn Gln Val Ser Leu Thr Cys
                405                 410                 415

Leu Val Lys Gly Phe Tyr Pro Ser Asp Ile Ala Val Glu Trp Glu Ser
        420                 425                 430

Asn Gly Gln Pro Glu Asn Asn Tyr Lys Thr Thr Pro Pro Val Leu Asp
    435                 440                 445

Ser Asp Gly Ser Phe Phe Leu Tyr Ser Lys Leu Thr Val Asp Lys Ser
450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
                485                 490                 495

Ile Tyr Ile Trp Ala Pro Leu Ala Gly Thr Cys Gly Val Leu Leu Leu
        500                 505                 510

Ser Leu Val Ile Thr Leu Tyr Cys Lys Arg Gly Arg Lys Lys Leu Leu
    515                 520                 525

Tyr Ile Phe Lys Gln Pro Phe Met Arg Pro Val Gln Thr Thr Gln Glu
530                 535                 540

Glu Asp Gly Cys Ser Cys Arg Phe Pro Glu Glu Glu Glu Gly Gly Cys
545                 550                 555                 560

Glu Leu Arg Val Lys Phe Ser Arg Ser Ala Asp Ala Pro Ala Tyr Gln
                565                 570                 575

Gln Gly Gln Asn Gln Leu Tyr Asn Glu Leu Asn Leu Gly Arg Arg Glu
        580                 585                 590

Glu Tyr Asp Val Leu Asp Lys Arg Arg Gly Arg Asp Pro Glu Met Gly
```

```
                    595                 600                 605
Gly Lys Pro Arg Arg Lys Asn Pro Gln Glu Gly Leu Tyr Asn Glu Leu
            610                 615                 620
Gln Lys Asp Lys Met Ala Glu Ala Tyr Ser Glu Ile Gly Met Lys Gly
625                 630                 635                 640
Glu Arg Arg Arg Gly Lys Gly His Asp Gly Leu Tyr Gln Gly Leu Ser
                645                 650                 655
Thr Ala Thr Lys Asp Thr Tyr Asp Ala Leu His Met Gln Ala Leu Pro
            660                 665                 670
Pro Arg

<210> SEQ ID NO 25
<211> LENGTH: 456
<212> TYPE: PRT
<213> ORGANISM: artificial sequence
<220> FEATURE:
<223> OTHER INFORMATION: KM641(VH VL)-FcgRIIIahinge-CD8aTM-41BB.IC-
      CD3z.IC

<400> SEQUENCE: 25

Met Ala Leu Pro Val Thr Ala Leu Leu Leu Pro Leu Ala Leu Leu Leu
1               5                   10                  15
His Ala Ala Arg Pro Glu Val Thr Leu Val Glu Ser Gly Gly Asp Phe
            20                  25                  30
Val Lys Pro Gly Gly Ser Leu Lys Val Ser Cys Ala Ala Ser Gly Phe
        35                  40                  45
Ala Phe Ser His Tyr Ala Met Ser Trp Val Arg Gln Thr Pro Ala Lys
    50                  55                  60
Arg Leu Glu Trp Val Ala Tyr Ile Ser Ser Gly Gly Ser Gly Thr Tyr
65                  70                  75                  80
Tyr Ser Asp Ser Val Lys Gly Arg Phe Thr Ile Ser Arg Asp Asn Ala
                85                  90                  95
Lys Asn Thr Leu Tyr Leu Gln Met Arg Ser Leu Arg Ser Glu Asp Ser
            100                 105                 110
Ala Met Tyr Phe Cys Thr Arg Val Lys Leu Gly Thr Tyr Tyr Phe Asp
        115                 120                 125
Ser Trp Gly Gln Gly Thr Thr Leu Thr Val Ser Ser Gly Gly Gly Gly
    130                 135                 140
Ser Gly Gly Gly Gly Ser Gly Gly Gly Gly Ser Asp Ile Gln Met Thr
145                 150                 155                 160
Gln Thr Ala Ser Ser Leu Pro Ala Ser Leu Gly Asp Arg Val Thr Ile
                165                 170                 175
Ser Cys Ser Ala Ser Gln Asp Ile Ser Asn Tyr Leu Asn Trp Tyr Gln
            180                 185                 190
Gln Lys Pro Asp Gly Thr Val Lys Leu Leu Ile Phe Tyr Ser Ser Asn
        195                 200                 205
Leu His Ser Gly Val Pro Ser Arg Phe Ser Gly Gly Ser Gly Thr
    210                 215                 220
Asp Tyr Ser Leu Thr Ile Ser Asn Leu Glu Pro Glu Asp Ile Ala Thr
225                 230                 235                 240
Tyr Phe Cys His Gln Tyr Ser Lys Leu Pro Trp Thr Phe Gly Gly Gly
                245                 250                 255
Thr Lys Leu Glu Ile Lys Gly Leu Ala Val Ser Thr Ile Ser Ser Phe
            260                 265                 270
Phe Pro Pro Gly Tyr Gln Ile Tyr Ile Trp Ala Pro Leu Ala Gly Thr
```

-continued

```
                275                 280                 285
Cys Gly Val Leu Leu Ser Leu Val Ile Thr Leu Tyr Cys Lys Arg
        290                 295                 300
Gly Arg Lys Lys Leu Leu Tyr Ile Phe Lys Gln Pro Phe Met Arg Pro
305                 310                 315                 320
Val Gln Thr Thr Gln Glu Glu Asp Gly Cys Ser Cys Arg Phe Pro Glu
                325                 330                 335
Glu Glu Glu Gly Gly Cys Glu Leu Arg Val Lys Phe Ser Arg Ser Ala
            340                 345                 350
Asp Ala Pro Ala Tyr Gln Gln Gly Gln Asn Gln Leu Tyr Asn Glu Leu
                355                 360                 365
Asn Leu Gly Arg Arg Glu Glu Tyr Asp Val Leu Asp Lys Arg Arg Gly
            370                 375                 380
Arg Asp Pro Glu Met Gly Gly Lys Pro Arg Arg Lys Asn Pro Gln Glu
385                 390                 395                 400
Gly Leu Tyr Asn Glu Leu Gln Lys Asp Lys Met Ala Glu Ala Tyr Ser
                405                 410                 415
Glu Ile Gly Met Lys Gly Glu Arg Arg Arg Gly Lys Gly His Asp Gly
            420                 425                 430
Leu Tyr Gln Gly Leu Ser Thr Ala Thr Lys Asp Thr Tyr Asp Ala Leu
                435                 440                 445
His Met Gln Ala Leu Pro Pro Arg
            450                 455

<210> SEQ ID NO 26
<211> LENGTH: 485
<212> TYPE: PRT
<213> ORGANISM: artificial sequence
<220> FEATURE:
<223> OTHER INFORMATION: KM641(VH VL)-CD8ahinge-CD8aTM-41BB.IC-CD3z.IC

<400> SEQUENCE: 26

Met Ala Leu Pro Val Thr Ala Leu Leu Leu Pro Leu Ala Leu Leu Leu
1               5                   10                  15
His Ala Ala Arg Pro Glu Val Thr Leu Val Glu Ser Gly Gly Asp Phe
                20                  25                  30
Val Lys Pro Gly Gly Ser Leu Lys Val Ser Cys Ala Ala Ser Gly Phe
            35                  40                  45
Ala Phe Ser His Tyr Ala Met Ser Trp Val Arg Gln Thr Pro Ala Lys
        50                  55                  60
Arg Leu Glu Trp Val Ala Tyr Ile Ser Ser Gly Gly Ser Gly Thr Tyr
65                  70                  75                  80
Tyr Ser Asp Ser Val Lys Gly Arg Phe Thr Ile Ser Arg Asp Asn Ala
                85                  90                  95
Lys Asn Thr Leu Tyr Leu Gln Met Arg Ser Leu Arg Ser Glu Asp Ser
                100                 105                 110
Ala Met Tyr Phe Cys Thr Arg Val Lys Leu Gly Thr Tyr Tyr Phe Asp
            115                 120                 125
Ser Trp Gly Gln Gly Thr Thr Leu Thr Val Ser Ser Gly Gly Gly Gly
        130                 135                 140
Ser Gly Gly Gly Gly Ser Gly Gly Gly Gly Ser Asp Ile Gln Met Thr
145                 150                 155                 160
Gln Thr Ala Ser Ser Leu Pro Ala Ser Leu Gly Asp Arg Val Thr Ile
                165                 170                 175
Ser Cys Ser Ala Ser Gln Asp Ile Ser Asn Tyr Leu Asn Trp Tyr Gln
```

```
              180                 185                 190
Gln Lys Pro Asp Gly Thr Val Lys Leu Leu Ile Phe Tyr Ser Ser Asn
            195                 200                 205

Leu His Ser Gly Val Pro Ser Arg Phe Ser Gly Gly Gly Ser Gly Thr
        210                 215                 220

Asp Tyr Ser Leu Thr Ile Ser Asn Leu Glu Pro Glu Asp Ile Ala Thr
225                 230                 235                 240

Tyr Phe Cys His Gln Tyr Ser Lys Leu Pro Trp Thr Phe Gly Gly Gly
                245                 250                 255

Thr Lys Leu Glu Ile Lys Thr Thr Thr Pro Ala Pro Arg Pro Pro Thr
            260                 265                 270

Pro Ala Pro Thr Ile Ala Ser Gln Pro Leu Ser Leu Arg Pro Glu Ala
        275                 280                 285

Cys Arg Pro Ala Ala Gly Gly Ala Val His Thr Arg Gly Leu Asp Phe
290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Lys Arg Gly Arg Lys
                325                 330                 335

Lys Leu Leu Tyr Ile Phe Lys Gln Pro Phe Met Arg Pro Val Gln Thr
            340                 345                 350

Thr Gln Glu Glu Asp Gly Cys Ser Cys Arg Phe Pro Glu Glu Glu Glu
        355                 360                 365

Gly Gly Cys Glu Leu Arg Val Lys Phe Ser Arg Ser Ala Asp Ala Pro
    370                 375                 380

Ala Tyr Gln Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
        435                 440                 445

Met Lys Gly Glu Arg Arg Arg Gly Lys Gly His Asp Gly Leu Tyr Gln
    450                 455                 460

Gly Leu Ser Thr Ala Thr Lys Asp Thr Tyr Asp Ala Leu His Met Gln
465                 470                 475                 480

Ala Leu Pro Pro Arg
                485

<210> SEQ ID NO 27
<211> LENGTH: 671
<212> TYPE: PRT
<213> ORGANISM: artificial sequence
<220> FEATURE:
<223> OTHER INFORMATION: KM641(VH VL)-IgG1hinge- CD8aTM-41BB.IC-CD3z.IC

<400> SEQUENCE: 27

Met Ala Leu Pro Val Thr Ala Leu Leu Leu Pro Leu Ala Leu Leu Leu
1               5                   10                  15

His Ala Ala Arg Pro Glu Val Thr Leu Val Glu Ser Gly Gly Asp Phe
            20                  25                  30

Val Lys Pro Gly Gly Ser Leu Lys Val Ser Cys Ala Ala Ser Gly Phe
        35                  40                  45

Ala Phe Ser His Tyr Ala Met Ser Trp Val Arg Gln Thr Pro Ala Lys
```

-continued

```
                50                  55                  60
Arg Leu Glu Trp Val Ala Tyr Ile Ser Ser Gly Gly Ser Gly Thr Tyr
 65                  70                  75                  80

Tyr Ser Asp Ser Val Lys Gly Arg Phe Thr Ile Ser Arg Asp Asn Ala
                 85                  90                  95

Lys Asn Thr Leu Tyr Leu Gln Met Arg Ser Leu Arg Ser Glu Asp Ser
                100                 105                 110

Ala Met Tyr Phe Cys Thr Arg Val Lys Leu Gly Thr Tyr Tyr Phe Asp
                115                 120                 125

Ser Trp Gly Gln Gly Thr Thr Leu Thr Val Ser Ser Gly Gly Gly Gly
130                 135                 140

Ser Gly Gly Gly Gly Ser Gly Gly Gly Gly Ser Asp Ile Gln Met Thr
145                 150                 155                 160

Gln Thr Ala Ser Ser Leu Pro Ala Ser Leu Gly Asp Arg Val Thr Ile
                165                 170                 175

Ser Cys Ser Ala Ser Gln Asp Ile Ser Asn Tyr Leu Asn Trp Tyr Gln
                180                 185                 190

Gln Lys Pro Asp Gly Thr Val Lys Leu Leu Ile Phe Tyr Ser Ser Asn
                195                 200                 205

Leu His Ser Gly Val Pro Ser Arg Phe Ser Gly Gly Ser Gly Thr
210                 215                 220

Asp Tyr Ser Leu Thr Ile Ser Asn Leu Glu Pro Glu Asp Ile Ala Thr
225                 230                 235                 240

Tyr Phe Cys His Gln Tyr Ser Lys Leu Pro Trp Thr Phe Gly Gly Gly
                245                 250                 255

Thr Lys Leu Glu Ile Lys Glu Pro Lys Ser Pro Asp Lys Thr His Thr
                260                 265                 270

Cys Pro Pro Cys Pro Ala Pro Pro Val Ala Gly Pro Ser Val Phe Leu
                275                 280                 285

Phe Pro Pro Lys Pro Lys Asp Thr Leu Met Ile Ala Arg Thr Pro Glu
                290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
                340                 345                 350

Thr Val Leu His Gln Asp Trp Leu Asn Gly Lys Glu Tyr Lys Cys Lys
                355                 360                 365

Val Ser Asn Lys Ala Leu Pro Ala Pro Ile Glu Lys Thr Ile Ser Lys
370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
                420                 425                 430

Pro Glu Asn Asn Tyr Lys Thr Thr Pro Pro Val Leu Asp Ser Asp Gly
                435                 440                 445

Ser Phe Phe Leu Tyr Ser Lys Leu Thr Val Asp Lys Ser Arg Trp Gln
450                 455                 460

Gln Gly Asn Val Phe Ser Cys Ser Val Met His Glu Ala Leu His Asn
465                 470                 475                 480
```

```
His Tyr Thr Gln Lys Ser Leu Ser Leu Ser Pro Gly Lys Ile Tyr Ile
            485                 490                 495

Trp Ala Pro Leu Ala Gly Thr Cys Gly Val Leu Leu Leu Ser Leu Val
            500                 505                 510

Ile Thr Leu Tyr Cys Lys Arg Gly Arg Lys Lys Leu Leu Tyr Ile Phe
            515                 520                 525

Lys Gln Pro Phe Met Arg Pro Val Gln Thr Thr Gln Glu Glu Asp Gly
            530                 535                 540

Cys Ser Cys Arg Phe Pro Glu Glu Glu Glu Gly Gly Cys Glu Leu Arg
545                 550                 555                 560

Val Lys Phe Ser Arg Ser Ala Asp Ala Pro Ala Tyr Gln Gln Gly Gln
            565                 570                 575

Asn Gln Leu Tyr Asn Glu Leu Asn Leu Gly Arg Arg Glu Glu Tyr Asp
            580                 585                 590

Val Leu Asp Lys Arg Arg Gly Arg Asp Pro Glu Met Gly Gly Lys Pro
            595                 600                 605

Arg Arg Lys Asn Pro Gln Glu Gly Leu Tyr Asn Glu Leu Gln Lys Asp
            610                 615                 620

Lys Met Ala Glu Ala Tyr Ser Glu Ile Gly Met Lys Gly Glu Arg Arg
625                 630                 635                 640

Arg Gly Lys Gly His Asp Gly Leu Tyr Gln Gly Leu Ser Thr Ala Thr
            645                 650                 655

Lys Asp Thr Tyr Asp Ala Leu His Met Gln Ala Leu Pro Pro Arg
            660                 665                 670

<210> SEQ ID NO 28
<211> LENGTH: 454
<212> TYPE: PRT
<213> ORGANISM: artificial sequence
<220> FEATURE:
<223> OTHER INFORMATION: BW2121(VH VL)-FcgRIIahinge-CD8aTM-41BB.IC-
      CD3z.IC

<400> SEQUENCE: 28

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Gly Gly Leu
            20                  25                  30

Val Lys Pro Gly Gly Ser Leu Thr Leu Ser Cys Ala Ala Ser Arg Phe
        35                  40                  45

Thr Phe Ser Thr Tyr Ala Met Ser Trp Val Arg Gln Thr Pro Ala Lys
    50                  55                  60

Arg Leu Glu Trp Val Ala Tyr Ile Ser Ser Gly Gly Ala Ser Thr Tyr
65                  70                  75                  80

Tyr Arg Asp Ser Val Lys Gly Arg Phe Thr Ile Ser Arg Asp Asn Ala
                85                  90                  95

Lys Asn Thr Leu Tyr Leu Gln Met Ser Ser Leu Arg Ser Glu Asp Thr
            100                 105                 110

Ala Met Tyr Tyr Cys Ala Arg Gly Gly Ser Arg Tyr Ala Met Asp Tyr
        115                 120                 125

Trp Gly Gln Gly Thr Thr Val Thr Val Ser Ser Gly Gly Gly Gly Ser
    130                 135                 140

Gly Gly Gly Gly Ser Gly Gly Gly Ser Asp Ile Gln Leu Thr Gln
145                 150                 155                 160

Ser Pro Ala Ile Leu Ser Val Ser Pro Gly Glu Arg Val Ser Phe Ser
```

```
                    165                 170                 175
Cys Trp Ala Ser Gln Ser Ile Gly Thr Ser Ile His Trp Tyr Gln Gln
                180                 185                 190

Arg Thr Asn Gly Ser Pro Arg Leu Leu Ile Lys Tyr Ser Ser Glu Ser
            195                 200                 205

Ile Ser Gly Ile Pro Ser Arg Phe Ser Gly Ser Gly Ser Gly Thr Asp
        210                 215                 220

Phe Thr Leu Ser Ile Asn Ser Leu Glu Ser Glu Asp Ile Ala Asp Tyr
225                 230                 235                 240

Tyr Cys Gln Gln Thr Tyr Ser Trp Pro Phe Thr Phe Gly Ser Gly Thr
                245                 250                 255

Lys Leu Glu Ile Gly Leu Ala Val Ser Thr Ile Ser Ser Phe Phe Pro
            260                 265                 270

Pro Gly Tyr Gln Ile Tyr Ile Trp Ala Pro Leu Ala Gly Thr Cys Gly
        275                 280                 285

Val Leu Leu Leu Ser Leu Val Ile Thr Leu Tyr Cys Lys Arg Gly Arg
290                 295                 300

Lys Lys Leu Leu Tyr Ile Phe Lys Gln Pro Phe Met Arg Pro Val Gln
305                 310                 315                 320

Thr Thr Gln Glu Glu Asp Gly Cys Ser Cys Arg Phe Pro Glu Glu Glu
                325                 330                 335

Glu Gly Gly Cys Glu Leu Arg Val Lys Phe Ser Arg Ser Ala Asp Ala
            340                 345                 350

Pro Ala Tyr Gln Gln Gly Gln Asn Gln Leu Tyr Asn Glu Leu Asn Leu
        355                 360                 365

Gly Arg Arg Glu Glu Tyr Asp Val Leu Asp Lys Arg Arg Gly Arg Asp
370                 375                 380

Pro Glu Met Gly Gly Lys Pro Arg Arg Lys Asn Pro Gln Glu Gly Leu
385                 390                 395                 400

Tyr Asn Glu Leu Gln Lys Asp Lys Met Ala Glu Ala Tyr Ser Glu Ile
                405                 410                 415

Gly Met Lys Gly Glu Arg Arg Arg Gly Lys Gly His Asp Gly Leu Tyr
            420                 425                 430

Gln Gly Leu Ser Thr Ala Thr Lys Asp Thr Tyr Asp Ala Leu His Met
        435                 440                 445

Gln Ala Leu Pro Pro Arg
    450

<210> SEQ ID NO 29
<211> LENGTH: 483
<212> TYPE: PRT
<213> ORGANISM: artificial sequence
<220> FEATURE:
<223> OTHER INFORMATION: BW2121(VH VL)-CD8ahinge-CD8aTM-41BB.IC-CD3z.IC

<400> SEQUENCE: 29

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Gly Gly Leu
            20                  25                  30

Val Lys Pro Gly Gly Ser Leu Thr Leu Ser Cys Ala Ala Ser Arg Phe
        35                  40                  45

Thr Phe Ser Thr Tyr Ala Met Ser Trp Val Arg Gln Thr Pro Ala Lys
    50                  55                  60

Arg Leu Glu Trp Val Ala Tyr Ile Ser Ser Gly Gly Ala Ser Thr Tyr
```

```
                65                  70                  75                  80
Tyr Arg Asp Ser Val Lys Gly Arg Phe Thr Ile Ser Arg Asp Asn Ala
                    85                  90                  95

Lys Asn Thr Leu Tyr Leu Gln Met Ser Ser Leu Arg Ser Glu Asp Thr
                    100                 105                 110

Ala Met Tyr Tyr Cys Ala Arg Gly Gly Ser Arg Tyr Ala Met Asp Tyr
                    115                 120                 125

Trp Gly Gln Gly Thr Thr Val Thr Val Ser Ser Gly Gly Gly Gly Ser
        130                 135                 140

Gly Gly Gly Gly Ser Gly Gly Gly Ser Asp Ile Gln Leu Thr Gln
145                 150                 155                 160

Ser Pro Ala Ile Leu Ser Val Ser Pro Gly Glu Arg Val Ser Phe Ser
                165                 170                 175

Cys Trp Ala Ser Gln Ser Ile Gly Thr Ser Ile His Trp Tyr Gln Gln
                180                 185                 190

Arg Thr Asn Gly Ser Pro Arg Leu Leu Ile Lys Tyr Ser Ser Glu Ser
            195                 200                 205

Ile Ser Gly Ile Pro Ser Arg Phe Ser Gly Ser Gly Ser Gly Thr Asp
    210                 215                 220

Phe Thr Leu Ser Ile Asn Ser Leu Glu Ser Glu Asp Ile Ala Asp Tyr
225                 230                 235                 240

Tyr Cys Gln Gln Thr Tyr Ser Trp Pro Phe Thr Phe Gly Ser Gly Thr
                245                 250                 255

Lys Leu Glu Ile Thr Thr Thr Pro Ala Pro Arg Pro Pro Thr Pro Ala
                260                 265                 270

Pro Thr Ile Ala Ser Gln Pro Leu Ser Leu Arg Pro Glu Ala Cys Arg
            275                 280                 285

Pro Ala Ala Gly Gly Ala Val His Thr Arg Gly Leu Asp Phe Ala Cys
        290                 295                 300

Asp Ile Tyr Ile Trp Ala Pro Leu Ala Gly Thr Cys Gly Val Leu Leu
305                 310                 315                 320

Leu Ser Leu Val Ile Thr Leu Tyr Cys Lys Arg Gly Arg Lys Lys Leu
                325                 330                 335

Leu Tyr Ile Phe Lys Gln Pro Phe Met Arg Pro Val Gln Thr Thr Gln
                340                 345                 350

Glu Glu Asp Gly Cys Ser Cys Arg Phe Pro Glu Glu Glu Glu Gly Gly
            355                 360                 365

Cys Glu Leu Arg Val Lys Phe Ser Arg Ser Ala Asp Ala Pro Ala Tyr
        370                 375                 380

Gln Gln Gly Gln Asn Gln Leu Tyr Asn Glu Leu Asn Leu Gly Arg Arg
385                 390                 395                 400

Glu Glu Tyr Asp Val Leu Asp Lys Arg Gly Arg Asp Pro Glu Met
                405                 410                 415

Gly Gly Lys Pro Arg Arg Lys Asn Pro Gln Glu Gly Leu Tyr Asn Glu
                420                 425                 430

Leu Gln Lys Asp Lys Met Ala Glu Ala Tyr Ser Glu Ile Gly Met Lys
            435                 440                 445

Gly Glu Arg Arg Arg Gly Lys Gly His Asp Gly Leu Tyr Gln Gly Leu
        450                 455                 460

Ser Thr Ala Thr Lys Asp Thr Tyr Asp Ala Leu His Met Gln Ala Leu
465                 470                 475                 480

Pro Pro Arg
```

-continued

```
<210> SEQ ID NO 30
<211> LENGTH: 669
<212> TYPE: PRT
<213> ORGANISM: artificial sequence
<220> FEATURE:
<223> OTHER INFORMATION: BW2121(VH VL)-IgG1hinge- CD8aTM-41BB.IC-CD3z.IC

<400> SEQUENCE: 30

Met Ala Leu Pro Val Thr Ala Leu Leu Pro Leu Ala Leu Leu Leu
1               5                   10                  15

His Ala Ala Arg Pro Gln Val Gln Leu Gln Gln Ser Gly Gly Gly Leu
                20                  25                  30

Val Lys Pro Gly Gly Ser Leu Thr Leu Ser Cys Ala Ala Ser Arg Phe
            35                  40                  45

Thr Phe Ser Thr Tyr Ala Met Ser Trp Val Arg Gln Thr Pro Ala Lys
        50                  55                  60

Arg Leu Glu Trp Val Ala Tyr Ile Ser Ser Gly Ala Ser Thr Tyr
65                  70                  75                  80

Tyr Arg Asp Ser Val Lys Gly Arg Phe Thr Ile Ser Arg Asp Asn Ala
                85                  90                  95

Lys Asn Thr Leu Tyr Leu Gln Met Ser Ser Leu Arg Ser Glu Asp Thr
            100                 105                 110

Ala Met Tyr Tyr Cys Ala Arg Gly Gly Ser Arg Tyr Ala Met Asp Tyr
        115                 120                 125

Trp Gly Gln Gly Thr Thr Val Thr Val Ser Ser Gly Gly Gly Gly Ser
    130                 135                 140

Gly Gly Gly Gly Ser Gly Gly Gly Ser Asp Ile Gln Leu Thr Gln
145                 150                 155                 160

Ser Pro Ala Ile Leu Ser Val Ser Pro Gly Glu Arg Val Ser Phe Ser
                165                 170                 175

Cys Trp Ala Ser Gln Ser Ile Gly Thr Ser Ile His Trp Tyr Gln Gln
            180                 185                 190

Arg Thr Asn Gly Ser Pro Arg Leu Leu Ile Lys Tyr Ser Ser Glu Ser
        195                 200                 205

Ile Ser Gly Ile Pro Ser Arg Phe Ser Gly Ser Gly Ser Gly Thr Asp
    210                 215                 220

Phe Thr Leu Ser Ile Asn Ser Leu Glu Ser Glu Asp Ile Ala Asp Tyr
225                 230                 235                 240

Tyr Cys Gln Gln Thr Tyr Ser Trp Pro Phe Thr Phe Gly Ser Gly Thr
                245                 250                 255

Lys Leu Glu Ile Glu Pro Lys Ser Pro Asp Lys Thr His Thr Cys Pro
            260                 265                 270

Pro Cys Pro Ala Pro Pro Val Ala Gly Pro Ser Val Phe Leu Phe Pro
        275                 280                 285

Pro Lys Pro Lys Asp Thr Leu Met Ile Ala Arg Thr Pro Glu Val Thr
    290                 295                 300

Cys Val Val Val Asp Val Ser His Glu Asp Pro Glu Val Lys Phe Asn
305                 310                 315                 320

Trp Tyr Val Asp Gly Val Glu Val His Asn Ala Lys Thr Lys Pro Arg
                325                 330                 335

Glu Glu Gln Tyr Asn Ser Thr Tyr Arg Val Val Ser Val Leu Thr Val
            340                 345                 350

Leu His Gln Asp Trp Leu Asn Gly Lys Glu Tyr Lys Cys Lys Val Ser
        355                 360                 365
```

```
Asn Lys Ala Leu Pro Ala Pro Ile Glu Lys Thr Ile Ser Lys Ala Lys
    370                 375                 380
Gly Gln Pro Arg Glu Pro Gln Val Tyr Thr Leu Pro Pro Ser Arg Asp
385                 390                 395                 400
Glu Leu Thr Lys Asn Gln Val Ser Leu Thr Cys Leu Val Lys Gly Phe
                405                 410                 415
Tyr Pro Ser Asp Ile Ala Val Glu Trp Glu Ser Asn Gly Gln Pro Glu
            420                 425                 430
Asn Asn Tyr Lys Thr Thr Pro Pro Val Leu Asp Ser Asp Gly Ser Phe
        435                 440                 445
Phe Leu Tyr Ser Lys Leu Thr Val Asp Lys Ser Arg Trp Gln Gln Gly
450                 455                 460
Asn Val Phe Ser Cys Ser Val Met His Glu Ala Leu His Asn His Tyr
465                 470                 475                 480
Thr Gln Lys Ser Leu Ser Leu Ser Pro Gly Lys Ile Tyr Ile Trp Ala
                485                 490                 495
Pro Leu Ala Gly Thr Cys Gly Val Leu Leu Leu Ser Leu Val Ile Thr
            500                 505                 510
Leu Tyr Cys Lys Arg Gly Arg Lys Lys Leu Leu Tyr Ile Phe Lys Gln
        515                 520                 525
Pro Phe Met Arg Pro Val Gln Thr Thr Gln Glu Glu Asp Gly Cys Ser
530                 535                 540
Cys Arg Phe Pro Glu Glu Glu Glu Gly Gly Cys Glu Leu Arg Val Lys
545                 550                 555                 560
Phe Ser Arg Ser Ala Asp Ala Pro Ala Tyr Gln Gln Gly Gln Asn Gln
                565                 570                 575
Leu Tyr Asn Glu Leu Asn Leu Gly Arg Arg Glu Glu Tyr Asp Val Leu
            580                 585                 590
Asp Lys Arg Arg Gly Arg Asp Pro Glu Met Gly Gly Lys Pro Arg Arg
        595                 600                 605
Lys Asn Pro Gln Glu Gly Leu Tyr Asn Glu Leu Gln Lys Asp Lys Met
610                 615                 620
Ala Glu Ala Tyr Ser Glu Ile Gly Met Lys Gly Glu Arg Arg Arg Gly
625                 630                 635                 640
Lys Gly His Asp Gly Leu Tyr Gln Gly Leu Ser Thr Ala Thr Lys Asp
                645                 650                 655
Thr Tyr Asp Ala Leu His Met Gln Ala Leu Pro Pro Arg
            660                 665

<210> SEQ ID NO 31
<211> LENGTH: 49
<212> TYPE: DNA
<213> ORGANISM: Artificial sequence
<220> FEATURE:
<223> OTHER INFORMATION: Target TALEN TRAC_T01

<400> SEQUENCE: 31
ttgtcccaca gatatccaga accctgaccc tgccgtgtac cagctgaga          49

<210> SEQ ID NO 32
<211> LENGTH: 530
<212> TYPE: PRT
<213> ORGANISM: Artificial sequence
<220> FEATURE:
<223> OTHER INFORMATION: TAL binding domain  TRAC_T01-L

<400> SEQUENCE: 32
```

```
Leu Thr Pro Gln Gln Val Ala Ile Ala Ser Asn Gly Gly Lys
  1               5                  10                  15

Gln Ala Leu Glu Thr Val Gln Arg Leu Leu Pro Val Leu Cys Gln Ala
             20                  25                  30

His Gly Leu Thr Pro Gln Gln Val Val Ala Ile Ala Ser Asn Asn Gly
             35                  40                  45

Gly Lys Gln Ala Leu Glu Thr Val Gln Arg Leu Leu Pro Val Leu Cys
 50                  55                  60

Gln Ala His Gly Leu Thr Pro Gln Gln Val Val Ala Ile Ala Ser Asn
 65                  70                  75                  80

Gly Gly Lys Gln Ala Leu Glu Thr Val Gln Arg Leu Leu Pro Val
                 85                  90                  95

Leu Cys Gln Ala His Gly Leu Thr Pro Glu Gln Val Val Ala Ile Ala
                100                 105                 110

Ser His Asp Gly Gly Lys Gln Ala Leu Glu Thr Val Gln Arg Leu Leu
             115                 120                 125

Pro Val Leu Cys Gln Ala His Gly Leu Thr Pro Glu Gln Val Val Ala
             130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
             180                 185                 190

Gln Arg Leu Leu Pro Val Leu Cys Gln Ala His Gly Leu Thr Pro Glu
         195                 200                 205

Gln Val Val Ala Ile Ala Ser Asn Ile Gly Gly Lys Gln Ala Leu Glu
     210                 215                 220

Thr Val Gln Ala Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
             260                 265                 270

Leu Thr Pro Glu Gln Val Val Ala Ile Ala Ser Asn Ile Gly Gly Lys
             275                 280                 285

Gln Ala Leu Glu Thr Val Gln Ala Leu Leu Pro Val Leu Cys Gln Ala
         290                 295                 300

His Gly Leu Thr Pro Gln Gln Val Val Ala Ile Ala Ser Asn Asn Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
             340                 345                 350

Ile Gly Gly Lys Gln Ala Leu Glu Thr Val Gln Ala Leu Leu Pro Val
             355                 360                 365

Leu Cys Gln Ala His Gly Leu Thr Pro Gln Gln Val Val Ala Ile Ala
             370                 375                 380

Ser Asn Gly Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser Asn Ile Gly Gly Lys Gln Ala Leu Glu Thr Val Gln Ala
```

```
              420                 425                 430
Leu Leu Pro Val Leu Cys Gln Ala His Gly Leu Thr Pro Gln Gln Val
            435                 440                 445
Val Ala Ile Ala Ser Asn Gly Gly Lys Gln Ala Leu Glu Thr Val
        450                 455                 460
Gln Arg Leu Leu Pro Val Leu Cys Gln Ala His Gly Leu Thr Pro Glu
465                 470                 475                 480
Gln Val Val Ala Ile Ala Ser His Asp Gly Gly Lys Gln Ala Leu Glu
                485                 490                 495
Thr Val Gln Arg Leu Leu Pro Val Leu Cys Gln Ala His Gly Leu Thr
            500                 505                 510
Pro Gln Gln Val Val Ala Ile Ala Ser Asn Gly Gly Arg Pro Ala
        515                 520                 525
Leu Glu
    530

<210> SEQ ID NO 33
<211> LENGTH: 530
<212> TYPE: PRT
<213> ORGANISM: Artificial sequence
<220> FEATURE:
<223> OTHER INFORMATION: TAL binding domain TRAC_T01-R

<400> SEQUENCE: 33

Leu Thr Pro Glu Gln Val Ala Ile Ala Ser His Asp Gly Gly Lys
1               5                   10                  15
Gln Ala Leu Glu Thr Val Gln Arg Leu Leu Pro Val Leu Cys Gln Ala
            20                  25                  30
His Gly Leu Thr Pro Gln Gln Val Val Ala Ile Ala Ser Asn Gly Gly
        35                  40                  45
Gly Lys Gln Ala Leu Glu Thr Val Gln Arg Leu Leu Pro Val Leu Cys
    50                  55                  60
Gln Ala His Gly Leu Thr Pro Glu Gln Val Val Ala Ile Ala Ser His
65                  70                  75                  80
Asp Gly Gly Lys Gln Ala Leu Glu Thr Val Gln Arg Leu Leu Pro Val
                85                  90                  95
Leu Cys Gln Ala His Gly Leu Thr Pro Glu Gln Val Val Ala Ile Ala
            100                 105                 110
Ser Asn Ile Gly Gly Lys Gln Ala Leu Glu Thr Val Gln Ala Leu Leu
        115                 120                 125
Pro Val Leu Cys Gln Ala His Gly Leu Thr Pro Gln Gln Val Val Ala
    130                 135                 140
Ile Ala Ser Asn Asn Gly Gly Lys Gln Ala Leu Glu Thr Val Gln Arg
145                 150                 155                 160
Leu Leu Pro Val Leu Cys Gln Ala His Gly Leu Thr Pro Glu Gln Val
                165                 170                 175
Val Ala Ile Ala Ser His Asp Gly Gly Lys Gln Ala Leu Glu Thr Val
            180                 185                 190
Gln Arg Leu Leu Pro Val Leu Cys Gln Ala His Gly Leu Thr Pro Gln
        195                 200                 205
Gln Val Val Ala Ile Ala Ser Asn Gly Gly Lys Gln Ala Leu Glu
    210                 215                 220
Thr Val Gln Arg Leu Leu Pro Val Leu Cys Gln Ala His Gly Leu Thr
225                 230                 235                 240
Pro Gln Gln Val Val Ala Ile Ala Ser Asn Asn Gly Gly Lys Gln Ala
```

```
            245                 250                 255
Leu Glu Thr Val Gln Arg Leu Leu Pro Val Leu Cys Gln Ala His Gly
        260                 265                 270
Leu Thr Pro Gln Gln Val Val Ala Ile Ala Ser Asn Asn Gly Gly Lys
    275                 280                 285
Gln Ala Leu Glu Thr Val Gln Arg Leu Leu Pro Val Leu Cys Gln Ala
290                 295                 300
His Gly Leu Thr Pro Gln Gln Val Val Ala Ile Ala Ser Asn Gly Gly
305                 310                 315                 320
Gly Lys Gln Ala Leu Glu Thr Val Gln Arg Leu Leu Pro Val Leu Cys
            325                 330                 335
Gln Ala His Gly Leu Thr Pro Glu Gln Val Val Ala Ile Ala Ser Asn
        340                 345                 350
Ile Gly Gly Lys Gln Ala Leu Glu Thr Val Gln Ala Leu Leu Pro Val
    355                 360                 365
Leu Cys Gln Ala His Gly Leu Thr Pro Glu Gln Val Val Ala Ile Ala
370                 375                 380
Ser His Asp Gly Gly Lys Gln Ala Leu Glu Thr Val Gln Arg Leu Leu
385                 390                 395                 400
Pro Val Leu Cys Gln Ala His Gly Leu Thr Pro Glu Gln Val Val Ala
            405                 410                 415
Ile Ala Ser Asn Ile Gly Gly Lys Gln Ala Leu Glu Thr Val Gln Ala
        420                 425                 430
Leu Leu Pro Val Leu Cys Gln Ala His Gly Leu Thr Pro Glu Gln Val
    435                 440                 445
Val Ala Ile Ala Ser His Asp Gly Gly Lys Gln Ala Leu Glu Thr Val
450                 455                 460
Gln Arg Leu Leu Pro Val Leu Cys Gln Ala His Gly Leu Thr Pro Gln
465                 470                 475                 480
Gln Val Val Ala Ile Ala Ser Asn Asn Gly Gly Lys Gln Ala Leu Glu
            485                 490                 495
Thr Val Gln Arg Leu Leu Pro Val Leu Cys Gln Ala His Gly Leu Thr
        500                 505                 510
Pro Gln Gln Val Val Ala Ile Ala Ser Asn Gly Gly Arg Pro Ala
    515                 520                 525
Leu Glu
    530

<210> SEQ ID NO 34
<211> LENGTH: 2814
<212> TYPE: DNA
<213> ORGANISM: Artificial sequence
<220> FEATURE:
<223> OTHER INFORMATION: polynucleotide encoding  TRAC_T01-L TALEN

<400> SEQUENCE: 34
atgggcgatc ctaaaaagaa acgtaaggtc atcgattacc catacgatgt tccagattac    60
gctatcgata tcgccgatct acgcacgctc ggctacagcc agcagcaaca ggagaagatc   120
aaaccgaagg ttcgttcgac agtggcgcag caccacgagg cactggtcgg ccacgggttt   180
acacacgcgc acatcgttgc gttaagccaa cacccggcag cgttagggac cgtcgctgtc   240
aagtatcagg acatgatcgc agcgttgcca gaggcgacac acgaagcgat cgttggcgtc   300
ggcaaacagt ggtccggcgc acgcgctctg gaggccttgc tcacggtggc gggagagttg   360
agaggtccac cgttacagtt ggacacaggc caacttctca agattgcaaa acgtggcggc   420
```

```
gtgaccgcag tggaggcagt gcatgcatgg cgcaatgcac tgacgggtgc cccgctcaac      480 ttgaccccccc agcaggtggt ggccatcgcc agcaatggcg gtggcaagca ggcgctggag     540
acggtccagc ggctgttgcc ggtgctgtgc caggcccacg gcttgacccc ccagcaggtg     600
gtggccatcg ccagcaataa tggtggcaag caggcgctgg agacggtcca gcggctgttg     660
ccggtgctgt gccaggccca cggcttgacc ccccagcagg tggtggccat cgccagcaat     720
ggcggtggca agcaggcgct ggagacggtc agcggctgt tgccggtgct gtgccaggcc     780
cacggcttga ccccggagca ggtggtggcc atcgccagcc acgatggcgg caagcaggcg     840
ctggagacgt ccagcggct gttgccggtg ctgtgccagg cccacggctt gaccccggag      900
caggtggtgg ccatcgccag ccacgatggc ggcaagcagg cgctggagac ggtccagcgg     960
ctgttgccgg tgctgtgcca ggcccacggc ttgaccccgg agcaggtggt ggccatcgcc    1020
agccacgatg gcggcaagca ggcgctggag acggtccagc ggctgttgcc ggtgctgtgc    1080
caggcccacg gcttgacccc ggagcaggtg gtggccatcg ccagcaatat tggtggcaag    1140
caggcgctgg agacggtgca ggcgctgttg ccggtgctgt gccaggccca cggcttgacc    1200
ccggagcagg tggtggccat cgccagccac gatggcggca agcaggcgct ggagacggtc    1260
cagcggctgt tgccggtgct gtgccaggcc cacggcttga ccccggagca ggtggtggcc    1320
atcgccagca atattggtgg caagcaggcg ctggagacgg tgcaggcgct gttgccggtg    1380
ctgtgccagg cccacggctt gaccccccag caggtggtgg ccatcgccag caataatggt    1440
ggcaagcagg cgctggagac ggtccagcgg ctgttgccgg tgctgtgcca ggcccacggc    1500
ttgaccccgg agcaggtggt ggccatcgcc agcaatattg gtggcaagca ggcgctggag    1560
acggtgcagg cgctgttgcc ggtgctgtgc caggcccacg gcttgacccc ccagcaggtg    1620
gtggccatcg ccagcaatgg cggtggcaag caggcgctgg agacggtcca gcggctgttg    1680
ccggtgctgt gccaggccca cggcttgacc ccggagcagg tggtggccat cgccagcaat    1740
attggtggca agcaggcgct ggagacggtg caggcgctgt tgccggtgct gtgccaggcc    1800
cacggcttga ccccccagca ggtggtggcc atcgccagca atggcggtgg caagcaggcg    1860
ctggagacgg tccagcggct gttgccggtg ctgtgccagg cccacggctt gaccccggag    1920
caggtggtgg ccatcgccag ccacgatggc ggcaagcagg cgctggagac ggtccagcgg    1980
ctgttgccgg tgctgtgcca ggcccacggc ttgacccctc agcaggtggt ggccatcgcc    2040
agcaatggcg gcggcaggcc ggcgctggag agcattgttg cccagttatc tcgccctgat    2100
ccggcgttgg ccgcgttgac caacgaccac ctcgtcgcct tggcctgcct cggcgggcgt    2160
cctgcgctgg atgcagtgaa aaagggattg ggggatccta tcagccgttc ccagctggtg    2220
aagtccgagc tggaggagaa gaaatccgag ttgaggcaca agctgaagta cgtgccccac    2280
gagtacatcg agctgatcga gatcgcccgg aacagcaccc aggaccgtat cctggagatg    2340
aaggtgatgg agttcttcat gaaggtgtac ggctacaggg gcaagcacct gggcggctcc    2400
aggaagcccg acggcgccat ctacaccgtg ggctccccca tcgactacgg cgtgatcgtg    2460
gacaccaagg cctactccgg cggctacaac ctgcccatcg ccaggcgca cgaaatgcag    2520 aggtacgtga aggagaacca gaccaggaac aagcacatca cccccaacga gtggtggaag    2580
gtgtacccct ccagcgtgac cgagttcaag ttcctgttcg tgtccggcca cttcaagggc    2640
aactacaagg cccagctgac caggctgaac cacatcacca actgcaacgg cgccgtgctg    2700
tccgtggagg agctcctgat cggcggcgag atgatcaagg ccggcaccct gacccttgag    2760
```

```
                                                     -continued gaggtgagga ggaagttcaa caacggcgag atcaacttcg cggccgactg ataa    2814

<210> SEQ ID NO 35
<211> LENGTH: 2832
<212> TYPE: DNA
<213> ORGANISM: Artificial sequence
<220> FEATURE:
<223> OTHER INFORMATION: polynucleotide encoding TRAC_T01-R TALEN

<400> SEQUENCE: 35
atgggcgatc ctaaaaagaa acgtaaggtc atcgataagg agaccgccgc tgccaagttc      60
gagagacagc acatggacag catcgatatc gccgatctac gcacgctcgg ctacagccag     120
cagcaacagg agaagatcaa accgaaggtt cgttcgacag tggcgcagca ccacgaggca     180
ctggtcggcc acgggtttac acacgcgcac atcgttgcgt taagccaaca cccggcagcg     240
ttagggaccg tcgctgtcaa gtatcaggac atgatcgcac gttgccagag ggcgacacac     300
gaagcgatcg ttggcgtcgg caaacagtgg tccggcgcac gcgctctgga ggccttgctc     360
acggtggcgg gagagttgag aggtccaccg ttacagttgg acacaggcca acttctcaag     420
attgcaaaac gtggcggcgt gaccgcagtg gaggcagtgc atgcatggcg caatgcactg     480
acgggtgccc cgctcaactt gaccccggag caggtggtgg ccatcgccag ccacgatggc     540
ggcaagcagg cgctggagac ggtccagcgc ctgttgccgg tgctgtgcca ggcccacggc     600
ttgacccccc agcaggtggt ggccatcgcc agcaatggcg gtggcaagca ggcgctggag     660
acggtccagc ggctgttgcc ggtgctgtgc caggcccacg gcttgacccc ggagcaggtg     720
gtggccatcg ccagccacga tggcggcaag caggcgctgg agacggtcca gcggctgttg     780
ccggtgctgt gccaggccca cggcttgacc ccggagcagg tggtggccat cgccagcaat     840
attggtggca gcaggcgct ggagacggtc aggcgctgt tgccggtgct gtgccaggcc     900
cacggcttga cccccagca ggtggtggcc atcgccagca ataatggtgg caagcaggcg     960
ctggagacgt ccagcggct gttgccggtg ctgtgccagg cccacggctt gaccccggag    1020
caggtggtgg ccatcgccag ccacgatggc ggcaagcagg cgctggagac ggtccagcgg    1080
ctgttgccgg tgctgtgcca ggcccacggc ttgacccccc agcaggtggt ggccatcgcc    1140
agcaatggcg gtggcaagca ggcgctggag acggtccagc ggctgttgcc ggtgctgtgc    1200
caggcccacg gcttgacccc ccagcaggtg gtggccatcg ccagcaataa tggtggcaag    1260
caggcgctgg agacggtcca gcggctgttg ccggtgctgt gccaggccca cggcttgacc    1320
ccccagcagg tggtggccat cgccagcaat aatggtggca gcaggcgct ggagacggtc    1380 cagcggctgt tgccggtgct gtgccaggcc cacggcttga cccccagca ggtggtggcc    1440 atcgccagca atggcggtgg caagcaggcg ctggagacgg tccagcggct gttgccggtg    1500
ctgtgccagg cccacggctt gaccccggag caggtggtgg ccatcgccag caatattggt    1560
ggcaagcagg cgctggagac ggtgcaggcg ctgttgccgg tgctgtgcca ggcccacggc    1620
ttgaccccgg agcaggtggt ggccatcgcc agccacgatg gcggcaagca ggcgctggag    1680
acggtccagc ggctgttgcc ggtgctgtgc caggcccacg gcttgacccc ggagcaggtg    1740
gtggccatcg ccagcaatat tggtggcaag caggcgctgg agacggtgca ggcgctgttg    1800
ccggtgctgt gccaggccca cggcttgacc ccggagcagg tggtggccat cgccagccac    1860 gatgcggca agcaggcgct ggagacggtc agcggctgt tgccggtgct gtgccaggcc    1920
cacggcttga cccccagca ggtggtggcc atcgccagca ataatggtgg caagcaggcg    1980
ctggagacgg tccagcggct gttgccggtg ctgtgccagg cccacggctt gacccctcag    2040
```

```
caggtggtgg ccatcgccag caatggcggc ggcaggccgg cgctggagag cattgttgcc    2100
cagttatctc gccctgatcc ggcgttggcc gcgttgacca acgaccacct cgtcgccttg    2160
gcctgcctcg gcgggcgtcc tgcgctggat gcagtgaaaa agggattggg ggatcctatc    2220
agccgttccc agctggtgaa gtccgagctg gaggagaaga atccgagtt gaggcacaag     2280 ctgaagtacg tgccccacga gtacatcgag ctgatcgaga tcgcccggaa cagcacccag    2340
gaccgtatcc tggagatgaa ggtgatggag ttcttcatga aggtgtacgg ctacaggggc    2400
aagcacctgg gcggctccag gaagcccgac ggcgccatct acaccgtggg ctcccccatc    2460
gactacggcg tgatcgtgga caccaaggcc tactccggcg gctacaacct gcccatcggc    2520
caggccgacg aaatgcagag gtacgtggag gagaaccaga ccaggaacaa gcacatcaac    2580
cccaacgagt ggtggaaggt gtaccctcc agcgtgaccg agttcaagtt cctgttcgtg     2640
tccggccact tcaagggcaa ctacaaggcc cagctgacca ggctgaacca catcaccaac    2700
tgcaacggcg ccgtgctgtc cgtggaggag ctcctgatcg gcggcgagat gatcaaggcc    2760
ggcaccctga ccctggagga ggtgaggagg aagttcaaca acggcgagat caacttcgcg    2820
gccgactgat aa                                                        2832

<210> SEQ ID NO 36
<211> LENGTH: 5
<212> TYPE: PRT
<213> ORGANISM: artificial sequence
<220> FEATURE:
<223> OTHER INFORMATION: CDR1 of R24 VH chain

<400> SEQUENCE: 36

Asn Phe Gly Met His
1               5

<210> SEQ ID NO 37
<211> LENGTH: 15
<212> TYPE: PRT
<213> ORGANISM: artificial sequence
<220> FEATURE:
<223> OTHER INFORMATION: CDR2 of R24 VH chain

<400> SEQUENCE: 37

Tyr Ile Ser Ser Gly Gly Ser Ser Ile Asn Tyr Ala Asp Thr Val
1               5                   10                  15

<210> SEQ ID NO 38
<211> LENGTH: 13
<212> TYPE: PRT
<213> ORGANISM: artificial sequence
<220> FEATURE:
<223> OTHER INFORMATION: CDR3 of R24 VH chain

<400> SEQUENCE: 38

Gly Gly Thr Gly Thr Arg Ser Leu Tyr Tyr Phe Asp Tyr
1               5                   10

<210> SEQ ID NO 39
<211> LENGTH: 11
<212> TYPE: PRT
<213> ORGANISM: artificial sequence
<220> FEATURE:
<223> OTHER INFORMATION: CDR1 of R24VL chain

<400> SEQUENCE: 39

Arg Ala Ser Gln Asp Ile Gly Asn Phe Leu Asn
```

<210> SEQ ID NO 40
<211> LENGTH: 7
<212> TYPE: PRT
<213> ORGANISM: artificial sequence
<220> FEATURE:
<223> OTHER INFORMATION: CDR2 of R24 VL chain

<400> SEQUENCE: 40

Tyr Thr Ser Arg Leu Gln Ser
1               5

<210> SEQ ID NO 41
<211> LENGTH: 9
<212> TYPE: PRT
<213> ORGANISM: artificial sequence
<220> FEATURE:
<223> OTHER INFORMATION: CDR3 of R24VL chain

<400> SEQUENCE: 41

Gln Gln Gly Lys Thr Leu Pro Tyr Thr
1               5

<210> SEQ ID NO 42
<211> LENGTH: 8
<212> TYPE: PRT
<213> ORGANISM: artificial sequence
<220> FEATURE:
<223> OTHER INFORMATION: CDR1 of MB3.6 VH chain

<400> SEQUENCE: 42

Gly Phe Thr Phe Ser Arg Tyr Ala
1               5

<210> SEQ ID NO 43
<211> LENGTH: 8
<212> TYPE: PRT
<213> ORGANISM: artificial sequence
<220> FEATURE:
<223> OTHER INFORMATION: CDR2 of MB3.6 VH chain

<400> SEQUENCE: 43

Ile Ser Ser Gly Gly Ser His Thr
1               5

<210> SEQ ID NO 44
<211> LENGTH: 14
<212> TYPE: PRT
<213> ORGANISM: artificial sequence
<220> FEATURE:
<223> OTHER INFORMATION: CDR3 of MB3.6 VH chain

<400> SEQUENCE: 44

Ala Arg Pro Gly Tyr Asp Arg Gly Ala Trp Phe Phe Asp Val
1               5                   10

<210> SEQ ID NO 45
<211> LENGTH: 6
<212> TYPE: PRT
<213> ORGANISM: artificial sequence
<220> FEATURE:
<223> OTHER INFORMATION: CDR1 of MB3.6 VL chain

<400> SEQUENCE: 45

Gln Ile Ile Ser Asn Asn
1               5

```
<210> SEQ ID NO 46
<211> LENGTH: 3
<212> TYPE: PRT
<213> ORGANISM: artificial sequence
<220> FEATURE:
<223> OTHER INFORMATION: CDR2 of MB3.6 VL chain

<400> SEQUENCE: 46

Tyr Ala Ser
1

<210> SEQ ID NO 47
<211> LENGTH: 9
<212> TYPE: PRT
<213> ORGANISM: artificial sequence
<220> FEATURE:
<223> OTHER INFORMATION: CDR3 of MB3.6 VL chain

<400> SEQUENCE: 47

Gln Gln Ser Asn Ser Trp Pro Leu Thr
1               5

<210> SEQ ID NO 48
<211> LENGTH: 5
<212> TYPE: PRT
<213> ORGANISM: artificial sequence
<220> FEATURE:
<223> OTHER INFORMATION: CDR1 of KM641 VH chain

<400> SEQUENCE: 48

His Tyr Ala Met Ser
1               5

<210> SEQ ID NO 49
<211> LENGTH: 17
<212> TYPE: PRT
<213> ORGANISM: artificial sequence
<220> FEATURE:
<223> OTHER INFORMATION: CDR2 of KM641 VH chain

<400> SEQUENCE: 49

Tyr Ile Ser Ser Gly Gly Ser Gly Thr Tyr Tyr Ser Asp Ser Val Lys Gly
1               5                   10                  15

<210> SEQ ID NO 50
<211> LENGTH: 10
<212> TYPE: PRT
<213> ORGANISM: artificial sequence
<220> FEATURE:
<223> OTHER INFORMATION: CDR3 of KM641 VH chain

<400> SEQUENCE: 50

Val Lys Leu Gly Thr Tyr Tyr Phe Asp Ser
1               5                   10

<210> SEQ ID NO 51
<211> LENGTH: 11
<212> TYPE: PRT
<213> ORGANISM: artificial sequence
<220> FEATURE:
<223> OTHER INFORMATION: CDR1 of KM641 VL chain

<400> SEQUENCE: 51

Ser Ala Ser Gln Asp Ile Ser Asn Tyr Leu Asn
1               5                   10
```

```
<210> SEQ ID NO 52
<211> LENGTH: 7
<212> TYPE: PRT
<213> ORGANISM: artificial sequence
<220> FEATURE:
<223> OTHER INFORMATION: CDR2 of KM641 VL chain

<400> SEQUENCE: 52

Tyr Ser Ser Asn Leu His Ser
1               5

<210> SEQ ID NO 53
<211> LENGTH: 9
<212> TYPE: PRT
<213> ORGANISM: artificial sequence
<220> FEATURE:
<223> OTHER INFORMATION: CDR3 of KM641 VL chain

<400> SEQUENCE: 53

His Gln Tyr Ser Lys Leu Pro Trp Thr
1               5

<210> SEQ ID NO 54
<211> LENGTH: 8
<212> TYPE: PRT
<213> ORGANISM: artificial sequence
<220> FEATURE:
<223> OTHER INFORMATION: CDR1 of BW2121 VH chain

<400> SEQUENCE: 54

Arg Phe Thr Phe Ser Thr Tyr Ala
1               5

<210> SEQ ID NO 55
<211> LENGTH: 8
<212> TYPE: PRT
<213> ORGANISM: artificial sequence
<220> FEATURE:
<223> OTHER INFORMATION: CDR2 of BW2121 VH chain

<400> SEQUENCE: 55

Ile Ser Ser Gly Gly Ala Ser Thr
1               5

<210> SEQ ID NO 56
<211> LENGTH: 11
<212> TYPE: PRT
<213> ORGANISM: artificial sequence
<220> FEATURE:
<223> OTHER INFORMATION: CDR3 of BW2121 VH chain

<400> SEQUENCE: 56

Ala Arg Gly Gly Ser Arg Tyr Ala Met Asp Tyr
1               5                   10

<210> SEQ ID NO 57
<211> LENGTH: 6
<212> TYPE: PRT
<213> ORGANISM: artificial sequence
<220> FEATURE:
<223> OTHER INFORMATION: CDR1 of BW2121 VL chain

<400> SEQUENCE: 57

Gln Ser Ile Gly Thr Ser
1               5
```

```
<210> SEQ ID NO 58
<211> LENGTH: 3
<212> TYPE: PRT
<213> ORGANISM: artificial sequence
<220> FEATURE:
<223> OTHER INFORMATION: CDR2 of BW2121 VL chain

<400> SEQUENCE: 58

Tyr Ser Ser
1

<210> SEQ ID NO 59
<211> LENGTH: 9
<212> TYPE: PRT
<213> ORGANISM: artificial sequence
<220> FEATURE:
<223> OTHER INFORMATION: CDR3 of BW2121 VL chain

<400> SEQUENCE: 59

Gln Gln Thr Tyr Ser Trp Pro Phe Thr
1               5

<210> SEQ ID NO 60
<211> LENGTH: 135
<212> TYPE: PRT
<213> ORGANISM: Artificial Sequence
<220> FEATURE:
<223> OTHER INFORMATION: RQR8

<400> SEQUENCE: 60

Cys Pro Tyr Ser Asn Pro Ser Leu Cys Ser Gly Gly Gly Gly Ser Glu
1               5                   10                  15

Leu Pro Thr Gln Gly Thr Phe Ser Asn Val Ser Thr Asn Val Ser Pro
            20                  25                  30

Ala Lys Pro Thr Thr Thr Ala Cys Pro Tyr Ser Asn Pro Ser Leu Cys
        35                  40                  45

Ser Gly Gly Gly Gly Ser Pro Ala Pro Arg Pro Pro Thr Pro Ala Pro
50                  55                  60

Thr Ile Ala Ser Gln Pro Leu Ser Leu Arg Pro Glu Ala Cys Arg Pro
65                  70                  75                  80

Ala Ala Gly Gly Ala Val His Thr Arg Gly Leu Asp Phe Ala Cys Asp
                85                  90                  95

Ile Tyr Ile Trp Ala Pro Leu Ala Gly Thr Cys Gly Val Leu Leu Leu
            100                 105                 110

Ser Leu Val Ile Thr Leu Tyr Cys Asn His Arg Asn Arg Arg Arg Val
        115                 120                 125

Cys Lys Cys Pro Arg Pro Trp
    130                 135

<210> SEQ ID NO 61
<211> LENGTH: 49
<212> TYPE: DNA
<213> ORGANISM: Artificial Sequence
<220> FEATURE:
<223> OTHER INFORMATION: Target sequence

<400> SEQUENCE: 61
ttgtcccaca gatatccaga accctgaccc tgccgtgtac cagctgaga          49
```

ANTI-GD3 SPECIFIC CHIMERIC ANTIGEN RECEPTORS FOR CANCER IMMUNOTHERAPY

CROSS-REFERENCE TO RELATED APPLICATIONS

This application is a National Stage entry of International Application No.: PCT/EP2016/061485, filed May 20, 2016, which claims priority to Danish Patent Application No. PA201570296, filed May 20, 2015. The disclosure of the priority applications are hereby incorporated in their entirety by reference.

FIELD OF THE INVENTION

The present invention relates to Chimeric Antigen Receptors (CAR) that are recombinant chimeric proteins able to redirect immune cell specificity and reactivity toward GD3, a ganglioside found in the central nervous system tissues and used to diagnose solid tumors such as melanomas, neuroectodermal tumors and carcinomas and also liquid tumor such as acute lymphoblastic leukemia (ALL) in patients. The CARs according to the invention are particularly useful to treat malignant cells bearing GD3 antigen, when expressed in immune cells, such as T-cells or NK cells. The resulting engineered immune cells display high level of specificity toward malignant GD3 positive cells, conferring safety and efficiency for immunotherapy.

BACKGROUND OF THE INVENTION

Adoptive immunotherapy, which involves the transfer of autologous antigen-specific T cells generated ex vivo, is a promising strategy to treat viral infections and cancer. The T cells used for adoptive immunotherapy can be generated either by expansion of antigen-specific T cells or redirection of T cells through genetic engineering (Park, Rosenberg et al. 2011). Transfer of viral antigen specific T cells is a well-established procedure used for the treatment of transplant associated viral infections and rare viral-related malignancies. Similarly, isolation and transfer of tumor specific T cells has been shown to be successful in treating melanoma.

Novel specificities in T cells have been successfully generated through the genetic transfer of transgenic T cell receptors or chimeric antigen receptors (CARs) (Jena, Dotti et al. 2010). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. First generation CARs have been shown to successfully redirect T-cell cytotoxicity. However, they failed to provide prolonged expansion and anti-tumor activity in vivo. Signaling domains from co-stimulatory molecules, as well as transmembrane and hinge domains have been added to form CARs of second and third generations, leading to some successful therapeutic trials in humans, where T-cells could be redirected against malignant cells expressing CD19 (June et al., 2011). However, the particular combination of signaling domains, transmembrane and co-stimulatory domains used with respect to CD19 ScFv, was rather antigen-specific and cannot be expanded to any antigen markers.

The disialoganglioside GD3 is an acid glycosphingolipid depicted in FIG. 1 which has been shown to be strongly expressed in melanoma cell lines, adult and fetal brain and to a lesser extent in adult and fetal lung (Haraguchi et al, 1994; Nakayama et al. 1996). Gangliosides are a family composed of a common hydrophobic ceramide moiety and a hydrophilic oligosaccharide chain containing one or several sialic acids. Ceramide, therefore a source of GD3, is converted into GD3 by diverse glycosyltransferases and in particular by the GD3 synthase (alpha 2,8-sialyltransferase or ST8Sia I or SATII). GD3 ganglioside, also named alpha-N-acetylneuraminide alpha-2,8-sialyltransferase (ref: Uniprot: Q92185; SIA8A human), an enzyme that is encoded in humans by the ST8SIA1 gene (RefSeq: NP_003025.1. NM_003034.3).

GD3 is highly expressed at early development stages of the central nervous system, when neural cells proliferate actively. At later developmental stages, the GD3 content declines and others gangliosides become major species (Daniotti et al., 1997; Gravotta et al., 1989). In addition, the expression level of gangliosides in general, and GD3 in particular, is very low and restricted in adult extra neural tissues. Nevertheless, GD3 is highly expressed in tumor cells, accounting for more than 80% of melanomas. It is also overexpressed in neuroectodermal tumors (neuroblastoma and glioma) and carcinomas, including lung, breast, colon, prostate and ovary (Lo et al., 2010). In addition, GD3 expression was observed in T cell acute lymphoblastic leukemia (Reaman et al., 1990).

The highly restricted expression of GD3 on select tumor types and the fact that GD3 has been shown to promote tumorigenesis by mediating cell migration, adhesion, proliferation and differentiation (Birklé et al., 2003), makes it an attractive antigen for immunotherapeutic targeting. Previously, Junghans et al. engineered and validated anti-GD3scCARs containing the MB3.6 scFv (Lo et al., 2010; Yun et al., 2000). However, this CAR required systemic infusion of maximal dose of interleukin 2 (IL2) to reach 50% efficacy in the eradication of subcutaneous GD3 positive tumors in established nude mice tumor models. Thus, there is still a need of new anti-GD3 chimeric antigen receptors having improved efficacy, and which can be used for the treatment of both solid or liquid tumors.

The present inventors have thus considered that GD3 could be a valuable target antigen by using CAR-expressing T cells for treating liquid tumors, such as T cell acute lymphoblastic leukemia and solid tumors, such as melanomas, neuroectodermal tumors (neuroblastoma and glioma) and carcinomas, including lung, breast, colon, prostate and ovary.

As an alternative to the previous strategies, the present invention provides with new GD3 specific CAR constructs, which can be expressed in immune cells to target GD3 malignant cells with significant clinical advantage.

SUMMARY OF THE INVENTION

The inventors have generated anti-GD3 specific CARs having different structures and comprising different scFV derived from different GD3 specific antibodies. Preferred CAR polypeptides of the invention comprise an amino acid sequence selected from SEQ ID NO. 19 to 30 (having scFv from R24, MB3.6, KM641 or BW2121; and with a conformation of v1 to v3) preferably SEQ ID NO. 30 (BW2121-v3), SEQ ID NO. 20 (R24-v2) and SEQ ID NO. 21 (R24-v3)

and more preferably SEQ ID NO. 20 (R24-v2). Following non-specific activation in vitro (e.g. with anti CD3/CD28 coated beads and recombinant IL2), T-cells from donors have been transformed with polynucleotides expressing these CARs using viral transduction. In certain instances, the T-cells were further engineered to create non-alloreactive T-cells, more especially by disruption of a component of TCR (αβ-T-Cell receptors) to prevent Graft versus host reaction.

The resulting engineered T-cells displayed reactivity in-vitro against GD3 positive cells to various extend, showing that the CARs of the present invention contribute to antigen dependent activation, and also proliferation, of the T-cells, making them useful for immunotherapy.

The polypeptides and polynucleotide sequences encoding the CARs of the present invention are detailed in the present specification.

The engineered immune cells of the present invention are particularly useful for therapeutic applications, such as for treating solid tumors such as melanomas, neuroblastoma, glioma or breast, colon, lung, prostate or ovary tumors, and liquid tumors such as T-cell acute lymphoblastic leukemia.

DESCRIPTION OF THE FIGURES

FIG. 6: During primary screening, analysis of total expression of 12 scCARs in human T cells by western blot using an anti-human CD3 zeta mAb. (A) Experiment 1. (B) Experiment 2.

FIG. 18: Individual amino acid residues substitutions with respect to SEQ ID NO. 11 concerned by R24 VH humanization.

FIG. 19: Humanization strategy for R24 VL (SEQ ID NO. 12) of anti-GD3 CAR based on R24 ScFv based respectively on closest mouse germline IGKV10-96*01 and closest human germline gene IGKV1-33*01.

FIG. 20: Individual amino acid residues substitutions with respect to SEQ ID NO. 11 concerned by R24 VH humanization.

DETAILED DESCRIPTION OF THE INVENTION

Figure 1:
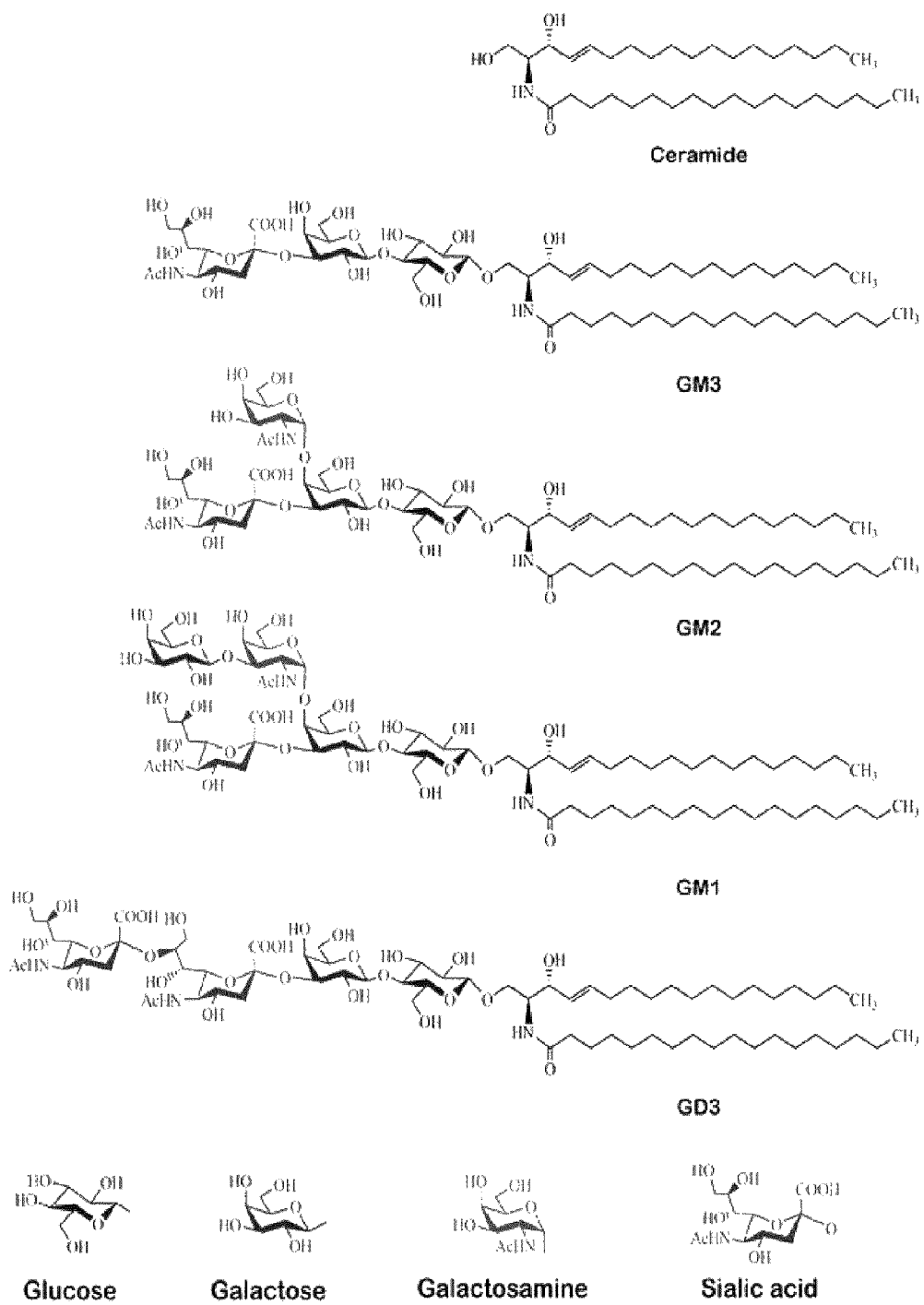
FIG. 1: Structure of the GD3 ganglioside which is composed of two sialic acids linked to a lactosylceramide core common to many gangliosides.

Unless specifically defined herein, all technical and scientific terms used have the same meaning as commonly understood by a skilled artisan in the fields of gene therapy, biochemistry, genetics, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, N.Y.: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

GD3 specific Chimeric Antigen Receptors

The present invention relates to new designs of anti-GD3 chimeric antigen receptor (CAR) comprising an extracellular ligand-binding domain, a transmembrane domain and a signaling transducing domain.

The term "extracellular ligand-binding domain" as used herein is defined as an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state.

The antigen binding domain of the anti-GD3 CARs of the invention can be any domain that binds to the off-tissue antigen including but not limited to a monoclonal antibody, a recombinant antibody, a human antibody, a humanized antibody, and a functional fragment thereof.

In a preferred embodiment, said extracellular ligand-binding domain comprises a single chain antibody fragment (scFv) comprising the light ($V_L$) and the heavy ($V_H$) variable fragment of a target antigen specific monoclonal anti GD3 antibody joined by a flexible linker. Said $V_L$ and $V_H$ are preferably selected from the antibodies referred to as R24, MB3.6, KM641 and BW2121 as indicated in Table 4. They are preferably linked together by a flexible linker comprising for instance the sequence SEQ ID NO:10. In other words, said CARs preferentially comprise an extracellular ligand-binding domain comprising a polypeptide sequence displaying at least 90%, 95% 97% or 99% identity with an amino acid sequence selected from the group consisting of SEQ ID NO: 11 to SEQ ID NO: 18. By the term "recombinant antibody" as used herein, is meant an antibody or antibody fragment which is generated using recombinant DNA technology, such as, for example, an antibody or antibody fragment expressed by a bacteriophage, a yeast expression system or a mammalian cell expression system, and more especially by a T cell transduced with a viral vector comprising a nucleic acid sequence encoding CDR regions of an antibody. The term should also be construed to mean an antibody or antibody fragment which has been generated by the synthesis of a DNA molecule encoding the antibody or antibody fragment and which DNA molecule expresses an antibody or antibody fragment protein, or an amino acid sequence specifying the antibody or antibody fragment, wherein the DNA or amino acid sequence has been obtained using recombinant or synthetic DNA or amino acid sequence technology which is available and well known in the art.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565, 332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., J. Immunol., 169: 1119-25 (2002), Caldas et al., Protein Eng., 13(5):353-60 (2000), Morea et al., Methods, 20(3):267-79 (2000), Baca et al., J. Biol. Chem., 272(16): 10678-84 (1997), Roguska et al., Protein Eng., 9(10):895-904 (1996), Couto et al., Cancer Res., 55 (23 Supp):5973s-5977s (1995), Couto et al., Cancer Res., 55(8): 1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, for example improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties).

In another embodiment, said anti-GD3 specific CAR of the invention comprises an extracellular ligand-binding domain wherein the VH polypeptide comprises a CDR sequence of the R24 antibody selected from SEQ ID NO. 36 (CDR1), SEQ ID NO. 37 (CDR2) and SEQ ID NO. 38 (CDR3), and said VL polypeptide sequence comprises a CDR sequence of the R24 antibody selected from SEQ ID NO. 39 (CDR1), SEQ ID NO. 40 (CDR2) and SEQ ID NO. 41 (CDR3).

In another embodiment, said anti-GD3 specific CAR of the invention comprises an extracellular ligand-binding domain, wherein the VH comprises a CDR sequence from the MB3.6 antibody, for instance, one selected from SEQ ID NO. 42 (CDR1), SEQ ID NO. 43 (CDR2) and SEQ ID NO. 44 (CDR3), and said VL comprises a CDR sequence of the MB3.6 antibody, for instance, one selected from SEQ ID NO. 45 (CDR1), SEQ ID NO. 46 (CDR2) and SEQ ID NO. 47 (CDR3).

In another embodiment, said anti-GD3 specific CAR of the invention comprises an extracellular ligand-binding domain, wherein the VH polypeptide sequence comprises a CDR sequence from the KM641 antibody, for instance, one selected from SEQ ID NO. 48 (CDR1), SEQ ID NO. 49

(CDR2) and SEQ ID NO. 50 (CDR3), and said VL polypeptide sequence comprises a CDR sequence from the KM641 antibody, for instance, one selected from SEQ ID NO. 51 (CDR1), SEQ ID NO. 52 (CDR2) and SEQ ID NO. 53 (CDR3).

In another embodiment, said anti-GD3 specific CAR of the invention comprises an extracellular ligand-binding domain, wherein the VH polypeptide sequence comprises a CDR sequence from BW2121, for instance, one selected from SEQ ID NO. 54 (CDR1), SEQ ID NO. 55 (CDR2) and SEQ ID NO. 56 (CDR3), and said VL polypeptide sequence comprises a CDR sequence from BW2121 antibody, for instance, one selected from SEQ ID NO. 57 (CDR1), SEQ ID NO. 58 (CDR2) and SEQ ID NO. 59 (CDR3).

Figure 17:
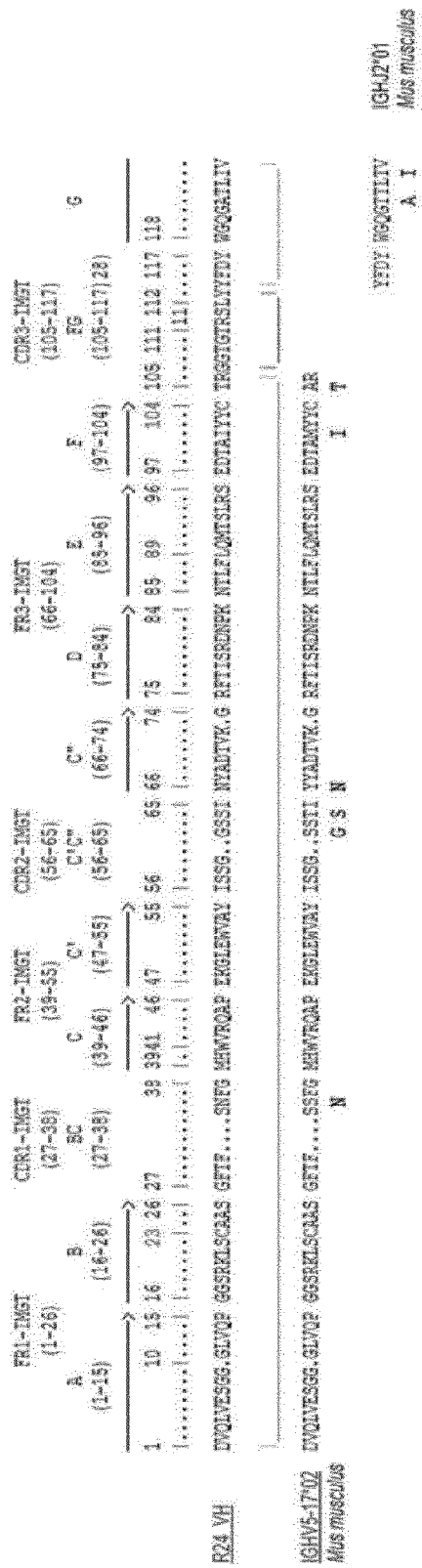
FIG. 17: Humanization strategy for R24 VH (SEQ ID NO. 11) of anti-GD3 CAR based on R24 ScFv based respectively on closest mouse germline IGHV5-17*02 and closest human germline gene IGHV3-NL1*01.
Figure 19:
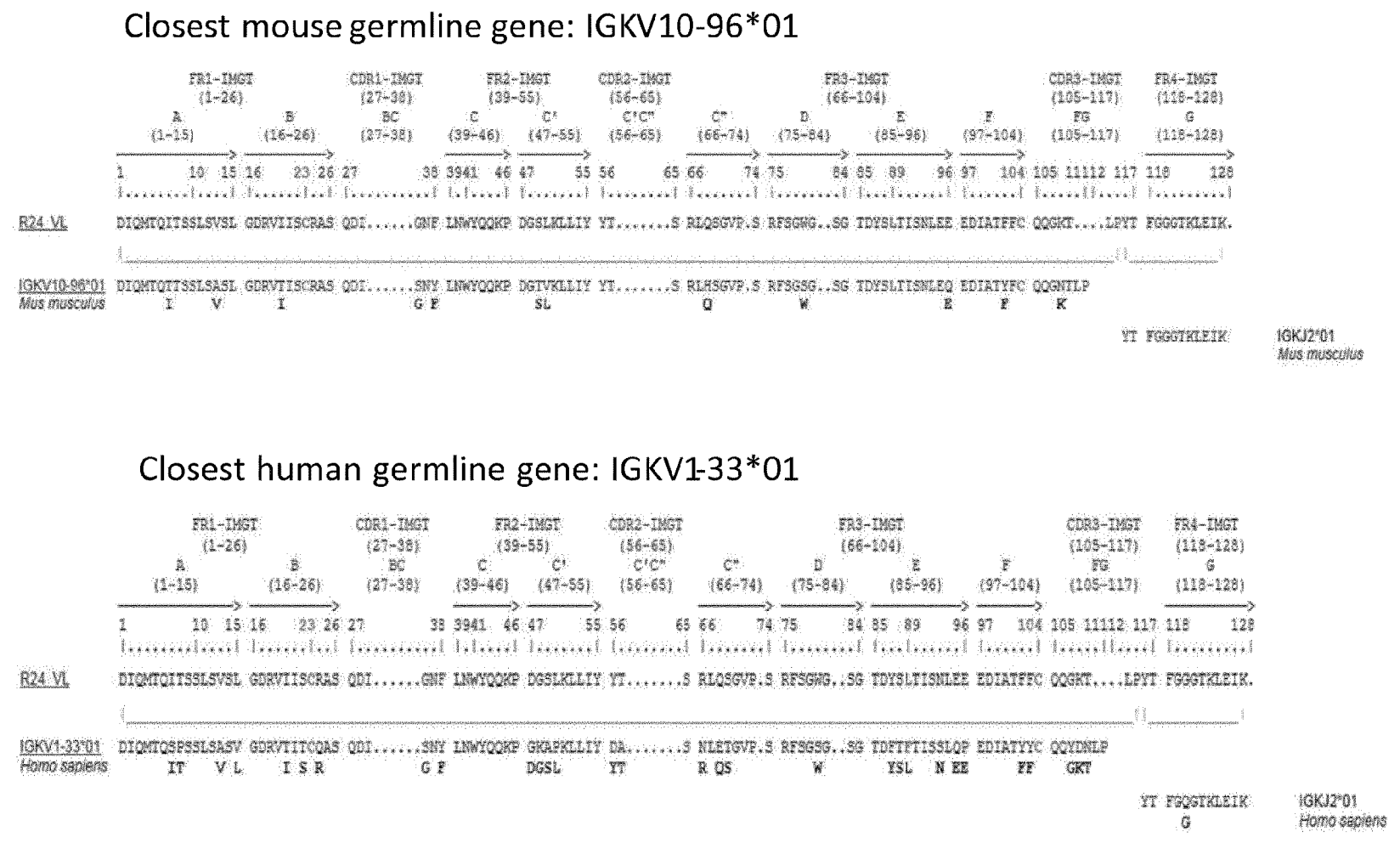

According to one of its preferred embodiments, the invention provides humanizing the foreign framework regions (FRs) of the heavy and light chain variable domains of the anti-R24 ScFvs of SEQ ID NO. 11 and SEQ ID NO. 12 by changing the murine framework surface residues that are not observed in human immunoglobulins. These residues are typically mutated into those observed in the most resembling human counterpart. This technique of resurfacing an antibody, which was first described by Padlan (A possible procedure for reducing the immunogenicity of antibody variable domains while preserving their ligand-binding properties, 1991, Molecular *Immunology*, 28 (4-5): 489-4981991). Such an approach is shown in FIGS. 17 and 19, with the human counterparts IGHV3-NL1*01 and IGKV1-33*01.

As a result, amino acid mutations, preferably substitutions, can be introduced into SEQ ID NO. 11 and SEQ ID NO. 12 at any of the following positions of the CAR GD3 according to the present invention in view of reducing the immunogenicity to humans:

SEQ ID NO. 11 (R24-VH): L12, R19, K20, N36, F37, E47, A54, Y55, S57, I65, N66, T70, P83, F88, T92, S96, I101, T105, R106, A122, T123, L124 and I125.

SEQ ID NO. 12 (R24-VL): I7, T8, V13, L15, I20, S22, R24, G36, F38, D47, G48, S49, L50, Y56, T57, R66, Q68, S69, W79, Y87, S88, L89, N93, E95, E96, F102, F103, G107, K108, T109 and G120.

The present invention thus covers humanized functional variants of CAR GD3, wherein said CAR comprises a polypeptide sequence binding a GD3 antigen that can display up to 18% and 24% variability in its amino acid composition with respect to SEQ ID NO. 11 and SEQ ID NO. 12 respectively.

The amino acid sequence of the ScFv that comprises R24 VH and VL under humanized form, generally display an overall amino acid identity higher than 80%, and more generally, the anti-GD3 specific CAR of the invention comprises an extracellular ligand-binding domain that comprises a polypeptide that shares at least 85% identity with SEQ ID NO. 11 and/or SEQ ID NO. 12.

Preferred amino acid substitutions into R24 VH and/or VL resulting form the humanization approach displayed in FIGS. 17 and 19 are as follows (first letter correspond to the wild type murine sequence, last letter is proposed for substitution):

SEQ ID NO. 11 (R24-VH): L12V, R19L, K20R, N36S, F37Y, E47G, A54S, Y55V, S57Y, I65T, N66Y, T70S, P83S, F88Y, T92N, S96A, I101V, T105A, R106K, A122T, T123L, L124V and I125T.

SEQ ID NO. 12 (R24-VL): I7S, T8P, V13A, L15V, I20T, S22T, R24Q, G36S, F38Y, D47G, G48K, S49A, L50P, Y56D, T57A, R66N, Q68E, S69T, W79S, Y87F, S88T, L89F, N93S, E95Q, E96P, F102Y, F103Y, G107Y, K108D, T109N and G120Q.

Accordingly, the present invention encompasses any GD3 CAR, in particular such humanized functional variants of CAR GD3, comprising an amino acid sequence having identity to SEQ ID NO. 11 and/or SEQ ID NO. 12 including at least one of the above mutated or substituted residues.

However, the above procedures to humanize the ScFv may sometimes lead to reduction of binding affinity because certain framework residues are important for maintaining the conformation of the CDRs. This downside can be mitigated by reintroducing murine residues into the human framework at positions that are deemed to be critical for CDR loop conformation, called "Vernier zone residues". In the work presented here, it has been determined that keeping some mouse amino acids in human background could be critical for maintaining an optimal activity (see FIGS. 18 and 20). Some residues would thereby need to be conserved into the humanized R24-VH and R24-VL amino acid sequences for an optimal activity of the functional variants of CAR GD3 according to the invention. Without being exhaustive, such "Vernier zone residues" appear as follows:

SEQ ID NO. 11 (R24-VH): V2, W52, V53, A54, F76, I78, R80, N82 and/or L87,

SEQ ID NO. 12 (R24-VL): I2, M4, W41, Y42, L52, L53, I54, Y55, G78, G80, G82, T83 and/or Y85.

From the same analysis, it appears that some residues are more critical to CDR loop conformation into SEQ ID NO. 11 and 12. These residues, as well as the "Vernier zone residues are preferably to be maintained into (i.e. not mutated) into the functional variants of CAR GD3 according to the present invention.

SEQ ID NO. 11 (R24-VH): D1, A54, Y55, N64, P83, and/or F88, and more critically, A54, Y55 and/or N64;

SEQ ID NO. 12 (R24-VL): 7I, 8T, 24R, 66R, 68Q, 79W, Y85, S86, L87, F101 and/or F102, and more critically, 66R, Y85 and/or F102.

Accordingly, the present invention encompasses any GD3 CAR, in particular humanized functional variants of CAR GD3 as previously described, comprising an amino acid sequence having identity to SEQ ID NO. 11 and/or SEQ ID NO. 12, preferably at least 80% sequence identity, wherein the above aminoacids have been maintained (i.e. not mutated).

Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within a CAR of the invention can be replaced with other amino acid residues from the same side chain family and the altered CAR can be tested for the ability to bind GD3 using the functional assays described herein.

The signal transducing domain or intracellular signaling domain of a CAR according to the present invention is responsible for intracellular signaling following the binding of extracellular ligand binding domain to the target resulting in the activation of the immune cell and immune response. In other words, the signal transducing domain is responsible for the activation of at least one of the normal effector functions of the immune cell in which the CAR is expressed. For example, the effector function of a T cell can be a cytolytic activity or helper activity including the secretion of cytokines. Thus, the term "signal transducing domain" refers to the portion of a protein which transduces the effector signal function signal and directs the cell to perform a specialized function.

Preferred examples of signal transducing domain for use in a CAR can be the cytoplasmic sequences of the T cell receptor and co-receptors that act in concert to initiate signal transduction following antigen receptor engagement, as well as any derivate or variant of these sequences and any synthetic sequence that has the same functional capability. Signal transduction domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM used in the invention can include as non-limiting examples those derived from TCRzeta, FcRgamma, FcRbeta, FcRepsilon, CD3gamma, CD3delta, CD3epsilon, CD5, CD22, CD79a, CD79b and CD66d. In a preferred embodiment, the signaling transducing domain of the CAR can comprise the CD3zeta signaling domain which has amino acid sequence with at least 70%, preferably at least 80%, more preferably at least 90%, 95% 97% or 99% sequence identity with amino acid sequence selected from the group consisting of (SEQ ID NO: 9).

In particular embodiment the signal transduction domain of the CAR of the present invention comprises a co-stimulatory signal molecule. A co-stimulatory molecule is a cell surface molecule other than an antigen receptor or their ligands that is required for an efficient immune response. "Co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory ligand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-1BB, OX40, CD30, CD40, PD-1, ICOS, lymphocyte function-associated antigen-1 (LFA-1), CD2, CD7, LTGHT, NKG2C, B7-H3, a ligand that specifically binds with CD83.

A "co-stimulatory molecule" refers to the cognate binding partner on a T-cell that specifically binds with a co-stimulatory ligand, thereby mediating a co-stimulatory response by the cell, such as, but not limited to proliferation. Co-stimulatory molecules include, but are not limited to, an MHC class I molecule, BTLA and Toll ligand receptor. Examples of costimulatory molecules include CD27, CD28, CD8, 4-1BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83 and the like.

In a preferred embodiment, the signal transduction domain of the CAR of the present invention comprises a part of co-stimulatory signal molecule selected from the group consisting of fragment of 4-1BB (GenBank: AAA53133) and CD28 (NP_006130.1). In particular the signal transduction domain of the CAR of the present invention comprises amino acid sequence which comprises at least 70%, preferably at least 80%, more preferably at least 90%, 95% 97% or 99% sequence identity with amino acid sequence selected from the group consisting of SEQ ID NO: 8.

A CAR according to the present invention is expressed on the surface membrane of the cell. Thus, such CAR further comprises a transmembrane domain. The distinguishing features of appropriate transmembrane domains comprise the ability to be expressed at the surface of a cell, preferably in the present invention an immune cell, in particular lymphocyte cells or Natural killer (NK) cells, and to interact together for directing cellular response of immune cell against a predefined target cell. The transmembrane domain can be derived either from a natural or from a synthetic source. The transmembrane domain can be derived from any membrane-bound or transmembrane protein. As non-limiting examples, the transmembrane polypeptide can be a subunit of the T-cell receptor such as α, β, γ or ζ, polypeptide constituting CD3 complex, IL2 receptor p55 (α chain), p75 (β chain) or γ chain, subunit chain of Fc receptors, in particular Fcγ receptor III or CD proteins. Alternatively the transmembrane domain can be synthetic and can comprise predominantly hydrophobic residues such as leucine and valine. In a preferred embodiment said transmembrane domain is derived from the human CD8 alpha chain (e.g. NP_001139345.1) The transmembrane domain can further comprise a hinge region between said extracellular ligand-binding domain and said transmembrane domain. The term "hinge region" used herein generally means any oligo- or polypeptide that functions to link the transmembrane domain to the extracellular ligand-binding domain. In particular, hinge region are used to provide more flexibility and accessibility for the extracellular ligand-binding domain. A hinge region may comprise up to 300 amino acids, preferably 10 to 100 amino acids and most preferably 25 to 50 amino acids. Hinge region may be derived from all or part of naturally occurring molecules, such as from all or part of the extracellular region of CD8, CD4 or CD28, or from all or part of an antibody constant region. Alternatively the hinge region may be a synthetic sequence that corresponds to a naturally occurring hinge sequence, or may be an entirely synthetic hinge sequence. In a preferred embodiment said hinge domain comprises a part of human CD8 alpha chain, FcγRIIIα receptor or IgG1 respectively referred to in this specification as SEQ ID NO. 3, SEQ ID NO. 4 and SEQ ID NO. 5, or hinge polypeptides which display preferably at least 80%, more preferably at least 90%, 95% 97% or 99% sequence identity with these polypeptides.

A CAR according to the invention generally further comprises a transmembrane domain (TM) preferably selected from CD8α and 4-1BB, showing identity with the polypeptides of SEQ ID NO. 6 or 7, and more preferably with SEQ ID NO. 6 (CD8α TM).

Downregulation or mutation of target antigens is commonly observed in cancer cells, creating antigen-loss escape variants. Thus, to offset tumor escape and render immune cell more specific to target, the anti-GD3 specific CAR according to the invention can comprise another extracellular ligand-binding domains, to simultaneously bind different elements in target thereby augmenting immune cell activation and function. In one embodiment, the extracellular ligand-binding domains can be placed in tandem on the same transmembrane polypeptide, and optionally can be separated by a linker. In another embodiment, said different extracellular ligand-binding domains can be placed on different transmembrane polypeptides composing the CAR. In another embodiment, the present invention relates to a population of CARs comprising each one different extracellular ligand binding domains. In a particular, the present invention relates to a method of engineering immune cells comprising providing an immune cell and expressing at the surface of said cell a population of CAR each one comprising different extracellular ligand binding domains. In another particular embodiment, the present invention relates to a method of engineering an immune cell comprising providing an immune cell and introducing into said cell polynucleotides encoding polypeptides composing a population of CAR each one comprising different extracellular ligand binding domains. By population of CARs, it is meant at least two, three, four, five, six or more CARs each one comprising different extracellular ligand binding domains. The different extracellular ligand binding domains according to the present invention can preferably simultaneously bind different elements in target thereby augmenting immune cell activation and function. The present invention also relates to an isolated immune cell which comprises a population of CARs each one comprising different extracellular ligand binding domains.

Polynucleotides, Vectors:

The present invention also relates to polynucleotides, vectors encoding the above described CAR according to the invention.

The polynucleotide may consist in an expression cassette or expression vector (e.g. a plasmid for introduction into a bacterial host cell, or a viral vector such as a baculovirus vector for transfection of an insect host cell, or a plasmid or viral vector such as a lentivirus for transfection of a mammalian host cell).

In a particular embodiment, the different nucleic acid sequences can be included in one polynucleotide or vector which comprises a nucleic acid sequence encoding ribosomal skip sequence such as a sequence encoding a 2A peptide. 2A peptides, which were identified in the Aphthovirus subgroup of picornaviruses, causes a ribosomal "skip" from one codon to the next without the formation of a peptide bond between the two amino acids encoded by the codons (see (Donnelly and Elliott 2001; Atkins, Wills et al. 2007; Doronina, Wu et al. 2008)). By "codon" is meant three nucleotides on an mRNA (or on the sense strand of a DNA molecule) that are translated by a ribosome into one amino acid residue. Thus, two polypeptides can be synthesized from a single, contiguous open reading frame within an mRNA when the polypeptides are separated by a 2A oligopeptide sequence that is in frame. Such ribosomal skip mechanisms are well known in the art and are known to be used by several vectors for the expression of several proteins encoded by a single messenger RNA.

To direct transmembrane polypeptide into the secretory pathway of a host cell, a secretory signal sequence (also known as a leader sequence, prepro sequence or pre sequence) is provided in polynucleotide sequence or vector sequence. The secretory signal sequence is operably linked to the transmembrane nucleic acid sequence, i.e., the two sequences are joined in the correct reading frame and positioned to direct the newly synthesized polypeptide into the secretory pathway of the host cell. Secretory signal sequences are commonly positioned 5' to the nucleic acid sequence encoding the polypeptide of interest, although certain secretory signal sequences may be positioned elsewhere in the nucleic acid sequence of interest (see, e.g., Welch et al., U.S. Pat. No. 5,037,743; Holland et al., U.S. Pat. No. 5,143,830). In a preferred embodiment the signal peptide comprises the amino acid sequence SEQ ID NO: 1 and 2.

Those skilled in the art will recognize that, in view of the degeneracy of the genetic code, considerable sequence variation is possible among these polynucleotide molecules. Preferably, the nucleic acid sequences of the present invention are codon-optimized for expression in mammalian cells, preferably for expression in human cells. Codon-optimization refers to the exchange in a sequence of interest of codons that are generally rare in highly expressed genes of a given species by codons that are generally frequent in highly expressed genes of such species, such codons encoding the amino acids as the codons that are being exchanged.

The present invention provides inter cilia an expression vector in the form of a lentiviral vector comprising a polynucleotide sequence encoding a CAR according to the present invention.

As such, the lentiviral vector may comprise a polynucleotide sequence encoding a CAR according to the present invention operably linked to a promoter (such as the Spleen Focus Forming Virus promoter (SFFV)). With "operably linked" it is meant a juxtaposition wherein the components described are in a relationship permitting them to function in their intended manner. A gene (such as a CAR encoding polynucleotide sequence) is "operably linked" to a promoter when its transcription is under the control of said promoter and this transcription results in the production of the product encoded by said gene.

The lentiviral vector of the present invention typically contains regulatory elements such as 5' and 3' long terminal repeat (LTR) sequences, but may also contain other structural and functional genetic elements that are primarily derived from a lentivirus. Such structural and functional genetic elements are well known in the art. The lentiviral vector may, for example, contain the genes gag, pol and env. Preferably, however, the lentiviral vector of the presention invention does not contain the genes gag, pot and env. As further regulatory elements the lentiviral vecor may included one or more (such as two or more) of a packaging singal (such as the packaging signal ψ), a primer binding site, a trans-activation-responsive region (TAR) and a rev-responsive element (RRE).

The 5' and 3' long terminal repeat (LTR) sequences typically flanking the lentiviral genome have promoter/enhancer activity and are essential for the correct expression of the full-length lentiviral vector transcript. The LTRs usually include the repetitive sequence U3RU5 present at both the 5'- and 3' ends of a double-stranded DNA molecule, which is a combination of 5' R-U5 segment and the 3' U3-R segment of the single-stranded RNA, wherein repetition R occurs at both termini of the RNA, while U5 (unique sequence 5) only occurs at the 5' end of the RNA and U3 (unique sequence 3) only occurs at the 3' end of the RNA. However, lentiviral vectors have been improved in their safety by removal of the U3 sequence, resulting in "self-inactivating" vectors that are entirely devoid of viral promoter and enhancer sequences originally present within the LTRs.

The term "self-inactivating" or "SIN," thus refers to a vector in which the 3' LTR enhancer-promoter sequence (i.e. U3 sequence) has been modified (e.g., by deletion or substitution) to prevent viral transcription beyond the first round of viral replication. Consequently, the vector is capable of infecting and then integrating into the host genome only once, and cannot be passed further, thereby increasing the safety of the use of the vector as a gene delivery vector.

According to some embodiments, the lentiviral vector is a self-inactivating (SIN) lentiviral vector. According to particular embodiments, the lentiviral vector contains a 3' LTR in which the 3' LTR enhancer-promoter sequence (i.e. U3 sequence) has been modified (e.g., deleted).

According to some embodiments, the lentiviral vector comprises a polynucleotide sequence which comprises the following elements in a 5' to 3' order:
 (A) a 5' long terminal repeat (5' LTR);
 (B) a promoter (such as the SFFV promoter);
 (C) a polynucleotide sequence encoding a chimeric antigen receptor according to the present invention; and
 (D) a 3' long terminal repeat (3' LTR), preferably 3' self-inactivating LTR.

According to particular embodiments, the lentiviral vector comprises a polynucleotide sequence which comprises the following elements in a 5' to 3' order:
 (a) a 5' long terminal repeat (5' LTR);
 (b) a promoter (such as the SFFV promoter);
 (c) a suicide gene (such as RQR8)
 (d) a polynucleotide sequence encoding a 2A peptide;
 (e) a polynucleotide sequence encoding a chimeric antigen receptor according to the present invention; and
 (f) a 3' long terminal repeat (3' LTR), preferably 3' self-inactivating LTR.

The suicide gene of item (c), the 2A peptide encoding polynucleotide sequence of item (d) and the CAR encoding sequence of item (e) form a single transcription unit operably linked to the promoter of item (b) and are all transcribed under the control of said promoter.

The term "suicide gene" refers to a gene that expresses a product that is fatal to the cell expressing the suicide gene. Activation of the suicide gene causes the cell to kill itself through apoptosis. An example of a suicide gene produce is RQR8 (described e.g., in WO 2013/153391 A1). RQR8 has the general formula St-R1-S1-Q-S2-R2 in which St is a stalk sequence, R1 and R2 are rituximab-binding epitopes; and Q is a QBEndIO-binding epitope. S1 and S2 are optional spacer sequences, such S-(G)n-S where S is serine, G is Glycine and n is a number between 2 and 8. A representative polypeptide sequence of RQR8 is set forth in SEQ ID NO: 60.

According to some embodiments, the 2A peptide is selected from the group consisting of F2A, E2A, T2A and P2A.

Suitable promoters for driving expression of a CAR according to the present invention from a lentiviral vector in immune cells, preferably human T cells, are well know and include the SFFV promoter, the human ubiquitin c (UbC) promoter, MHC class I promoter, MHC class II promoter and β2 microglobulin promoter. Preferably, the promoter is the SFFV promoter.

According to some embodiments, the lentiviral vector is in the form of a lentiviral vector particle, such as an RNA molecule(s) within a complex of lentiviral and other proteins. Typically, lentiviral particle vectors comprise a genome which is composed of two copies of single-stranded RNA. These RNA sequences can be obtained by transcription from a double-stranded DNA sequence inserted into a host cell genome (proviral vector DNA) or can be obtained from the transient expression of plasmid DNA (plasmid vector DNA) in a transduced host cell. Preferably the lentiviral vector particles have the capacity for integration. As such, they contain a functional integrase protein. Non-integrating vector particles have one or more mutations that eliminate most or all of the integrating capacity of the lentiviral vector particles. For, example, a non-integrating vector particle can contain mutation(s) in the integrase encoded by the lentiviral pol gene that cause a reduction in integrating capacity. In contrast, an integrating vector particle comprises a functional integrase protein that does not contain any mutations that eliminate most or all of the integrating capacity of the lentiviral vector particles.

According to other embodiments, the lentiviral vector is in the form of a recombinant DNA molecule, such as a plasmid.

Preferably, the lentiviral vector is based on a human immunodeficiency virus (e.g., HIV-1 or HIV-2), most preferably HIV-1.

Methods of Engineering Immune Cells Endowed with CARs:

The present invention encompasses the method of preparing immune cells for immunotherapy comprising introducing ex-vivo into said immune cells the polynucleotides or vectors encoding one of the anti-GD3 CAR as previously described.

In a preferred embodiment, said polynucleotides are included in lentiviral vectors in view of being stably expressed in the immune cells.

According to certain preferred embodiments, the method comprises introducing ex-vivo into said immune cells a lentiviral vector as described above. The lentiviral vector introduced into said immune cells may, for example, comprise a polynucleotide sequence which comprises the following elements in a 5' to 3' order:
 (a) a 5' long terminal repeat (5' LTR);
 (b) a promoter (such as the SFFV promoter);
 (c) a suicide gene (such as RQR8)
 (d) a polynucleotide sequence encoding a self-cleaving 2A peptide;
 (e) a polynucleotide sequence encoding a chimeric antigen receptor according to the present invention; and
 (f) a 3' long terminal repeat (3' LTR), preferably 3' self-inactivating LTR.

According to further embodiments, said method further comprises the step of genetically modifying said cell to make them more suitable for allogeneic transplantation.

Figure 3:
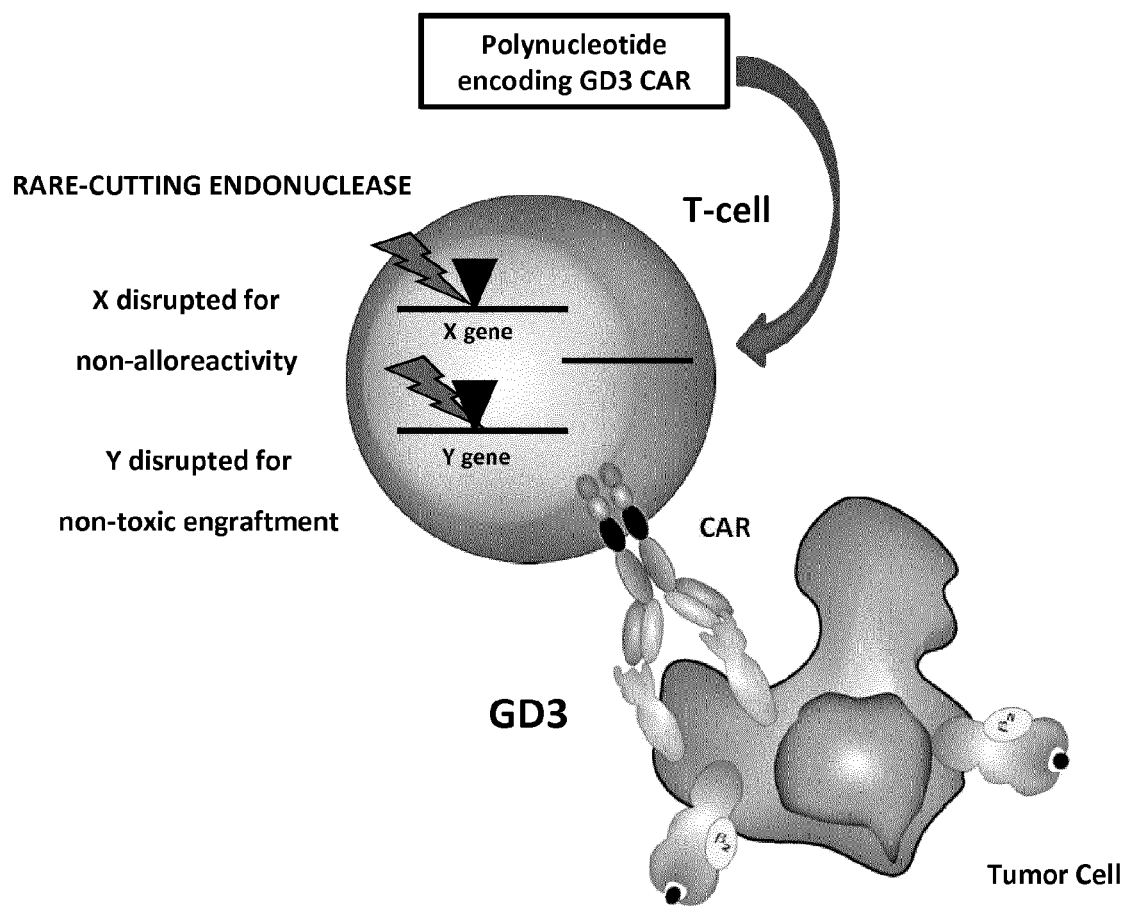
FIG. 3: Schematic representation of an engineered immune cell according to the invention. The engineered immune cell presented in this figure is a T-cell transduced with a retroviral polypeptide encoding CAR. This T-cell is further engineered to allow a better and safer engraftment into the patient, which is optional within the frame of the present invention. X gene may be for instance a gene expressing a component of TCR (TCRalpha or TCRbeta), Y may be a gene involved into the sensitivity of T-cells to immune-suppressive drugs like CD52 (with respect to Campath) or chemotherapy drugs like HPRT (with respect to 6-Thioguanine).

According to a first aspect, the immune cell can be made allogeneic, for instance, by inactivating at least one gene expressing one or more component of T-cell receptor (TCR) as described in WO 2013/176915, which can be combined with the inactivation of a gene encoding or regulating HLA or β2m protein expression. A representation of such TCR disrupted immune cell endowing a chimeric antigen receptor (CAR) is shown in FIG. 3. Accordingly the risk of graft versus host syndrome and graft rejection is significantly reduced.

According to another aspect, the immune cells can be further genetically engineered to improve their resistance to immunosuppressive drugs or chemotherapy treatments, which are used as standard care for treating GD3 positive malignant cells. For instance, CD52 and glucocorticoid receptors (GR), which are drug targets of Campath (alemtuzumab) and glucocorticoids treatments, can be inactivated to make the cells resistant to these treatments and give them a competitive advantage over patient's own T-cells not endowed with specific anti-GD3 CARs. Expression of CD3 gene can also be suppressed or reduced to confer resistance to Teplizumab, which is another immune suppressive drug. Expression of HPRT can also be suppressed or reduced according to the invention to confer resistance to 6-thioguanine, a cytostatic agent commonly used in chemotherapy especially for the treatment of acute lymphoblastic leukemia.

According to further aspect of the invention, the immune cells can be further manipulated to make them more active or limit exhaustion, by inactivating genes encoding proteins that act as "immune checkpoints" that act as regulators of T-cells activation, such as PDCD1 or CTLA-4. Examples of genes, which expression could be reduced or suppressed are indicated in Table 1.

Said plasmid vector can also contain a selection marker which provides for identification and/or selection of cells which received said vector.

Polypeptides may be synthesized in situ in the cell as a result of the introduction of polynucleotides encoding said polypeptides into the cell. Alternatively, said polypeptides could be produced outside the cell and then introduced thereto. Methods for introducing a polynucleotide construct into cells are known in the art and including as non-limiting examples stable transformation methods wherein the polynucleotide construct is integrated into the genome of the cell, transient transformation methods wherein the polynucleotide construct is not integrated into the genome of the cell and virus mediated methods. Said polynucleotides may be introduced into a cell by for example, recombinant viral vectors (e.g. retroviruses, adenoviruses), liposome and the like. For example, transient transformation methods include for example microinjection, electroporation or particle bom-

TABLE 1

List of genes encoding immune checkpoint proteins.

| | Pathway | Genes that can be inactivated In the pathway |
|---|---|---|
| Co-inhibitory receptors | CTLA4 (CD152) | CTLA4, PPP2CA, PPP2CB, PTPN6, PTPN22 |
| | PDCD1 (PD-1, CD279) | PDCD1 |
| | CD223 (lag3) | LAG3 |
| | HAVCR2 (tim3) | HAVCR2 |
| | BTLA(cd272) | BTLA |
| | CD160(by55) | CD160 |
| | IgSF family | TIGIT |
| | | CD96 |
| | | CRTAM |
| | LAIR1(cd305) | LAIR1 |
| | SIGLECs | SIGLEC7 |
| | | SIGLEC9 |
| | CD244(2b4) | CD244 |
| Death receptors | TRAIL | TNFRSF10B, TNFRSF10A, CASP8, CASP10, CASP3, CASP6, CASP7 |
| | FAS | FADD, FAS |
| Cytokine signalling | TGF-beta signaling | TGFBRII, TGFBRI, SMAD2, SMAD3, SMAD4, SMAD10, SKI, SKIL, TGIF1 |
| | IL10 signalling | IL10RA, IL10RB, HMOX2 |
| | IL6 signalling | IL6R, IL6ST |
| Prevention of TCR signalling | | CSK, PAG1 SIT1 |
| Induced Treg | induced Treg | FOXP3 |
| Transcription factors controlling exhaustion | transcription factors controlling exhaustion | PRDM1 (=blimp1, heterozygotes mice control chronic viral infection better than wt or conditional KO) BATF |
| Hypoxia mediated tolerance | iNOS induced guanylated cyclase | GUCY1A2, GUCY1A3, GUCY1B2, GUCY1B3 |

In a preferred embodiment said method of further engineering the immune cells involves introducing into said T cells polynucleotides, in particular mRNAs, encoding specific rare-cutting endonuclease to selectively inactivate the genes, as those mentioned above, by DNA cleavage. In a more preferred embodiment said rare-cutting endonucleases are TALE-nucleases or Cas9 endonuclease. TAL-nucleases have so far proven higher specificity and cleavage efficiency over the other types of rare-cutting endonucleases, making them the endonucleases of choice for producing of the engineered immune cells on a large scale with a constant turn-over.

Delivery Methods

The different methods described above involve introducing CAR into a cell. As non-limiting example, said CAR can be introduced as transgenes encoded by one plasmid vector.

bardment. Said polynucleotides may be included in vectors, more particularly plasmids or virus, in view of being expressed in cells.

Engineered Immune Cells

The present invention also relates to isolated cells or cell lines susceptible to be obtained by said method to engineer cells. In particular said isolated cell comprises at least one CAR as described above. In another embodiment, said isolated cell comprises a population of CARs each one comprising different extracellular ligand binding domains. In particular, said isolated cell comprises exogenous polynucleotide sequence encoding CAR. Genetically modified immune cells of the present invention are activated and proliferate independently of antigen binding mechanisms.

In the scope of the present invention is also encompassed an isolated immune cell, preferably a T-cell obtained according to any one of the methods previously described. Said immune cell refers to a cell of hematopoietic origin functionally involved in the initiation and/or execution of innate and/or adaptative immune response. Said immune cell according to the present invention can be derived from a stem cell. The stem cells can be adult stem cells, non-human embryonic stem cells, more particularly non-human stem cells, cord blood stem cells, progenitor cells, bone marrow stem cells, induced pluripotent stem cells, totipotent stem cells or hematopoietic stem cells. Representative human cells are CD34+ cells. Said isolated cell can also be a dendritic cell, killer dendritic cell, a mast cell, a NK-cell, a B-cell or a T-cell selected from the group consisting of inflammatory T-lymphocytes, cytotoxic T-lymphocytes, regulatory T-lymphocytes or helper T-lymphocytes. In another embodiment, said cell can be derived from the group consisting of CD4+ T-lymphocytes and CD8+ T-lymphocytes. Prior to expansion and genetic modification of the cells of the invention, a source of cells can be obtained from a subject through a variety of non-limiting methods. Cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available and known to those skilled in the art, may be used. In another embodiment, said cell can be derived from a healthy donor, from a patient diagnosed with cancer or from a patient diagnosed with an infection. In another embodiment, said cell is part of a mixed population of cells which present different phenotypic characteristics. In the scope of the present invention is also encompassed a cell line obtained from a transformed T-cell according to the method previously described. Modified cells resistant to an immunosuppressive treatment and susceptible to be obtained by the previous method are encompassed in the scope of the present invention.

As a preferred embodiment, the present invention provides T-cells or a population of T-cells endowed with an anti-GD3 CAR as described above, that do not express functional TCR and that a reactive towards GD3 positive cells, for their allogeneic transplantation into patients. For instance, as an example, the TRAC locus of SEQ ID NO. 43 can be inactivated by using the pair of TALENs of SEQ ID NO. 44 and 45.

Activation and Expansion of T Cells

Whether prior to or after genetic modification of the T cells, even if the genetically modified immune cells of the present invention are activated and proliferate independently of antigen binding mechanisms, the immune cells, particularly T-cells of the present invention can be further activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. T cells can be expanded in vitro or in vivo.

Generally, the T cells of the invention are expanded by contact with an agent that stimulates a CD3 TCR complex and a co-stimulatory molecule on the surface of the T cells to create an activation signal for the T-cell. For example, chemicals such as calcium ionophore A23187, phorbol 12-myristate 13-acetate (PMA), or mitogenic lectins like phytohemagglutinin (PHA) can be used to create an activation signal for the T-cell.

As non-limiting examples, T cell populations may be stimulated in vitro such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. Conditions appropriate for T cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-g, 1L-4, 1L-7, GM-CSF, -10, -2, 1L-15, TGFp, and TNF- or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, A1M-V, DMEM, MEM, a-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% CO2). T cells that have been exposed to varied stimulation times may exhibit different characteristics In another particular embodiment, said cells can be expanded by co-culturing with tissue or cells. Said cells can also be expanded in vivo, for example in the subject's blood after administrating said cell into the subject.

Therapeutic Applications

In another embodiment, isolated cell obtained by the different methods or cell line derived from said isolated cell as previously described can be used as a medicament.

In another embodiment, said medicament can be used for treating cancer, particularly for the treatment of solid tumors such as melanomas, neuroblastomas, gliomas or carcinomas such as lung, breast, colon, prostate or ovary tumors in a patient in need thereof.

In another embodiment, said isolated cell according to the invention or cell line derived from said isolated cell can be used in the manufacture of a medicament for treatment of a cancer in a patient in need thereof.

In another aspect, the present invention relies on methods for treating patients in need thereof, said method comprising at least one of the following steps:

(a) providing an immune-cell obtainable by any one of the methods previously described;
(b) Administrating said transformed immune cells to said patient, On one embodiment, said T cells of the invention can undergo robust in vivo T cell expansion and can persist for an extended amount of time.

Said treatment can be ameliorating, curative or prophylactic. It may be either part of an autologous immunotherapy or part of an allogenic immunotherapy treatment. By autologous, it is meant that cells, cell line or population of cells used for treating patients are originating from said patient or from a Human Leucocyte Antigen (HLA) compatible donor. By allogeneic is meant that the cells or population of cells used for treating patients are not originating from said patient but from a donor.

Cells that can be used with the disclosed methods are described in the previous section. Said treatment can be used to treat patients diagnosed wherein a pre-malignant or malignant cancer condition characterized by GD3-expressing cells, especially by an overabundance of GD3-expressing cells. Such conditions are found in solid cancers, such as melanomas, gliomas, neuroblastomas or carcinomas.

In another embodiment, said isolated cell according to the invention or cell line derived from said isolated cell can be used for the treatment of liquid tumors, and preferably of T-cell acute lymphoblastic leukemia.

Adult tumors/cancers and pediatric tumors/cancers are also included.

The treatment with the engineered immune cells according to the invention may be in combination with one or more therapies against cancer selected from the group of antibodies therapy, chemotherapy, cytokines therapy, dendritic cell therapy, gene therapy, hormone therapy, laser light therapy and radiation therapy.

According to a preferred embodiment of the invention, said treatment can be administrated into patients undergoing an immunosuppressive treatment. Indeed, the present invention preferably relies on cells or population of cells, which have been made resistant to at least one immunosuppressive agent due to the inactivation of a gene encoding a receptor for such immunosuppressive agent. In this aspect, the immunosuppressive treatment should help the selection and expansion of the T-cells according to the invention within the patient.

The administration of the cells or population of cells according to the present invention may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. The cells or population of cells can be administrated in one or more doses. In another embodiment, said effective amount of cells are administrated as a single dose. In another embodiment, said effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, said effective amount of cells or composition comprising those cells are administrated parenterally. Said administration can be an intravenous administration. Said administration can be directly done by injection within a tumor.

In certain embodiments of the present invention, cells are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or nataliziimab treatment for MS patients or efaliztimab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycoplienolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Henderson, Naya et al. 1991; Liu, Albers et al. 1992; Bierer, Hollander et al. 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH, In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

Preferred indications for the therapeutic use of the anti GD3 CAR according to the present inventions are melanoma, neuroblastoma, Glioma, breast carcinoma, ovarian epithelial tumors, neuroendocrine tumors and T-cell acute lymphoblastic leukemia.

Other Definitions

Amino acid residues in a polypeptide sequence are designated herein according to the one-letter code, in which, for example, Q means Gln or Glutamine residue, R means Arg or Arginine residue and D means Asp or Aspartic acid residue.

Amino acid substitution means the replacement of one amino acid residue with another, for instance the replacement of an Arginine residue with a Glutamine residue in a peptide sequence is an amino acid substitution.

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

"As used herein, "nucleic acid" or "polynucleotides" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Nucleic acids can be either single stranded or double stranded.

By chimeric antigen receptor (CAR) is intended molecules that combine a binding domain against a component present on the target cell, for example an antibody-based specificity for a desired antigen (e.g., tumor antigen) with a T cell receptor-activating intracellular domain to generate a chimeric protein that exhibits a specific anti-target cellular immune activity. Generally, CAR consists of an extracellular single chain antibody (scFvFc), fused to the intracellular signaling domain of the T cell antigen receptor complex zeta chain (scFvFc:ζ) and have the ability, when expressed in T cells, to redirect antigen recognition based on the monoclonal antibody's specificity. CAR may sometimes comprise multiple transmembrane polypeptides (multi-chain CARs) as described in WO2014039523. One example of CAR used in the present invention is a CAR directing against GD3 antigen and can comprise as non-limiting example the amino acid sequences: SEQ ID NO: 19 to 30.

The term "endonuclease" refers to any wild-type or variant enzyme capable of catalyzing the hydrolysis (cleavage) of bonds between nucleic acids within a DNA or RNA molecule, preferably a DNA molecule. Endonucleases do not cleave the DNA or RNA molecule irrespective of its sequence, but recognize and cleave the DNA or RNA molecule at specific polynucleotide sequences, further referred to as "target sequences" or "target sites". Endonucleases can be classified as rare-cutting endonucleases when having typically a polynucleotide recognition site greater than 12 base pairs (bp) in length, more preferably of 14-55 bp. Rare-cutting endonucleases significantly increase HR by inducing DNA double-strand breaks (DSBs) at a defined locus (Perrin, Buckle et al. 1993; Rouet, Smih et al. 1994; Choulika, Perrin et al. 1995; Pingoud and Silva 2007). Rare-cutting endonucleases can for example be a homing endonuclease (Paques and Duchateau 2007), a chimeric Zinc-Finger nuclease (ZFN) resulting from the fusion of engineered zinc-finger domains with the catalytic domain of a restriction enzyme such as FokI (Porteus and Carroll 2005), a Cas9 endonuclease from CRISPR system (Gasiunas, Barrangou et al. 2012; Jinek, Chylinski et al. 2012; Cong, Ran et al. 2013; Mali, Yang et al. 2013) or a chemical endonuclease (Eisenschmidt, Lanio et al. 2005; Arimondo, Thomas et al. 2006). In chemical endonucleases, a chemical or peptidic cleaver is conjugated either to a polymer of nucleic acids or to another DNA recognizing a specific target sequence, thereby targeting the cleavage activity to a specific sequence. Chemical endonucleases also encompass synthetic nucleases like conjugates of orthophenanthroline, a DNA cleaving molecule, and triplex-forming oligonucleotides (TFOs), known to bind specific DNA sequences (Kalish and Glazer 2005). Such chemical endonucleases are comprised in the term "endonuclease" according to the present invention.

By a "TALE-nuclease" (TALEN) is intended a fusion protein consisting of a nucleic acid-binding domain typically derived from a Transcription Activator Like Effector (TALE) and one nuclease catalytic domain to cleave a nucleic acid target sequence. The catalytic domain is preferably a nuclease domain and more preferably a domain having endonuclease activity, like for instance I-TevI, ColE7, NucA and Fok-I. In a particular embodiment, the TALE domain can be fused to a meganuclease like for instance I-CreI and I-OnuI or functional variant thereof. In a more preferred embodiment, said nuclease is a monomeric TALE-Nuclease. A monomeric TALE-Nuclease is a TALE-Nuclease that does not require dimerization for specific recognition and cleavage, such as the fusions of engineered TAL repeats with the catalytic domain of I-TevI described in WO2012138927. Transcription Activator like Effector (TALE) are proteins from the bacterial species *Xanthomonas* comprise a plurality of repeated sequences, each repeat comprising di-residues in position 12 and 13 (RVD) that are specific to each nucleotide base of the nucleic acid targeted sequence. Binding domains with similar modular base-per-base nucleic acid binding properties (MBBBD) can also be derived from new modular proteins recently discovered by the applicant in a different bacterial species. The new modular proteins have the advantage of displaying more sequence variability than TAL repeats. Preferably, RVDs associated with recognition of the different nucleotides are HD for recognizing C, NG for recognizing T, NI for recognizing A, NN for recognizing G or A, NS for recognizing A, C, G or T, HG for recognizing T, IG for recognizing T, NK for recognizing G, HA for recognizing C, ND for recognizing C, HI for recognizing C, HN for recognizing G, NA for recognizing G, SN for recognizing G or A and YG for recognizing T, TL for recognizing A, VT for recognizing A or G and SW for recognizing A. In another embodiment, critical amino acids 12 and 13 can be mutated towards other amino acid residues in order to modulate their specificity towards nucleotides A, T, C and G and in particular to enhance this specificity. TALE-nuclease have been already described and used to stimulate gene targeting and gene modifications (Boch, Scholze et al. 2009; Moscou and Bogdanove 2009; Christian, Cermak et al. 2010; Li, Huang et al. 2011). Custom-made TAL-nucleases are commercially available under the trade name TALEN™ (Cellectis, 8 rue de la Croix Jarry, 75013 Paris, France).

The rare-cutting endonuclease according to the present invention can also be a Cas9 endonuclease. Recently, a new genome engineering tool has been developed based on the RNA-guided Cas9 nuclease (Gasiunas, Barrangou et al. 2012; Jinek, Chylinski et al. 2012; Cong, Ran et al. 2013; Mali, Yang et al. 2013) from the type II prokaryotic CRISPR (Clustered Regularly Interspaced Short palindromic Repeats) adaptive immune system (see for review (Sorek, Lawrence et al. 2013)). The CRISPR Associated (Cas) system was first discovered in bacteria and functions as a defense against foreign DNA, either viral or plasmid. CRISPR-mediated genome engineering first proceeds by the selection of target sequence often flanked by a short sequence motif, referred as the protospacer adjacent motif (PAM). Following target sequence selection, a specific crRNA, complementary to this target sequence is engineered. Trans-activating crRNA (tracrRNA) required in the CRISPR type II systems paired to the crRNA and bound to the provided Cas9 protein. Cas9 acts as a molecular anchor facilitating the base pairing of tracRNA with cRNA (Deltcheva, Chylinski et al. 2011). In this ternary complex, the dual tracrRNA:crRNA structure acts as guide RNA that directs the endonuclease Cas9 to the cognate target sequence. Target recognition by the Cas9-tracrRNA:crRNA complex is initiated by scanning the target sequence for homology between the target sequence and the crRNA. In addition to the target sequence-crRNA complementarity, DNA targeting requires the presence of a short motif adjacent to the protospacer (protospacer adjacent motif—PAM). Following pairing between the dual-RNA and the target sequence, Cas9 subsequently introduces a blunt double strand break 3 bases upstream of the PAM motif (Garneau, Dupuis et al. 2010).

Rare-cutting endonuclease can be a homing endonuclease, also known under the name of meganuclease. Such homing endonucleases are well-known to the art (Stoddard 2005). Homing endonucleases recognize a DNA target sequence and generate a single- or double-strand break. Homing endonucleases are highly specific, recognizing DNA target sites ranging from 12 to 45 base pairs (bp) in length, usually ranging from 14 to 40 bp in length. The homing endonuclease according to the invention may for example correspond to a LAGLIDADG endonuclease, to a HNH endonuclease, or to a GIY-YIG endonuclease. Preferred homing endonuclease according to the present invention can be an I-CreI variant.

By "delivery vector" or "delivery vectors" is intended any delivery vector which can be used in the present invention to put into cell contact (i.e "contacting") or deliver inside cells or subcellular compartments (i.e "introducing") agents/chemicals and molecules (proteins or nucleic acids) needed in the present invention. It includes, but is not limited to liposomal delivery vectors, viral delivery vectors, drug delivery vectors, chemical carriers, polymeric carriers, lipoplexes, polyplexes, dendrimers, microbubbles (ultrasound contrast agents), nanoparticles, emulsions or other appropriate transfer vectors. By "delivery vector" or "delivery vectors" is also intended delivery methods to perform transfection.

The terms "vector" or "vectors" refer to a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non-chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

Viral vectors include retrovirus, adenovirus, parvovirus (e. g. adenoassociated viruses), coronavirus, negative strand RNA viruses such as orthomyxovirus (e. g., influenza virus), rhabdovirus (e. g., rabies and vesicular stomatitis virus), paramyxovirus (e. g. measles and Sendai), positive strand RNA viruses such as picornavirus and alphavirus, and double-stranded DNA viruses including adenovirus, herpesvirus (e. g., Herpes Simplex virus types 1 and 2, Epstein-Barr virus, cytomega-lovirus), and poxvirus (e. g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

By "lentiviral vector" is meant HIV-Based lentiviral vectors that are very promising for gene delivery because of their relatively large packaging capacity, reduced immunogenicity and their ability to stably transduce with high efficiency a large range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration in the DNA of infected cells. By "integrative lentiviral vectors (or LV)", is meant such vectors as nonlimiting example, that are able to integrate the genome of a target cell. At the opposite by "non-integrative lentiviral vectors (or NILV)" is meant efficient gene delivery vectors that do not integrate the genome of a target cell through the action of the virus integrase.

Delivery vectors and vectors can be associated or combined with any cellular permeabilization techniques such as sonoporation or electroporation or derivatives of these techniques.

By cell or cells is intended any eukaryotic living cells, primary cells and cell lines derived from these organisms for in vitro cultures.

By "primary cell" or "primary cells" are intended cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines.

As non-limiting examples cell lines can be selected from the group consisting of CHO-K1 cells; HEK293 cells; Caco2 cells; U2-OS cells; NIH 3T3 cells; NSO cells; SP2 cells; CHO-S cells; DG44 cells; K-562 cells, U-937 cells; MRC5 cells; IMR90 cells; Jurkat cells; HepG2 cells; HeLa cells; HT-1080 cells; HCT-116 cells; Hu-h7 cells; Huvec cells; Molt 4 cells.

All these cell lines can be modified by the method of the present invention to provide cell line models to produce, express, quantify, detect, study a gene or a protein of interest; these models can also be used to screen biologically active molecules of interest in research and production and various fields such as chemical, biofuels, therapeutics and agronomy as non-limiting examples.

by "mutation" is intended the substitution, deletion, insertion of up to one, two, three, four, five, six, seven, eight, nine, ten, eleven, twelve, thirteen, fourteen, fifteen, twenty, twenty five, thirty, forty, fifty, or more nucleotides/amino acids in a polynucleotide (cDNA, gene) or a polypeptide sequence. The mutation can affect the coding sequence of a gene or its regulatory sequence. It may also affect the structure of the genomic sequence or the structure/stability of the encoded mRNA.

by "variant(s)", it is intended a repeat variant, a variant, a DNA binding variant, a TALE-nuclease variant, a polypeptide variant obtained by mutation or replacement of at least one residue in the amino acid sequence of the parent molecule.

by "functional variant" is intended a catalytically active mutant of a protein or a protein domain; such mutant may have the same activity compared to its parent protein or protein domain or additional properties, or higher or lower activity.

"identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity of similarity to the amino acid sequences disclosed herein are contemplated and encompassed by this disclosure. The polynucleotide sequences of similar polypeptides are deduced using the genetic code and may be obtained by conventional means, in particular by reverse translating its amino acid sequence using the genetic code.

"signal-transducing domain" or "co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory igand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-IBB, OX40, CD30, CD40, PD-1, ICOS, lymphocyte function-associated antigen-1 (LFA-1), CD2, CD7, LTGHT, NKG2C, B7-H3, a ligand that specifically binds with CD83.

A "co-stimulatory molecule" refers to the cognate binding partner on a Tcell that specifically binds with a co-stimulatory ligand, thereby mediating a co-stimulatory response by the cell, such as, but not limited to proliferation. Co-stimulatory molecules include, but are not limited to an MHC class I molecule, BTLA and Toll ligand receptor.

A "co-stimulatory signal" as used herein refers to a signal, which in combination with primary signal, such as TCR/CD3 ligation, leads to T cell proliferation and/or upregulation or downregulation of key molecules.

The term "extracellular ligand-binding domain" as used herein is defined as an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state. Thus examples of cell surface markers that may act as ligands include those associated with viral, bacterial and parasitic infections, autoimmune disease and cancer cells.

The term "subject" or "patient" as used herein includes all members of the animal kingdom including non-human primates and humans.

The above written description of the invention provides a manner and process of making and using it such that any person skilled in this art is enabled to make and use the same, this enablement being provided in particular for the subject matter of the appended claims, which make up a part of the original description.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain spe-

EXAMPLES

Example 1. Selection of GD3-Positive and -Negative Cell Lines

Materials and Methods
Primary Cells

Peripheral blood mononuclear cells were isolated by density gradient centrifugation from buffy coats from healthy volunteer donors (Etablissement Français du Sang). T lymphocytes were then purified using the EasySep human T cell enrichment kit (Stemcell Technologies), and activated with Dynabeads Human T-Activator CD3/CD28 (Life Technologies) in X-vivo 15 medium (Lonza) supplemented with 20 ng/ml IL-2 (Miltenyi) and 5% human AB serum (Seralab).

Cell Lines

The SK-MEL-28, A2058, G-361, MeWo and MCF-7 cell lines were obtained from the American Type Culture Collection. MeWo and SK-MEL-28 cells were cultured in EMEM supplemented with 10% heat-inactivated FCS, 2 mmol/L L-glutamine and 100 units/ml penicillin, and 100 µg/mL streptomycin. A2058 cells were cultured in DMEM supplemented with 10% heat-inactivated FCS, 2 mmol/L L-glutamine and 100 units/ml penicillin, and 100 µg/mL streptomycin. G-361 cells were cultured in McCoy's 5a supplemented with 10% heat-inactivated FCS, 2 mmol/L L-glutamine and 100 units/ml penicillin, and 100 µg/mL streptomycin. MCF-7 cells were cultured in DMEM supplemented with 10% heat-inactivated FCS, 2 mmol/L L-glutamine and 100 units/ml penicillin, and 100 µg/mL streptomycin and 0.01 mg/ml human insulin.

Quantification of GD3 Cell Surface Expression

The number of GD3 surface molecules on different human cells was determined by saturation binding using the monoclonal anti-GD3 R24 (ab11779—Abcam) and the Dako QiFIKIT according to the manufacturer's instructions.

Results

To identify cell lines expressing different cell surface expression levels of GD3, 7 human cell lines were analysed by flow cytometry using the Qifikit (Dako) and the anti-human GD3 mAb clone R24 (see materials and methods). As shown in the following Table 2, four of these cell lines had previously been described in the literature to be positive for GD3.

TABLE 2

Selected Cell lines for the expression of GD3

| cell line | description | cell type |
|---|---|---|
| CHP-134 | adherent | neuroblastoma |
| G-361 | adherent | malignant melanoma |
| MeWo | adherent | malignant melanoma |
| SK-MEL-28 | adherent | malignant melanoma |

Figure 2:
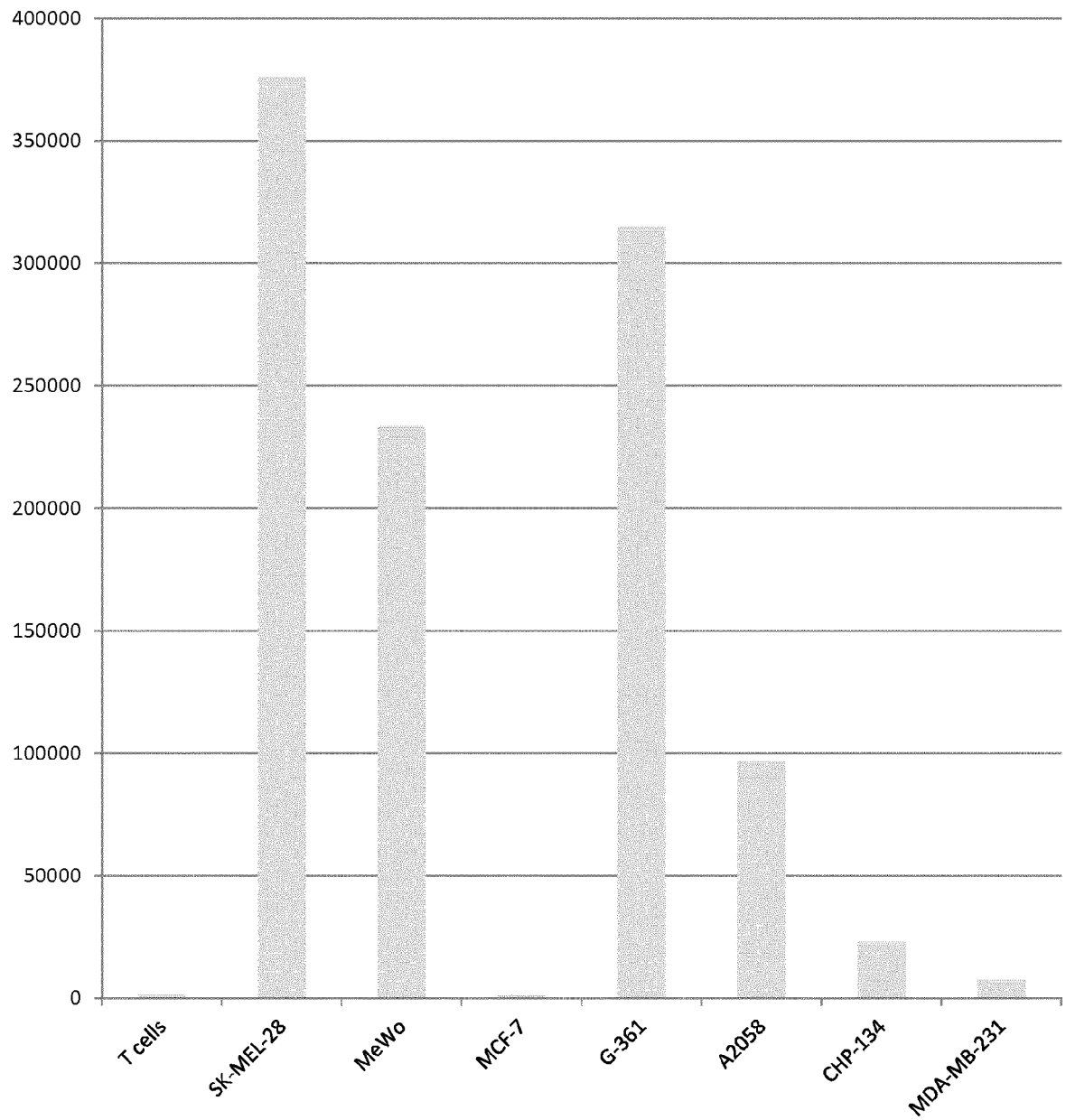
FIG. 2: Analysis by flow cytometry using the Qifikit (Dako) to identify cells expressing GD3 surface molecules: 7 different human cell lines were tested and amongst them 4 (CHP-134, G-361, MeWo and SK-MEL-28) had previously been described in the literature to be positive for GD3.

Our flow cytometry results indicate that SK-MEL-28, G-361 and MeWo cells expressed the highest levels of GD3 surface expression. Lower levels were detected on A2058, CHP-134 and MDA-MB-231 cells (FIG. 2). MCF-7 cells and T cells expressed only negligible amount of GD3 as compared to SK-MEL-28, G361, Mewo, and A2058 cells (FIG. 2).

From these experiments, 5 cell lines were selected to screen the activity of anti-GD3 scCARs: SK-MEL-28, G-361, MeWo, and A2058 cells that we consider as GD3 positive, and MCF-7 cells that we consider as GD3 negative.

Example 2: Generation of Anti-GD3 scCARs

Figure 4:
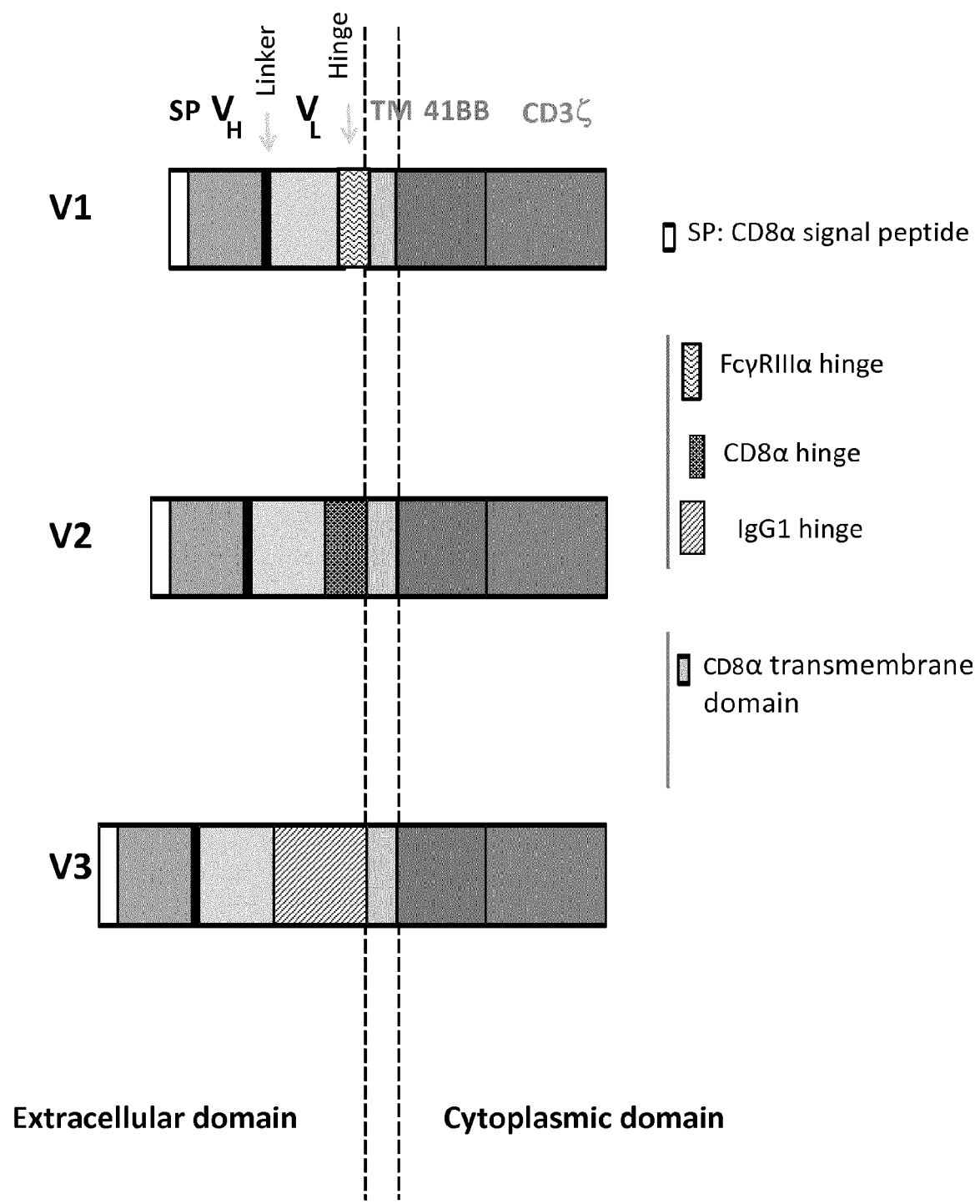
FIG. 4: Schematic representation of the different CAR Architecture (V1 to V3). In these experiments were designed twelve 2nd generation anti-GD3 specific scCARs resulting from the fusion of the following building blocks: —one scFv from murine (MB3.6 or KM641 or BW2121 or R24) origin; —one spacer (human FcγRIIIα hinge or human CD8α hinge or human IgG1 hinge CH2 CH3); —the transmembrane domain of human CD8α; —the costimulatory domain of human 41BB and —the activation domain of human CD3ζ.

In these experiments were designed twelve 2nd generation anti-GD3 specific scCARs resulting from the fusion of the building blocks as depicted in the FIG. 4.

- one scFv from murine (MB3.6 or KM641 or BW2121 or R24) origin
- one spacer (human FcεRIIIα hinge or human CD8α hinge or human IgG1 hinge CH2 CH3)
- the transmembrane domain of human CD8α
- the costimulatory domain of human 41BB
- the activation domain of human CD3ζ

Different scFv were used in the scCARs to generate receptors of different binding affinities and different epitope specificities.

Three spacers of different length (16 aa, 45 aa and 231 aa) were used in the scCARs to try to optimize scCAR engagement by both proximal and distal epitopes of GD3 (Guest et al., 2005; Hudecek et al., 2013).

Materials and Methods
Synthesis of DNA Encoding scCARs

The DNA encoding the scCARs was synthesized by GenScript.

Construction of In Vitro Transcription mRNA Vectors for scCARs

The DNA encoding the scCARs was cloned in the plasmid pCLS9632 between the T7 promoter and the BGH poly A.

Anti-GD3 scCARs: Components and Constructions

All the components and the scFv used for the constructions of the anti-GD3 CARs are presented in the following Table 2 and Table 3.

The following Table 3 to Table 7 correspond to the configurations of the versions v1 to v3 respectively, depending of the hinge and the linker used.

TABLE 3

Sequence of the different CAR components

| Functional domains | SEQ ID # | Raw amino acid sequence |
|---|---|---|
| CD8α signal peptide | SEQ ID NO. 1 | MALPVTALLLPLALLLHAARP |
| Alternative signal peptide (as exemple, not used in the experiments) | SEQ ID NO. 2 | METDTLLLWVLLLWVPGSTG |

TABLE 3-continued

Sequence of the different CAR components

| Functional domains | SEQ ID # | Raw amino acid sequence |
|---|---|---|
| FcεRIIIα hinge | SEQ ID NO. 3 | GLAVSTISSFFPPGYQ |
| CD8α hinge | SEQ ID NO. 4 | TTTPAPRPPTPAPTIASQPLSLRPEACRPAAGGA VHTRGLDFACD |
| IgG1 hinge | SEQ ID NO. 5 | EPKSPDKTHTCPPCPAPPVAGPSVFLFPPKPKDT LMIARTPEVTCVVVDVSHEDPEVKFNWYVDGV EVHNAKTKPREEQYNSTYRVVSVLTVLHQDWL NGKEYKCKVSNKALPAPIEKTISKAKGQPREPQV YTLPPSRDELTKNQVSLTCLVKGFYPSDIAVEWE SNGQPENNYKTTPPVLDSDGSFFLYSKLTVDKSR WQQGNVFSCSVMHEALHNHYTQKSLSLSPGK |
| CD8α transmembrane domain | SEQ ID NO. 6 | IYIWAPLAGTCGVLLLSLVITLYC |
| 41BB transmembrane domain (as exemple, not used in the experiments) | SEQ ID NO. 7 | IISFFLALTSTALLFLLFFLTLRFSVV |
| 41BB intracellular domain | SEQ ID NO. 8 | KRGRKKLLYIFKQPFMRPVQTTQEEDGCSCRFPE EEEGGCEL |
| CD3 ζ intracellular domain | SEQ ID NO. 9 | RVKFSRSADAPAYQQGQNQLYNELNLGRREEY DVLDKRRGRDPEMGGKPRRKNPQEGLYNELQK DKMAEAYSEIGMKGERRRGKGHDGLYQGLSTA TKDTYDALHMQALPPR |
| G4Sx3 linker | SEQ ID NO. 10 | GGGGSGGGGSGGGGS |

TABLE 4

Sequence of the VH and VL chains of the scFvs and of their corresponding CDRs

| ScFv sequences | SEQ ID # | Raw amino acid sequence |
|---|---|---|
| R24 heavy chain variable region | SEQ ID NO. 11 | DVQLVESGGGLVQPGGSRKLSCAASGFTFSNFGMHWV RQAPEKGLEWVAYISSGGSSINYADTVKGRFTISRDNPK NTLFLQMTSLRSEDTAIYYCTRGGTGTRSLYYFDYWGQ GATLIV |
|  | SEQ ID NO. 36 | NFGMH (CDR1) |
|  | SEQ ID NO. 37 | YISSGGSSINYADTV (CDR2) |
|  | SEQ ID NO. 38 | GGTGTRSLYYFDY (CDR3) |
| R24 light chain variable region | SEQ ID NO. 12 | DIQMTQITSSLSVSLGDRVIISCRASQDIGNFLNWYQQK PDGSLKLLIYYTSRLQSGVPSRFSGWGSGTDYSLTISNLEE EDIATFFCQQGKTLPYTFGGGTKLEIK |
|  | SEQ ID NO. 39 | RASQDIGNFLN (CDR1) |
|  | SEQ ID NO. 40 | YTSRLQS (CDR2) |
|  | SEQ ID NO. 41 | QQGKTLPYT (CDR3) |
| MB3.6 heavy chain variable region | SEQ ID NO. 13 | EVVVESGGGFVKPGGSLKLSCAAAGFTFSRYAMSWVR QTPEKRLEWVATISSGGSHTYYPDSVKGRFTISRDNAKN TLYLQMSSLRSEDTAIYYCARPGYDRGAWFFDVWGAG TTVTVSS |
|  | SEQ ID NO. 42 | GFTFSRYA (CDR1) |
|  | SEQ ID NO. 43 | ISSGGSHT (CDR2) |
|  | SEQ ID NO. 44 | ARPGYDRGAWFFDV (CDR3) |
| MB3.6 light chain variable region | SEQ ID NO. 14 | DIVLTQSPATLSVTPGDSVSLSCRASQIISNNLHWYQQKS HESPRLLIKYASQSISGIPSRFSGSGSGTDFTLSINSVETED FGMYFCQQSNSWPLTFGSGTKLEIKR |
|  | SEQ ID NO. 45 | QIISNN (CDR1) |
|  | SEQ ID NO. 46 | YAS (CDR2) |
|  | SEQ ID NO. 47 | QQSNSWPLT (CDR3) |
| KM641 heavy chain variable region | SEQ ID NO. 15 | EVTLVESGGDFVKPGGSLKVSCAASGFAFSHYAMSWVR QTPAKRLEWVAYISSGGSGTYYSDSVKGRFTISRDNAKN TLYLQMRSLRSEDSAMYFCTRVKLGTYYFDSWGQGTTL TVSS |
|  | SEQ ID NO. 48 | HYAMS (CDR1) |
|  | SEQ ID NO. 49 | YISSGGSGTYYSDSVKG (CDR2) |
|  | SEQ ID NO. 50 | VKLGTYYFDS (CDR3) |

TABLE 4-continued

Sequence of the VH and VL chains of the scFvs and of their corresponding CDRs

| ScFv sequences | SEQ ID # | Raw amino acid sequence |
|---|---|---|
| KM641 light chain variable region | SEQ ID NO. 16 | DIQMTQTASSLPASLGDRVTISCSASQDISNYLNWYQQ KPDGTVKLLIFYSSNLHSGVPSRFSGGGSGTDYSLTISNLE PEDIATYFCHQYSKLPWTFGGGTKLEIK |
|  | SEQ ID NO. 51 | SASQDISNYLN (CDR1) |
|  | SEQ ID NO. 52 | YSSNLHS (CDR2) |
|  | SEQ ID NO. 53 | HQYSKLPWT (CDR3) |
| BW2121 heavy chain variable region | SEQ ID NO. 17 | QVQLQQSGGGLVKPGGSLTLSCAASRFTFSTYAMSWV RQTPAKRLEWVAYISSGGASTYYRDSVKGRFTISRDNAK NTLYLQMSSLRSEDTAMYYCARGGSRYAMDYWGQGT TVTVSS |
|  | SEQ ID NO. 54 | RFTFSTYA (CDR1) |
|  | SEQ ID NO. 55 | ISSGGAST (CDR2) |
|  | SEQ ID NO. 56 | ARGGSRYAMDY (CDR3) |
| BW2121 light chain variable region | SEQ ID NO. 18 | DIQLTQSPAILSVSPGERVSFSCWASQSIGTSIHWYQQR TNGSPRLLIKYSSESISGIPSRFSGSGSGTDFTLSINSLESED IADYYCQQTYSWPFTFGSGTKLEI |
|  | SEQ ID NO. 57 | QSIGTS (CDR1) |
|  | SEQ ID NO. 58 | YSS (CDR2) |
|  | SEQ ID NO. 59 | QQTYSWPFT (CDR3) |

TABLE 5

CARs of structure V-1

| SEQ ID NO. | signal peptide (optional) | VH | VL | FcεRIIIα hinge | CD8α TM | 41BB -IC | CD3ζ IC |
|---|---|---|---|---|---|---|---|
| (SEQ ID NO. 19) | SEQ ID NO. 1 | SEQ ID NO. 11 | SEQ ID NO. 12 | SEQ ID NO. 3 | SEQ ID NO. 6 | SEQ ID NO. 8 | SEQ ID NO. 9 |
| (SEQ ID NO. 22) | SEQ ID NO. 1 | SEQ ID NO. 13 | SEQ ID NO. 14 | SEQ ID NO. 3 | SEQ ID NO. 6 | SEQ ID NO. 8 | SEQ ID NO. 9 |
| (SEQ ID NO. 25) | SEQ ID NO. 1 | SEQ ID NO. 15 | SEQ ID NO. 16 | SEQ ID NO. 3 | SEQ ID NO. 6 | SEQ ID NO. 8 | SEQ ID NO. 9 |
| (SEQ ID NO. 28) | SEQ ID NO. 1 | SEQ ID NO. 17 | SEQ ID NO. 18 | SEQ ID NO. 3 | SEQ ID NO. 6 | SEQ ID NO. 8 | SEQ ID NO. 9 |

TABLE 6

CAR of structure V2

| SEQ ID NO | signal peptide (optional) | VH | VL | CD8α hinge | CD8α TM | 41BB -IC | CD3ζ IC |
|---|---|---|---|---|---|---|---|
| (SEQ ID NO. 20) | SEQ ID NO. 1 | SEQ ID NO. 11 | SEQ ID NO. 12 | SEQ ID NO. 4 | SEQ ID NO. 6 | SEQ ID NO. 8 | SEQ ID NO. 9 |
| (SEQ ID NO. 23) | SEQ ID NO. 1 | SEQ ID NO. 13 | SEQ ID NO. 14 | SEQ ID NO. 4 | SEQ ID NO. 6 | SEQ ID NO. 8 | SEQ ID NO. 9 |
| (SEQ ID NO. 26) | SEQ ID NO. 1 | SEQ ID NO. 15 | SEQ ID NO. 16 | SEQ ID NO. 4 | SEQ ID NO. 6 | SEQ ID NO. 8 | SEQ ID NO. 9 |
| (SEQ ID NO. 29) | SEQ ID NO. 1 | SEQ ID NO. 17 | SEQ ID NO. 18 | SEQ ID NO. 4 | SEQ ID NO. 6 | SEQ ID NO. 8 | SEQ ID NO. 9 |

TABLE 7

| | CAR of structure V-3 | | | | | | |
|---|---|---|---|---|---|---|---|
| | CAR Structure | | | | | | |
| SEQ ID NO. | signal peptide (optional) | VH | VL | IgG1 hinge | CD8α TM | 41BB -IC | CD3ζ IC |
| (SEQ ID NO. 21) | SEQ ID NO. 1 | SEQ ID NO. 11 | SEQ ID NO. 12 | SEQ ID NO. 5 | SEQ ID NO. 6 | SEQ ID NO. 8 | SEQ ID NO. 9 |
| (SEQ ID NO. 24) | SEQ ID NO. 1 | SEQ ID NO. 13 | SEQ ID NO. 14 | SEQ ID NO. 5 | SEQ ID NO. 6 | SEQ ID NO. 8 | SEQ ID NO. 9 |
| (SEQ ID NO. 27) | SEQ ID NO. 1 | SEQ ID NO. 15 | SEQ ID NO. 16 | SEQ ID NO. 5 | SEQ ID NO. 6 | SEQ ID NO. 8 | SEQ ID NO. 9 |
| (SEQ ID NO. 30) | SEQ ID NO. 1 | SEQ ID NO. 17 | SEQ ID NO. 18 | SEQ ID NO. 5 | SEQ ID NO. 6 | SEQ ID NO. 8 | SEQ ID NO. 9 |

The amino acid of the anti-GD3 scCARs are presented in the following SEQ ID NO. 19 to 30.
Anti-GD3 CAR Polypeptide Sequences Tested in the Present Invention
Framed sequences correspond to preferred VH and VL sequences.

```
R24 v1
                                                                (SEQ ID NO. 19)
MALPVTALLLPLALLLHAARP DVQLVESGGGLVQPGGSRKLSCAASGFTFSNFGMHWVRQAPEKGLEWVAYISSG

GSSINYADTVKGRFTISRDNPKNTLFLQMTSLRSEDTAIYYCTRGGTGTRSLYYFDYWGQGATLIV GGGGSGGGGS

GGGGS DIQMTQITSSLSVSLGDRVIISCRASQDIGNFLNWYQQKPDGSLKLLIYYTSRLQSGVPSRFSGWGSGTDYS

LTISNLEEEDIATFFCQQGKTLPYTFGGGTKLEIK GLAVSTISSFFPPGYQIYIWAPLAGTCGVLLLSLVITLYCKRGRKKL

LYIFKQPFMRPVQTTQEEDGCSCRFPEEEEGGCELRVKFSRSADAPAYQQGQNQLYNELNLGRREEYDVLDKRRGR

DPEMGGKPRRKNPQEGLYNELQKDKMAEAYSEIGMKGERRRGKGHDGLYQGLSTATKDTYDALHMQALPPR

R24 v2
                                                                (SEQ ID NO. 20)
MALPVTALLLPLALLLHAARP DVQLVESGGGLVQPGGSRKLSCAASGFTFSNFGMHWVRQAPEKGLEWVAYISSG

GSSINYADTVKGRFTISRDNPKNTLFLQMTSLRSEDTAIYYCTRGGTGTRSLYYFDYWGQGATLIV GGGGSGGGGS

GGGGS DIQMTQITSSLSVSLGDRVIISCRASQDIGNFLNWYQQKPDGSLKLLIYYTSRLQSGVPSRFSGWGSGTDYS

LTISNLEEEDIATFFCQQGKTLPYTFGGGTKLEIK TTTPAPRPPTPAPTIASQPLSLRPEACRPAAGGAVHTRGLDFAC

DIYIWAPLAGTCGVLLLSLVITLYCKRGRKKLLYIFKQPFMRPVQTTQEEDGCSCRFPEEEEGGCELRVKFSRSADAPA

YQQGQNQLYNELNLGRREEYDVLDKRRGRDPEMGGKPRRKNPQEGLYNELQKDKMAEAYSEIGMKGERRRGKG

HDGLYQGLSTATKDTYDALHMQALPPR

R24 v3
                                                                (SEQ ID NO. 21)
MALPVTALLLPLALLLHAARP DVQLVESGGGLVQPGGSRKLSCAASGFTFSNFGMHWVRQAPEKGLEWVAYISSG

GSSINYADTVKGRFTISRDNPKNTLFLQMTSLRSEDTAIYYCTRGGTGTRSLYYFDYWGQGATLIV GGGGSGGGGS

GGGGS DIQMTQITSSLSVSLGDRVIISCRASQDIGNFLNWYQQKPDGSLKLLIYYTSRLQSGVPSRFSGWGSGTDYS

LTISNLEEEDIATFFCQQGKTLPYTFGGGTKLEIK EPKSPDKTHTCPPCPAPPVAGPSVFLFPPKPKDTLMIARTPEVTC

VVVDVSHEDPEVKFNWYVDGVEVHNAKTKPREEQYNSTYRVVSVLTVLHQDWLNGKEYKCKVSNKALPAPIEKTIS

KAKGQPREPQVYTLPPSRDELTKNQVSLTCLVKGFYPSDIAVEWESNGQPENNYKTTPPVLDSDGSFFLYSKLTVDK

SRWQQGNVFSCSVMHEALHNHYTQKSLSLSPGKIYIWAPLAGTCGVLLLSLVITLYCKRGRKKLLYIFKQPFMRPVQ

TTQEEDGCSCRFPEEEEGGCELRVKFSRSADAPAYQQGQNQLYNELNLGRREEYDVLDKRRGRDPEMGGKPRRKN
```

PQEGLYNELQKDKMAEAYSEIGMKGERRRGKGHDGLYQGLSTATKDTYDALHMQALPPR

MB3.6-v1
(SEQ ID NO. 22)
MALPVTALLLPLALLLHAARPEVVVVESGGGFVKPGGSLKLSCAAAGFTFSRYAMSWVRQTPEKRLEWVATISSGG

SHTYYPDSVKGRFTISRDNAKNTLYLQMSSLRSEDTAIYYCARPGYDRGAWFFDVWGAGTTVTVSSGGGGSGGGG

SGGGGSDIVLTQSPATLSVTPGDSVSLSCRASQIISNNLHWYQQKSHESPRLLIKYASQSISGIPSRFSGSGSGTDFTLS

INSVETEDFGMYFCQQSNSWPLTFGSGTKLEIKRGLAVSTISSFFPPGYQIYIWAPLAGTCGVLLLSLVITLYCKRGRKK

LLYIFKQPFMRPVQTTQEEDGCSCRFPEEEEGGCELRVKFSRSADAPAYQQGQNQLYNELNLGRREEYDVLDKRRG

RDPEMGGKPRRKNPQEGLYNELQKDKMAEAYSEIGMKGERRRGKGHDGLYQGLSTATKDTYDALHMQALPPR

MB3.6-v2
(SEQ ID NO. 23)
MALPVTALLLPLALLLHAARPEVVVVESGGGFVKPGGSLKLSCAAAGFTFSRYAMSWVRQTPEKRLEWVATISSGG

SHTYYPDSVKGRFTISRDNAKNTLYLQMSSLRSEDTAIYYCARPGYDRGAWFFDVWGAGTTVTVSSGGGGSGGGG

SGGGGSDIVLTQSPATLSVTPGDSVSLSCRASQIISNNLHWYQQKSHESPRLLIKYASQSISGIPSRFSGSGSGTDFTLS

INSVETEDFGMYFCQQSNSWPLTFGSGTKLEIKRTTTPAPRPPTPAPTIASQPLSLRPEACRPAAGGAVHTRGLDFA

CDIYIWAPLAGTCGVLLLSLVITLYCKRGRKKLLYIFKQPFMRPVQTTQEEDGCSCRFPEEEEGGCELRVKFSRSADAP

AYQQGQNQLYNELNLGRREEYDVLDKRRGRDPEMGGKPRRKNPQEGLYNELQKDKMAEAYSEIGMKGERRRGK

GHDGLYQGLSTATKDTYDALHMQALPPR

MB3.6-v3
(SEQ ID NO. 24)
MALPVTALLLPLALLLHAARPEVVVVESGGGFVKPGGSLKLSCAAAGFTFSRYAMSWVRQTPEKRLEWVATISSGG

SHTYYPDSVKGRFTISRDNAKNTLYLQMSSLRSEDTAIYYCARPGYDRGAWFFDVWGAGTTVTVSSGGGGSGGGG

SGGGGSDIVLTQSPATLSVTPGDSVSLSCRASQIISNNLHWYQQKSHESPRLLIKYASQSISGIPSRFSGSGSGTDFTLS

INSVETEDFGMYFCQQSNSWPLTFGSGTKLEIKREPKSPDKTHTCPPCPAPPVAGPSVFLFPPKPKDTLMIARTPEVT

CVVVDVSHEDPEVKFNWYVDGVEVHNAKTKPREEQYNSTYRVVSVLTVLHQDWLNGKEYKCKVSNKALPAPIEKT

ISKAKGQPREPQVYTLPPSRDELTKNQVSLICLVKGFYPSDIAVEWESNGQPENNYKTTPPVLDSDGSFFLYSKLTVD

KSRWQQGNVFSCSVMHEALHNHYTQKSLSLSPGKIYIWAPLAGTCGVLLLSLVITLYCKRGRKKLLYIFKQPFMRPV

QTTQEEDGCSCRFPEEEEGGCELRVKFSRSADAPAYQQGQNQLYNELNLGRREEYDVLDKRRGRDPEMGGKPRRK

NPQEGLYNELQKDKMAEAYSEIGMKGERRRGKGHDGLYQGLSTATKDTYDALHMQALPPR

KM641-v1
(SEQ ID NO. 25)
MALPVTALLLPLALLLHAARPEVTLVESGGDFVKPGGSLKVSCAASGFAFSHYAMSWVRQTPAKRLEWVAYISSGG

SGTYYSDSVKGRFTISRDNAKNTLYLQMRSLRSEDSAMYFCTRVKLGTYYFDSWGQGTTLTVSSGGGGSGGGGSG

GGGSDIQMTQTASSLPASLGDRVTISCSASQDISNYLNWYQQKPDGTVKLLIFYSSNLHSGVPSRFSGGGSGTDYSL

TISNLEPEDIATYFCHQYSKLPWTFGGGTKLEIKGLAVSTISSFFPPGYQIYIWAPLAGTCGVLLLSLVITLYCKRGRKKL

LYIFKQPFMRPVQTTQEEDGCSCRFPFEEEGGCELRVKFSRSADAPAYQQGQNQLYNELNLGRREEYDVLDKRRGR

DPEMGGKPRRKNPQEGLYNELQKDKMAEAYSEIGMKGERRRGKGHDGLYQGLSTATKDTYDALHMQALPPR

KM641-v2
(SEQ ID NO. 26)
MALPVTALLLPLALLLHAARPEVTLVESGGDFVKPGGSLKVSCAASGFAFSHYAMSWVRQTPAKRLEWVAYISSGG

SGTYYSDSVKGRFTISRDNAKNTLYLQMRSLRSEDSAMYFCTRVKLGTYYFDSWGQGTTLTVSSGGGGSGGGGSG

```
GGGSDIQMTQTASSLPASLGDRVTISCSASQDISNYLNWYQQKPDGTVKLLIFYSSNLHSGVPSRFSGGGSGTDYSL

TISNLEPEDIATYFCHQYSKLPWTFGGGTKLEIKTTTPAPRPPTPAPTIASQPLSLRPEACRPAAGGAVHTRGLDFACD

IYIWAPLAGTCGVLLLSLVITLYCKRGRKKLLYIFKQPFMRPVQTTQEEDGCSCRFPEEEEGGCELRVKFSRSADAPAY

QQGQNQLYNELNLGRREEYDVLDKRRGRDPEMGGKPRRKNPQEGLYNELQKDKMAEAYSEIGMKGERRRGKGH

DGLYQGLSTATKDTYDALHMQALPPR

KM641-v3
                                                                    (SEQ ID NO. 27)
MALPVTALLLPLALLLHAARPEVTLVESGGDFVKPGGSLKVSCAASGFAFSHYAMSWVRQTPAKRLEWVAYISSGG

SGTYYSDSVKGRFTISRDNAKNTLYLQMRSLRSEDSAMYFCTRVKLGTYYFDSWGQGTTLTVSSGGGGSGGGGSG

GGGSDIQMTQTASSLPASLGDRVTISCSASQDISNYLNWYQQKPDGTVKLLIFYSSNLHSGVPSRFSGGGSGTDYSL

TISNLEPEDIATYFCHQYSKLPWTFGGGTKLEIKEPKSPDKTHTCPPCPAPPVAGPSVFLFPPKPKDTLMIARTPEVTC

VVVDVSHEDPEVKFNWYVDGVEVHNAKTKPREEQYNSTYRVVSVLTVLHQDWLNGKEYKCKVSNKALPAPIEKTIS

KAKGQPREPQVYTLPPSRDELTKNQVSLTCLVKGFYPSDIAVEWESNGQPENNYKTTPPVLDSDGSFFLYSKLTVDK

SRWQQGNVFSCSVMHEALHNHYTQKSLSLSPGKIYIWAPLAGTCGVLLLSLVITLYCKRGRKKLLYIFKQPFMRPVQ

TTQEEDGCSCRFPEEEEGGCELRVKFSRSADAPAYQQGQNQLYNELNLGRREEYDVLDKRRGRDPEMGGKPRRKN

PQEGLYNELQKDKMAEAYSEIGMKGERRRGKGHDGLYQGLSTATKDTYDALHMQALPPR

BW2121-v1
                                                                    (SEQ ID NO. 28)
MALPVTALLLPLALLLHAARPQVQLQQSGGGLVKPGGSLTLSCAASRFTFSTYAMSWVRQTPAKRLEWVAYISSGG

ASTYYRDSVKGRFTISRDNAKNTLYLQMSSLRSEDTAMYYCARGGSRYAMDYWGQGTTVTVSSGGGGSGGGGS

GGGGSDIQLTQSPAILSVSPGERVSFSCWASQSIGTSIHWYQQRTNGSPRLLIKYSSESISGIPSRFSGSGSGTDFTLSI

NSLESEDIADYYCQQTYSWPFTFGSGTKLEIGLAVSTISSFFPPGYQIYIWAPLAGTCGVLLLSLVITLYCKRGRKKLLYIF

KQPFMRPVQTTQEEDGCSCRFPEEEEGGCELRVKFSRSADAPAYQQGQNQLYNELNLGRREEYDVLDKRRGRDPE

MGGKPRRKNPQEGLYNELQKDKMAEAYSEIGMKGERRRGKGHDGLYQGLSTATKDTYDALHMQALPPR

BW2121-v2
                                                                    (SEQ ID NO. 29)
MALPVTALLLPLALLLHAARPQVQLQQSGGGLVKPGGSLTLSCAASRFTFSTYAMSWVRQTPAKRLEWVAYISSGG

ASTYYRDSVKGRFTISRDNAKNTLYLQMSSLRSEDTAMYYCARGGSRYAMDYWGQGTTVTVSSGGGGSGGGGS

GGGGSDIQLTQSPAILSVSPGERVSFSCWASQSIGTSIHWYQQRTNGSPRLLIKYSSESISGIPSRFSGSGSGTDFTLSI

NSLESEDIADYYCQQTYSWPFTFGSGTKLEITTTPAPRPPTPAPTIASQPLSLRPEACRPAAGGAVHTRGLDFACDIYI

WAPLAGTCGVLLLSLVITLYCKRGRKKLLYIFKQPFMRPVQTTQEEDGCSCRFPEEEEGGCELRVKFSRSADAPAYQQ

GQNQLYNELNLGRREEYDVLDKRRGRDPEMGGKPRRKNPQEGLYNELQKDKMAEAYSEIGMKGERRRGKGHDG

LYQGLSTATKDTYDALHMQALPPR

BW2121-v3
                                                                    (SEQ ID NO. 30)
MALPVTALLLPLALLLHAARPQVQLQQSGGGLVKPGGSLTLSCAASRFTFSTYAMSWVRQTPAKRLEWVAYISSGG

ASTYYRDSVKGRFTISRDNAKNTLYLQMSSLRSEDTAMYYCARGGSRYAMDYWGQGTTVTVSSGGGGSGGGGS

GGGGSDIQLTQSPAILSVSPGERVSFSCWASQSIGTSIHWYQQRTNGSPRLLIKYSSESISGIPSRFSGSGSGTDFTLSI

NSLESEDIADYYCQQTYSWPFTFGSGTKLEIEPKSPDKTHTCPPCPAPPVAGPSVFLFPPKPKDTLMIARTPEVTCVV

VDVSHEDPEVKFNWYVDGVEVHNAKTKPREEQYNSTYRVVSVLTVLHQDWLNGKEYKCKVSNKALPAPIEKTISKA

KGQPREPQVYTLPPSRDELTKNQVSLTCLVKGFYPSDIAVEWESNGQPENNYKTTPPVLDSDGSFFLYSKLTVDKSR
```

WQQGNVFSCSVMHEALHNHYTQKSLSLSPGKIYIWAPLAGTCGVLLLSLVITLYCKRGRKKLLYIFKQPFMRPVQTT

QEEDGCSCRFPEEEEGGCELRVKFSRSADAPAYQQGQNQLYNELNLGRREEYDVLDKRRGRDPEMGGKPRRKNP

QEGLYNELQKDKMAEAYSEIGMKGERRRGKGHDGLYQGLSTATKDTYDALHMQALPPR

Example 3: In Vitro Testing of Anti-GD3 scCARs

Materials and Methods
RNA In Vitro Transcription mRNA encoding the scCAR were in vitro transcribed and polyadenylated using the mMessage mMachine T7 Ultra kit (Life technologies) following the manufacturer's instructions. RNAs were purified with RNeasy columns (Qiagen), eluted in cytoporation medium T (Harvard Apparatus), and quantified by measuring absorbance at 260 nm using a Nanodrop ND-1000 spectrophotometer. Quality of the RNA was verified on a denaturing formaldehyde/MOPS agarose gel.

RNA Electroporation of T Cells 4-5 days or 11-12 post-activation, T lymphocytes were transfected by electrotransfer of messenger RNA using an AgilePulse MAX system (Harvard Apparatus). Following removal of activation beads, cells were pelleted, resuspended in cytoporation medium T at $25 \times 10^6$ cells/ml. $5 \times 10^6$ cells were mixed with 15 µg of the mRNA encoding the scCAR into a 0.4 cm cuvette. The electroporation consisted of two 0.1 ms pulses at 1200 V followed by four 0.2 ms pulses at 130V. Following electroporation, cells were diluted into culture medium and incubated at 37° C./5% $CO_2$.

Detection of scCAR

By flow cytometry: The T cells were first stained with either biotin-labeled polyclonal goat anti-mouse $(Fab)_2$ antibodies (Jackson Immunoresearch) or biotin-labeled protein L (GenScript), and then stained with phycoerythrin-labeled streptavidin (BD pharmingen), and finally analysed using the MACSQuant flow cytometer (Miltenyi).

By Western blotting: $1 \times 10^6$ T cells were lysed in 50 µl RIPA buffer containing 1 mM orthovanadate, 3 µg/ml of protease inhibitor and 2 mM of PMSF. Cells lysates were separated by SDS-PAGE on a Any kD™ acrylamide gel (BioRad). After transfer to a nitrocellulose membrane, this was incubated with a mouse anti-human CD3z (pharmingen) and then with a goat anti-mouse IgG horseradish peroxidase-conjugated antibody (sigma). Antibody binding was revealed by using the ECL kit (Pierce).

Degranulation Assay $5 \times 10^4$ T cells were co-cultured with $5 \times 10^4$ GD3-positive or GD3-negative cells in 0.1 ml per well in a 96-well plate. APC-labeled anti-CD107a (BD Biosciences) was added at the beginning of the co-culture in addition to 1 µg/ml of anti-CD49d (BD Biosciences), 1 µg/ml of anti-CD28 (Miltenyi), and 1× Monensin solution (eBioscience). After a 6 h incubation, the cells were stained with a fixable viability dye (eBioscience) and vioblue-labeled anti-CD8 (Miltenyi) and analyzed using the MACSQuant flow cytometer (Miltenyi). Of note: degranulating cytotoxic T cells correspond to CD8+CD107a+ cells.

Cytokine Release Assay $5 \times 10^4$ T cells were co-cultured with $5 \times 10^4$ GD3-positive or GD3-negative cells in 0.1 ml per well in a 96-well plate. After a 24 hours incubation, the culture supernatants were collected and analysed for IFNg production using ELISA (R&D Systems).

Cytotoxicity Assay $2 \times 10^4$ GD3-positive or GD3-negative cells were seeded in 0.1 ml per well in a 96 well plate. The day after the plating, the GD3-positive and GD3-negative cells were labeled with CellTrace CFSE and co-cultured with $4 \times 10^5$ T cells for 4 hours. The cells were then harvested, stained with a fixable viability dye (eBioscience) and analyzed using the MACSQuant flow cytometer (Miltenyi).

The percentage of specific lysis was calculated using the following formula:

$$\% \text{ cell lysis} = 100\% - \frac{\frac{\% \text{ viable target cells upon coculture with CAR modified } T \text{ cells}}{\% \text{ viable control cells upon coculture with CAR modified } T \text{ cells}}}{\frac{\% \text{ viable target cells upon coculture with non modified } T \text{ cells}}{\% \text{ viable control cells upon coculture with non modified } T \text{ cells}}}$$

Results

Figure 5:
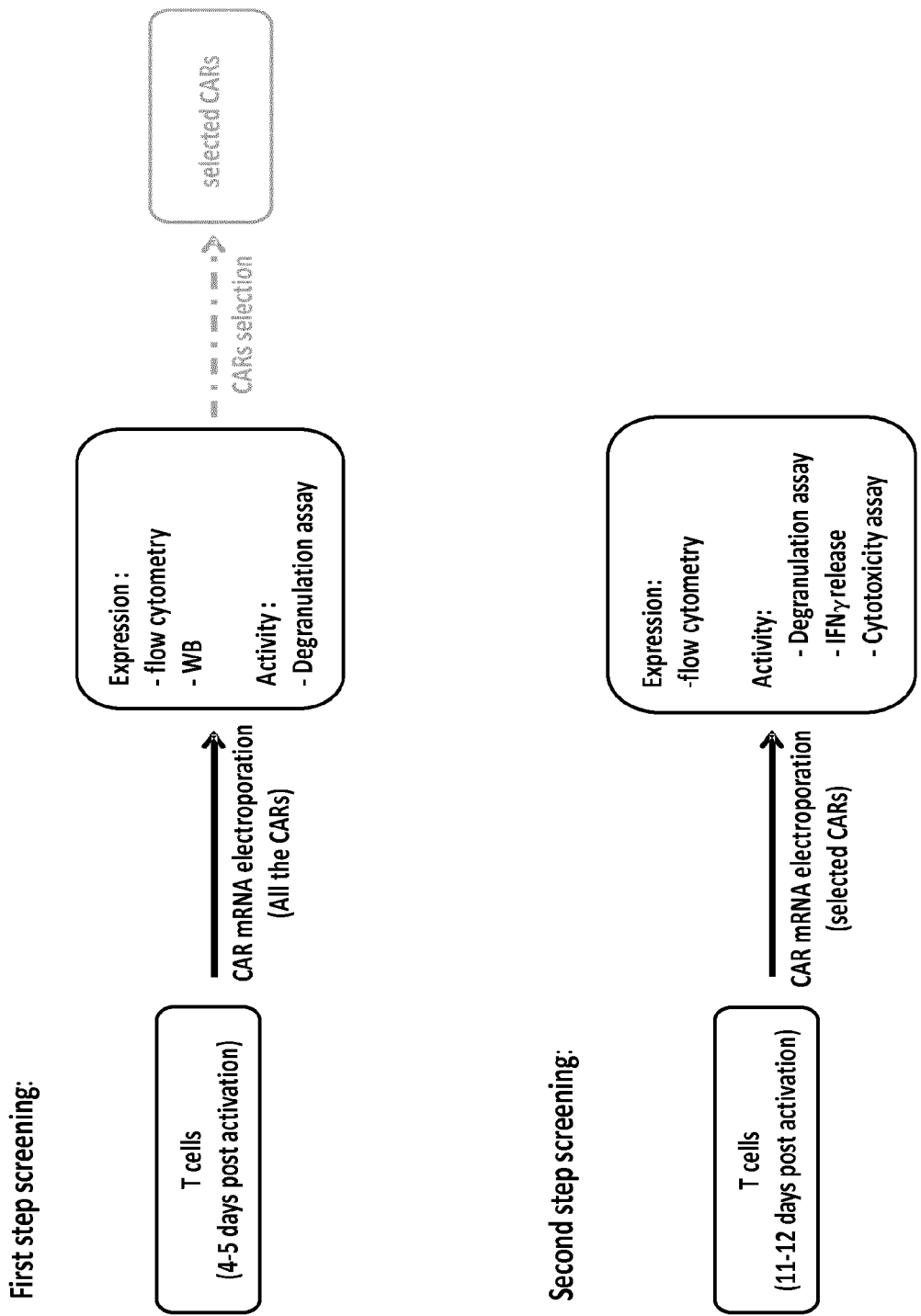
FIG. 5: Two-step screening method used to test the anti-GD3 scCARs designed in human primary T cells.

The anti-GD3 scCARs designed were tested in human primary T cells using a two-step screening method (FIG. 5).

In the first step of the screening process, primary human T cells previously activated for 4-5 days with anti-CD28/CD3 beads and IL-2 were electroporated with mRNA encoding the 12 anti-GD3 scCARs designed. 1 day post electroporation, scCARs expression was assessed by flow cytometry and western blot, and scCAR-modified T cells activity was assessed by measuring T cells degranulation. The scCARs that were detected by western blot and that induced significant specific degranulation of T cells (≥20%) upon co-culture with at least one GD3 positive cell line were selected to pass through the second step of the screening process.

In the second step of the screening process, primary human T cells previously activated for 11-12 days with anti-CD28/CD3 beads and IL-2 were electroporated with mRNA encoding the anti-GD3 scCARs selected after the first screening step. 1-2 days post electroporation, scCARs expression was assessed by flow cytometry, and scCAR-modified T cells activity was assessed by measuring effector functions of T cells. The scCARs that triggered significant specific degranulation of T cells (≥20%), significant specific lysis of target cells (≥20%) and significant production of IFNg by T cells (≥1500 pg/ml) upon co-culture with at least one GD3 positive cell line were selected as potential scCAR candidates.

a) Primary Screening of scCARs:
scCAR Expression:

The total expression of anti-GD3 scCARs in T cells was assessed by western blot using an anti-human CD3 zeta mAb. We observed that all the scCARs were strongly detected in T cells lysates, except the scCAR BW2121-v1 (FIGS. 6A and 6B).

Then was assessed the surface expression of anti-GD3 scCARs on T cell by flow cytometry using anti-Fab or protein L. It was observed that 1°) the scCARs MB3.6-v2, MB3.6-v3 and BW2121-v2 that were well detected in T cells lysate by western blot were also well detected on the T cell surface by flow cytometry; 2°) the scCAR BW2121-v1 that was almost not detected in T cell lysates by western blot was also not detected on the T cell surface by flow cytometry (FIGS. 7A and 7B, results obtained from at least three different FACS analysis runs).

Figure 7B:
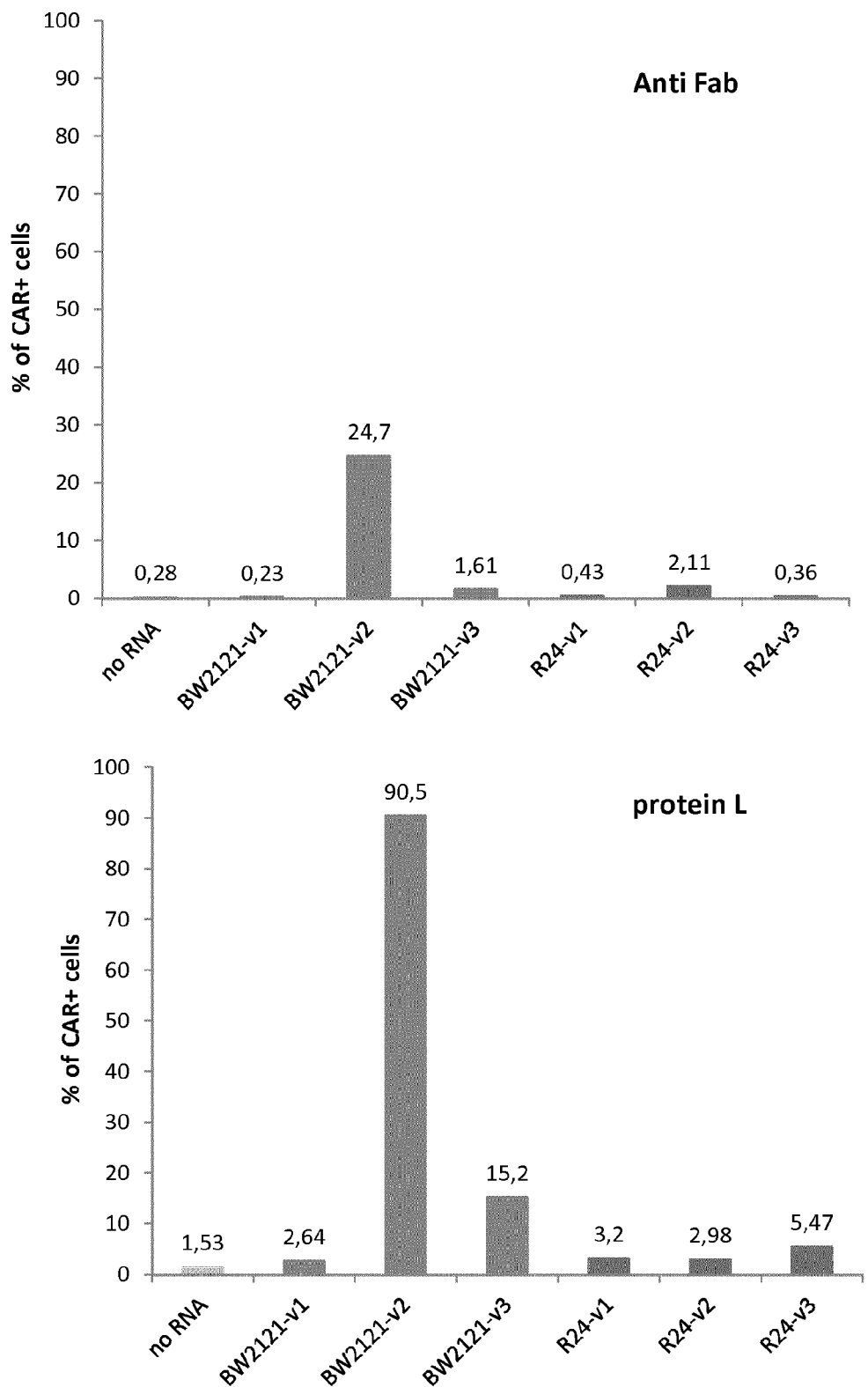
FIG. 7: During primary screening, analysis of total expression of 12 scCARs in human T cells by western blot using anti-Fab or protein L (A) first series. (B) second series.

Surprisingly, the scCARs MB3.6-v1, KM641-v1, KM641-v2, KM641-v3, BW2121-v3, R24-v1, R24-v2 and R24-v3 that were well detected in T cells lysate by western blot were almost undetectable on the T cell surface by flow cytometry (FIGS. 7A and 7B and results obtained from at least 3 FACS analysis runs).

scCAR Activity:

To assess scCAR activity, the degranulation of scCAR-modified T cells upon co-culture with GD3-positive (SK-MEL-28 and MeWo) or GD3-negative (MCF-7) cells was analyzed.

Figure 8A:
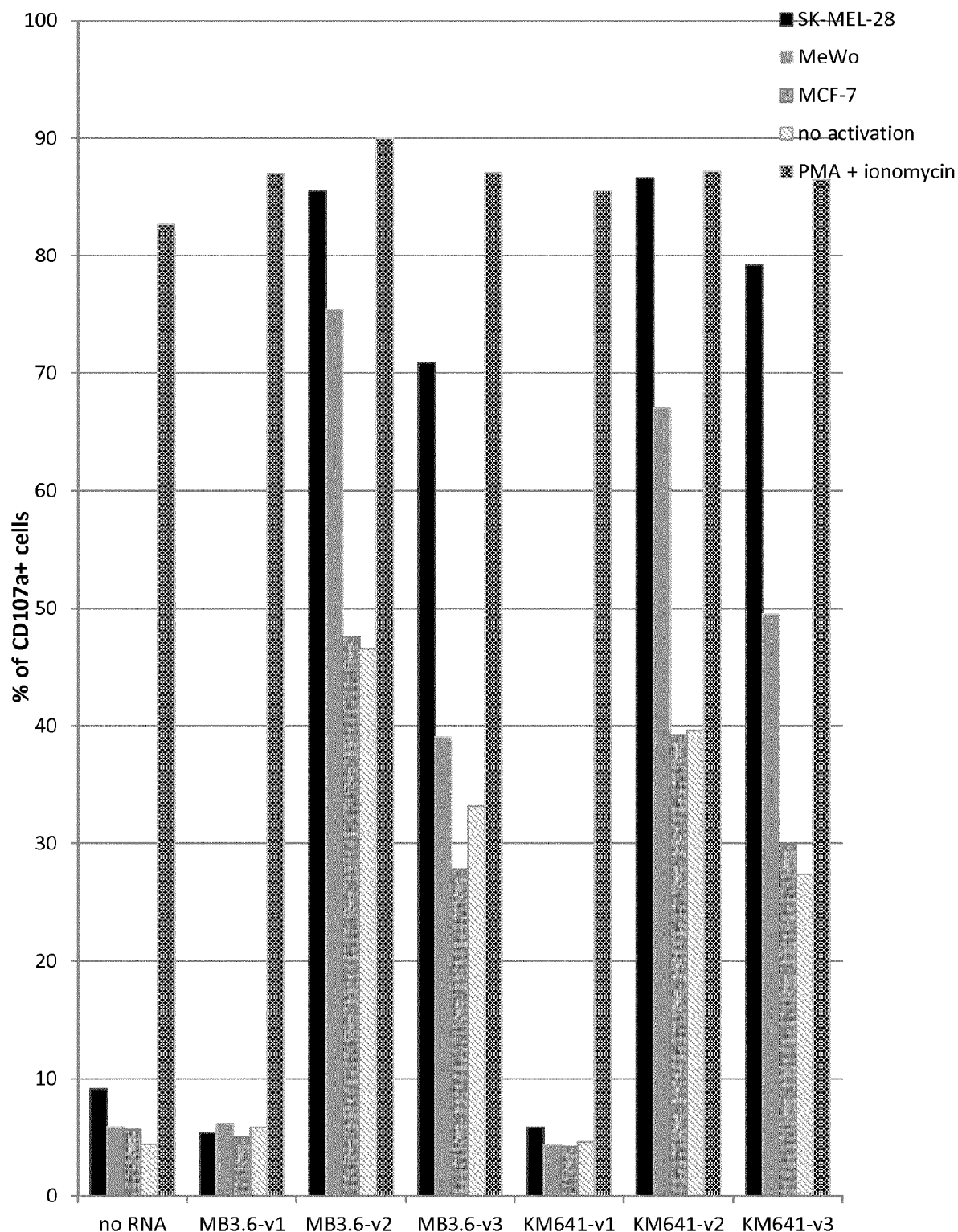
FIG. 8: During primary screening, analysis of degranulation of 12 scCAR modified T cells upon co-culture with target cells. (A) first series. (B) second series.
Figure 8B:
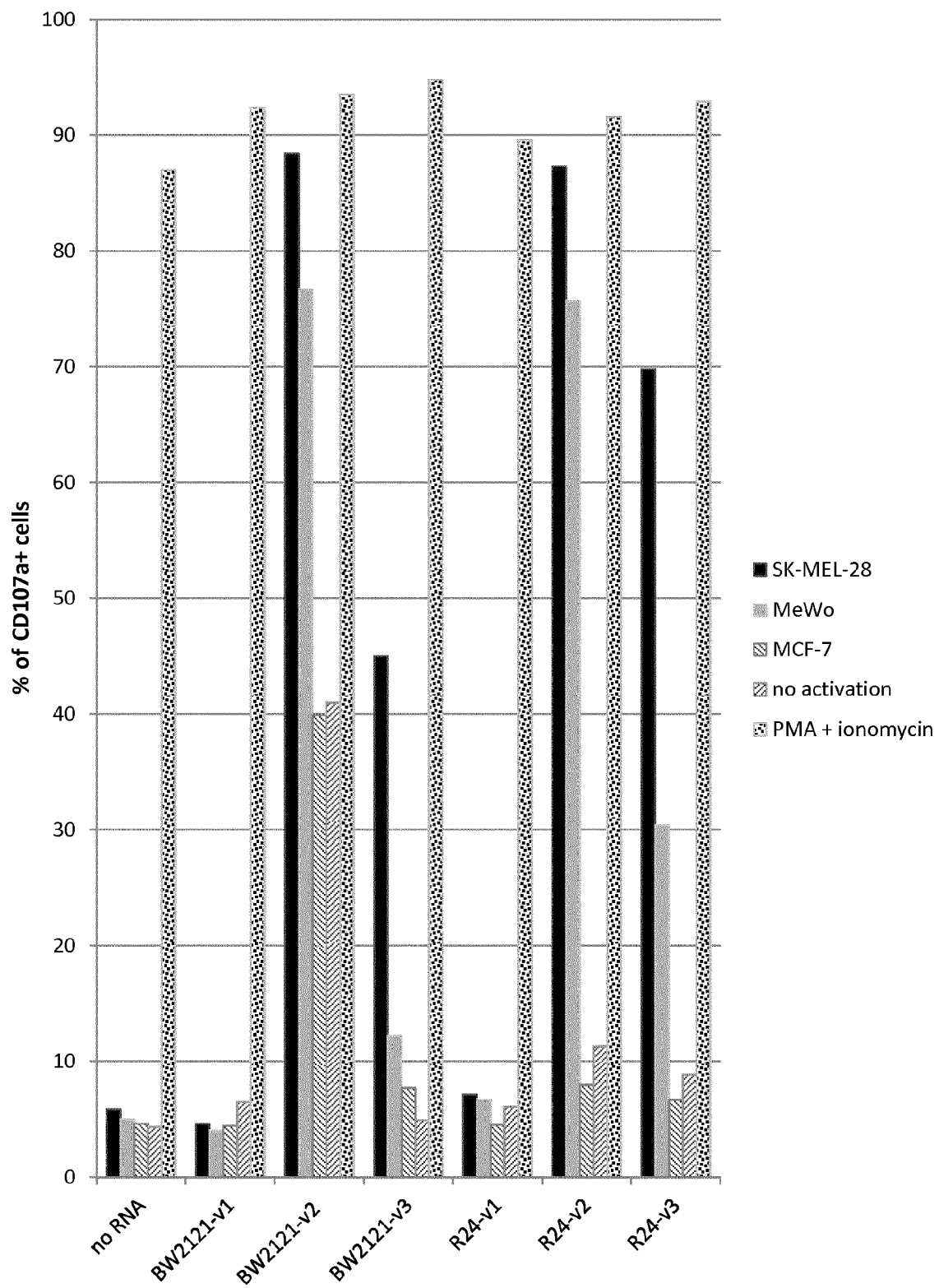

It was observed that 1°) the T cells modified with the scCARs R24-v2 and R24-v3 degranulated exclusively and significantly (≥20%) upon co-culture with SK-MEL-28 and MeWo cells. 2°) the T cells modified with the scCAR BW2121-v3 degranulated exclusively and significantly (≥20%) upon coculture with SK-MEL-28 cells; 3°) the T cells modified with the scCARs MB3.6-v1, KM641-v1, BW2121-v1 and R24-v1 did not degranulate at all upon co-culture with SK-MEL-28 or MeWo cells; 4°) the T cells modified with the scCARs MB3.6-v2, MB3.6-v3, KM641-v2, KM641-v3 and BW2121 degranulated significantly (≥20%) upon co-culture with SK-MEL-28 and MeWo cells but also upon coculture with MCF-7 cells or without any stimulation (FIGS. 8A and 8B, results obtained from at least three different FACS analysis runs).

Figure 9:
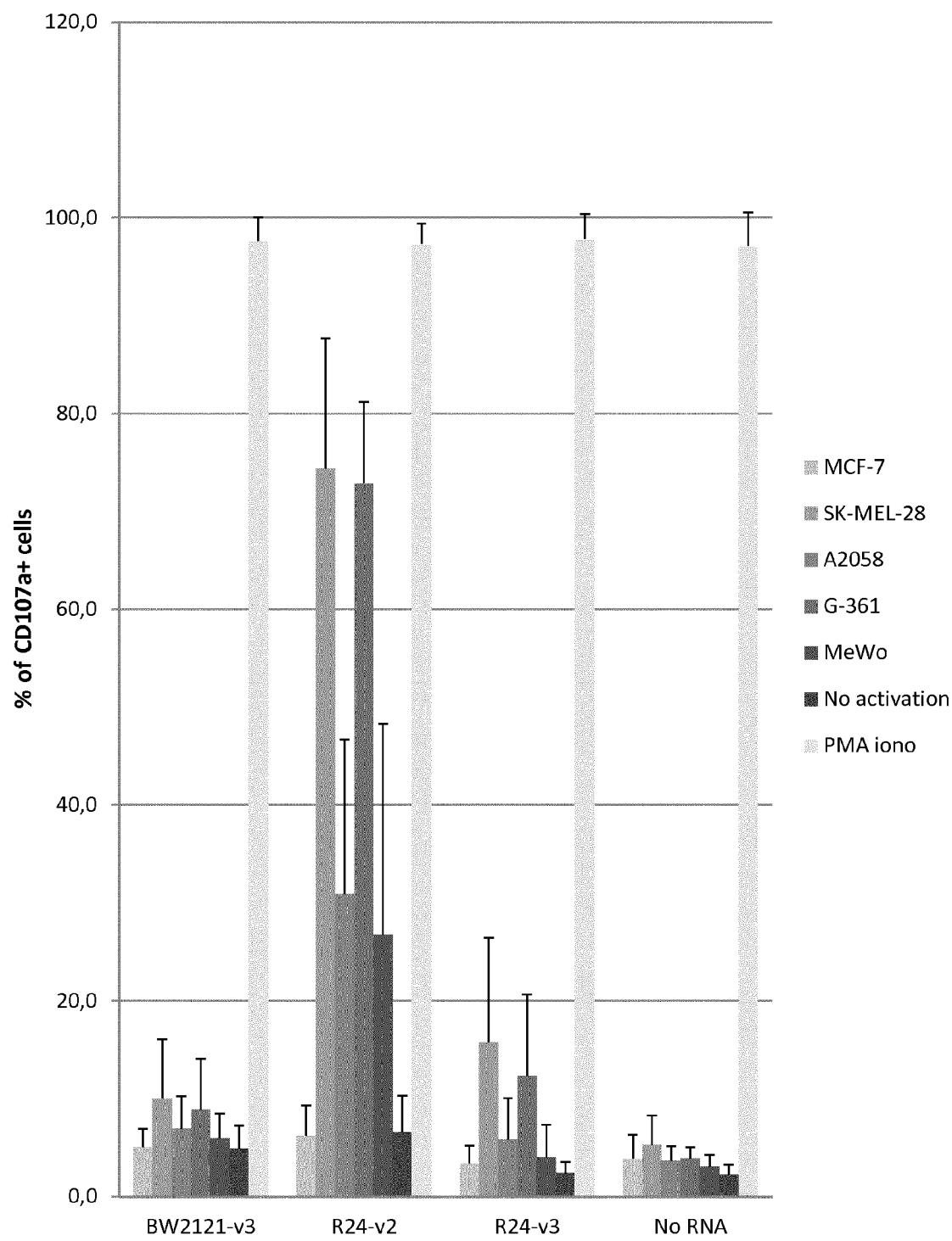
FIG. 9: During secondary screening, analysis of degranulation of scCAR modified T cells upon co-culture with target cells. Data are presented as mean+/−SD of four independent experiments.

Altogether the results presented in the present invention demonstrate that among the twelve anti-GD3 scCARs designed, three (BW2121-v3, R24-v2 and R24-v3) were considered as the best ones and will be analyzed further through to the second step of the screening process. At this point, the constructs involving MB3.6 ScFv were discarded as showing too much non-specific degranulation, i.e. strong activation of the T-cells in the absence of GD3 positive cells (no activation).

a) Secondary Screening of scCARs:

scCAR Expression:

The surface expression of anti-GD3 scCARs on T cells was assessed by flow cytometry using anti-Fab or protein L. It was observed that the scCARs BW2121-v3 and R24-v2 were detected in one experiment out of four using anti-Fab and in none of the experiments using protein L. The scCAR R24-v3 was detected neither with the anti-Fab nor with the protein L.

scCAR Activity:

To assess scCAR activity, firstly was analysed the degranulation of scCAR-modified T cells upon co-culture with GD3-positive (SK-MEL-28, G-361, MeWo and A2058) cells or GD3-negative (MCF-7) cells. It was observed that contrary to the T cells modified with the scCARs BW2121-v3 and R24-v3, the T cells modified with the scCAR R24-v2 degranulated significantly more (≥20%) upon co-culture with SK-MEL-28, G-361 and A2058 than upon co-culture with MCF-7 or in media alone (FIG. 9 results from at least three different FACS analysis runs). The non-modified T cells did not degranulate at all upon coculture with SK-MEL-28, G-361, MeWo, A2058 and MCF-7 cells (FIG. 9 results obtained from at least three different FACS analysis runs).

Figure 10:
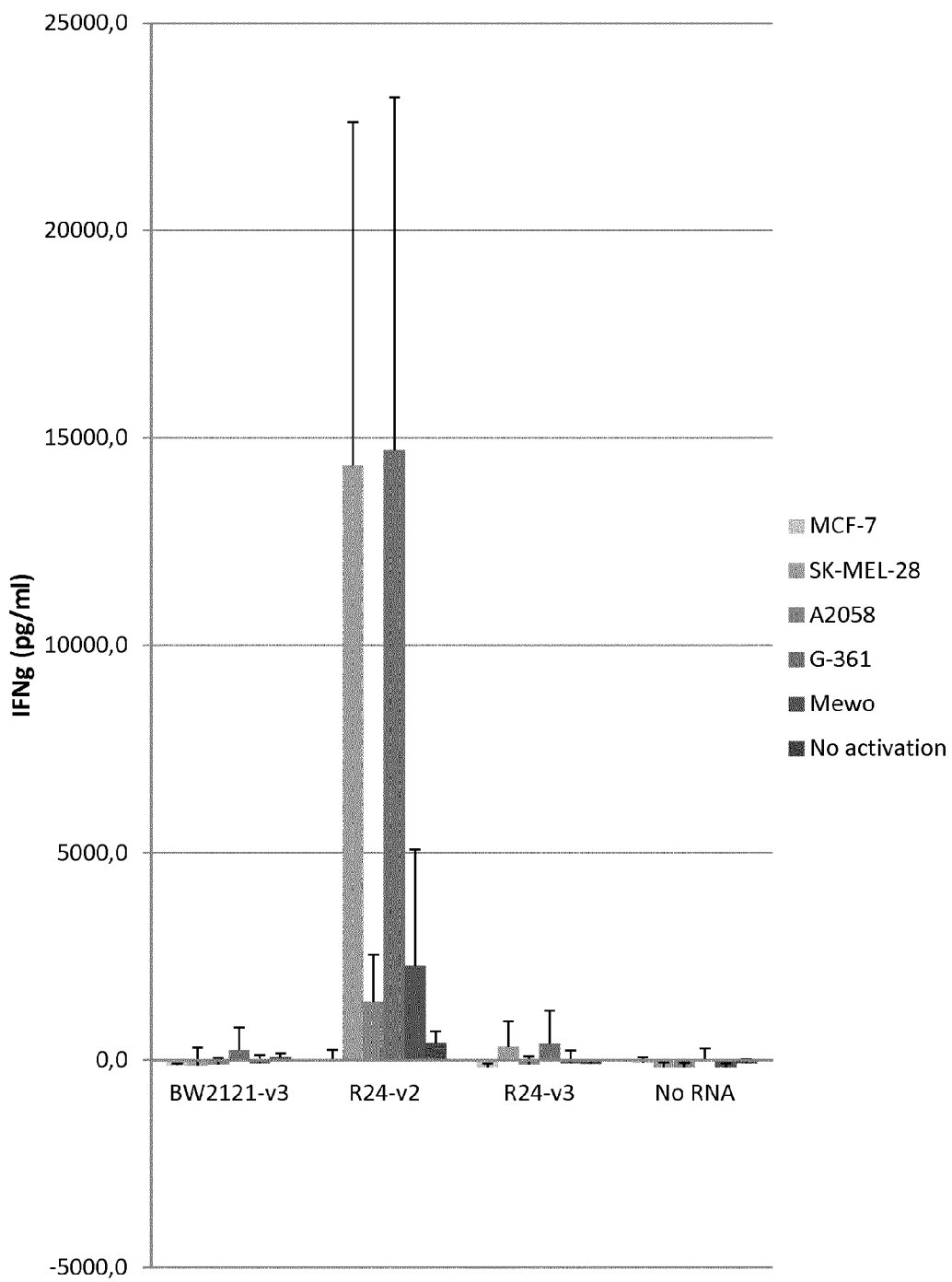
FIG. 10: During secondary screening, analysis of IFNγ production by scCAR-modified T cells upon co-culture with target cells. Data are presented as mean+/−SD of four independent experiments.

Then was analyzed the production of IFNγ by scCAR-modified T cells upon co-culture with GD3-positive (SK-MEL-28, G-361, MeWo and A2058) or GD3-negative (MCF-7) cells. It was observed that contrary to the T cells modified with the scCARs BW2121-v3 and R24-v3, the T cells modified with the scCAR R24-v2 produced significantly more IFNγ (≥1500 pg/ml) upon co-culture with SK-MEL-28, G-361 and MeWo than upon co-culture with MCF-7 or in media alone (FIG. 10). The non-modified T cells did not produce any IFNγ upon co-culture with SK-MEL-28, G-361, MeWo, A2058 and MCF-7 (FIG. 10).

Figure 11:
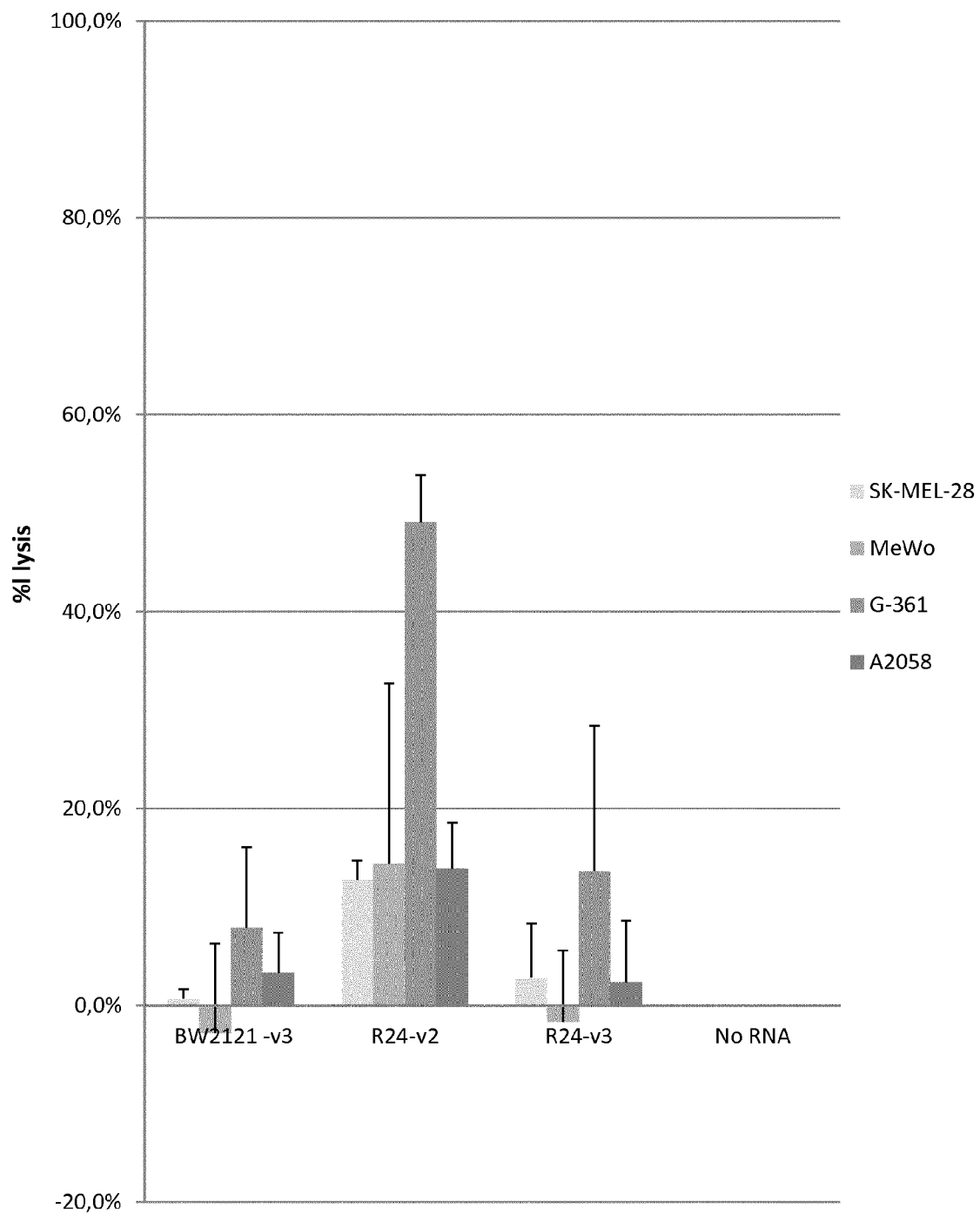
FIG. 11: During secondary screening, analysis of cytotoxic activity of scCAR-modified T cells upon co-culture with adherent target cells. Data are presented as mean+/−SD of three independent experiments.

Finally was analysed the cytotoxic activity of scCAR-modified T cells upon co-culture with GD3-positive (SK-MEL-28, G-361, MeWo and A2058) or GD3-negative (MCF-7) cells. It was observed that contrary to the T cells modified with the scCARs BW2121-v3 and R24-v3, the T cells modified with the scCAR R24-v2 specifically killed more than 20% of G-361 cells in co-culture (FIG. 11, which represents mean+/−SD of 3 independent experiments). Interestingly, whereas SK-MEL-28 cells induced similar levels of T cells degranulation and IFNg production than G-361 cells, these cells were considerably less sensitive to lysis than G-361 cells (FIG. 11).

Altogether our results demonstrated that the scCAR R24-v2 represents one of the best scCAR for further studies.

These experiments show that the present constructs according to the invention, especially those including the R24 scFv, and more particularly those using conformation V2, resulted into a stronger response in terms of T cells degranulation.

Example 4: Proliferation of TCRalpha Inactivated Cells Expressing a GD3-CAR

Heterodimeric TALE-nuclease targeting two 17-bp long sequences (called half targets) separated by an 15-bp spacer within T-cell receptor alpha constant chain region (TRAC) gene were designed and produced as described in WO2013176915. Each half target is recognized by repeats of the half TALE-nucleases listed in Table 11.

TABLE 11

TAL-nucleases targeting TCRalpha gene

| Target | Target sequence | Repeat sequence | Half TALE-nuclease |
|---|---|---|---|
| TRAC_T01 | TTGTCCCACAGATATCC Agaaccctgaccctg CCGTGTACCAGCTGAGA (SEQ ID NO: 61) | Repeat TRAC_T01-L Repeat TRAC_T01-R | TRAC_T01-L TALEN TRAC_T01-R TALEN |

Each TALE-nuclease construct was subcloned using restriction enzyme digestion in a mammalian expression vector under the control of the T7 promoter. mRNA encoding TALE-nuclease cleaving TRAC genomic sequence were synthesized from plasmid carrying the coding sequence downstream from the T7 promoter.

Purified T cells preactivated during 72 hours with anti-CD3/CD28 coated beads were transfected with each of the 2 mRNAs encoding both half TRAC_T01 TALE-nucleases. 48 hours post-transfection, different groups of T cells from the same donor were respectively transduced with a lentiviral vector encoding one of the GD3 CAR previously described (SEQ ID NO: 19 to 30). 2 days post-transduction, $CD3_{NEG}$ cells were purified using anti-CD3 magnetic beads and 5 days post-transduction cells were reactivated with soluble anti-CD28 (5 µg/ml).

Cell proliferation was followed for up to 30 days after reactivation by counting cell 2 times per week. Increased proliferation in TCR alpha inactivated cells expressing the GD3 CARs, especially when reactivated with anti-CD28, was observed compared to non-transduced cells.

To investigate whether the human T cells expressing the GD3 CAR display activated state, the expression of the activation marker CD25 are analyzed by FACS 7 days post transduction. The purified cells transduced with the lentiviral vector encoding GD3 CAR assayed for CD25 expression at their surface in order to assess their activation in comparison with the non-transduced cells. Increased CD25 expression is expected both in CD28 reactivation or no reactivation conditions.

It was observed that the primary activated T cells expressing the different GD3 CAR constructs according to the invention were behaving the same way as the TCR inactivated T cells expressing the same GD3 CAR constructs.

Example 5: Generation of GD3 CAR T-Cells

Figure 12:
FIG. 12: Bicistronic lentiviral vector encoding under the transcriptional control of the Spleen Focus Forming Virus (SFFV) promoter the R24-v2 CAR and the suicide gene (RQR8) separated by a 2A peptide.

To permanently modify T cells with GD3 specific CAR, we developed a bicistronic lentiviral vector encoding the R24-v2 CAR and the suicide gene (RQR8) separated by a 2A peptide (FIG. 12).

Figure 13:
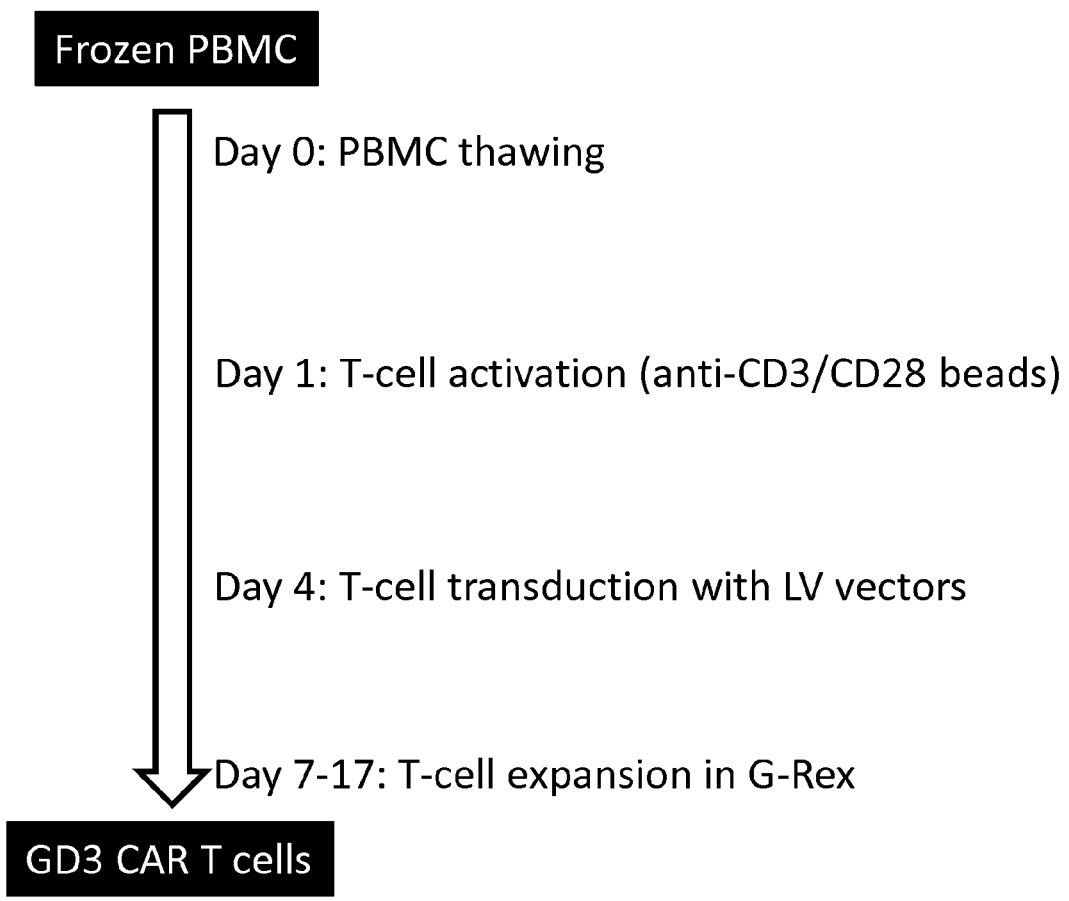
FIG. 13: Transduction of CD3/CD28-stimulated peripheral blood mononuclear cells (PBMCs) with a lentiviral vector encoding under the transcriptional control of the Spleen Focus Forming Virus promoter (SFFV) the R24-v2 CAR and the suicide gene (RQR8) separated by a 2A peptide.

This lentiviral vector was used to transduce CD3/CD28-stimulated peripheral blood mononuclear cells (PBMCs) from healthy donors, and stably modified T cells were expanded in G-Rex (FIG. 13).

Example 6: GD3 CART Cells Activate Multiple Effector Functions when Cocultured with GD3-Positive Target Cells To examine the effector function and the specificity of GD3 redirected T cells, we measured the secretion of interferon γ (IFN-γ), the cell surface expression of the degranulation marker CD107a and the lytic activity following coculture with various tumor cell lines.

Figure 14:
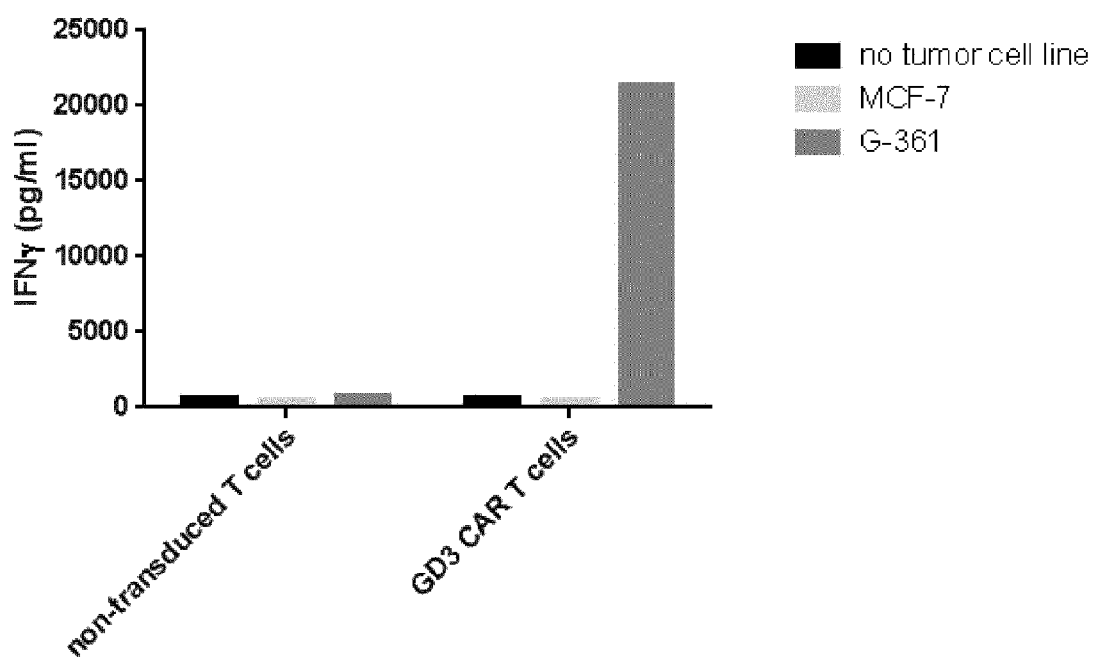
FIG. 14: Secretion of interferon γ (IFN-γ) by lentiviral transduced GD3 CAR T cells or non-transduced T cells in the presence of GD3+ cells (G361), GD-cells (MCF-7) or non-tumor cells.
Figure 15:
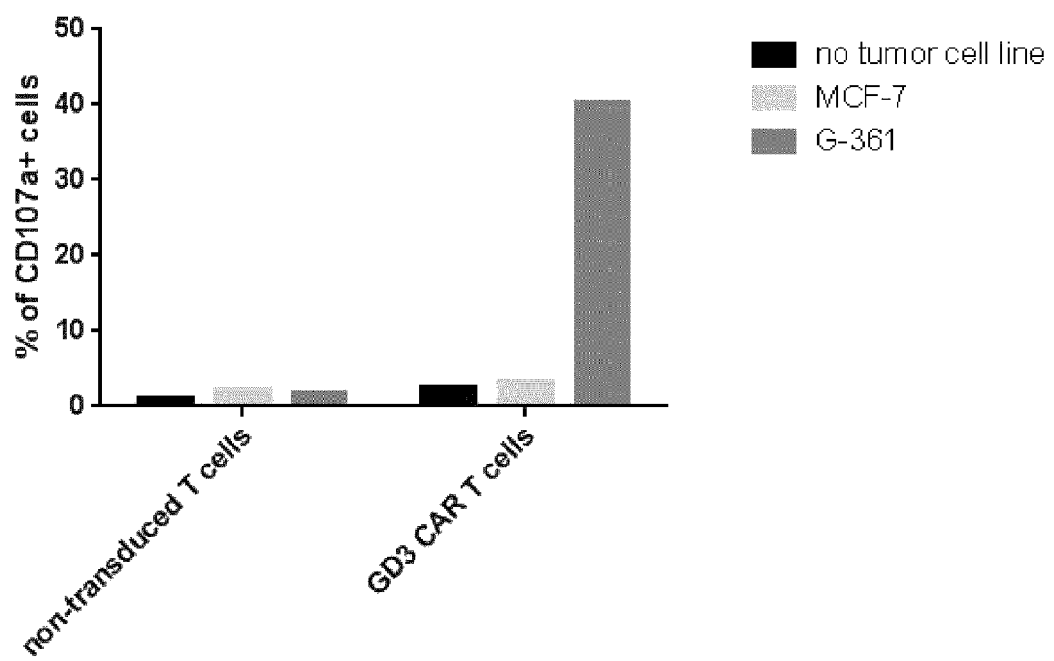
FIG. 15: Expression of CD107α at the cell surface of lentiviral transduced GD3 CAR T cells or non-transduced T cells in the presence of GD3+ cells (G361), GD-cells (MCF-7) or non-tumor cells.
Figure 16:
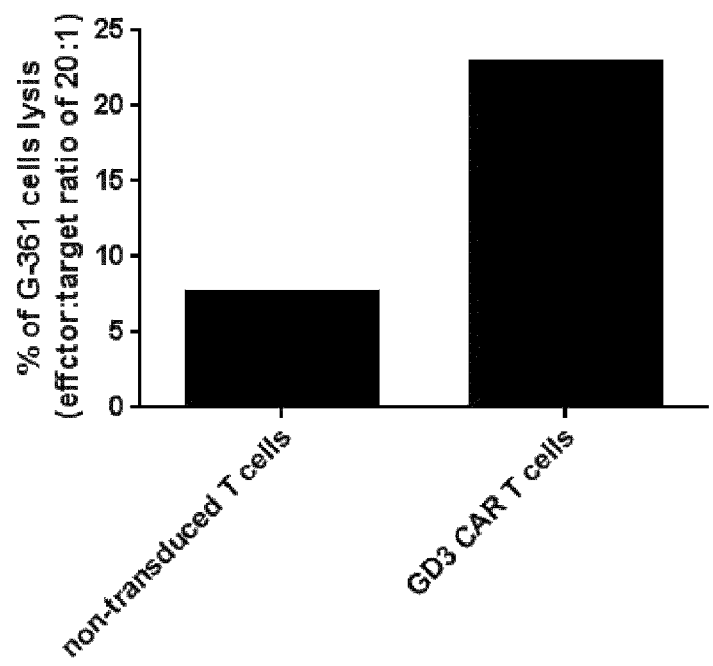
FIG. 16: Lytic activity of lentiviral transduced GD3 CAR T-cells or non-transduced T cells towards GD3+ cells (G361).

As expected, GD3 CAR T cells produced IFNγ, expressed CD107α at the cell surface and display lytic activity when cocultured with GD3 positive target cells (G361) but not when cocultured with GD3 negative cells (MCF-7) (FIGS. 14, 15 and 16).

REFERENCES

Arimondo, P. B., C. J. Thomas, et al. (2006). "Exploring the cellular activity of camptothecin-triple-helix-forming oligonucleotide conjugates." Mol Cell Biol 26(1): 324-33.

Atkins, J. F., N. M. Wills, et al. (2007). "A case for "StopGo": reprogramming translation to augment codon meaning of GGN by promoting unconventional termination (Stop) after addition of glycine and then allowing continued translation (Go)." Rna 13(6): 803-10.

Bierer, B. E., G. Hollander, et al. (1993). "Cyclosporin A and FK506: molecular mechanisms of immunosuppression and probes for transplantation biology." Curr Opin Immunol 5(5): 763-73.

Birklé, S., Zeng, G., Gao, L., Yu, R. K., and Aubry, J. (2003). Role of tumor-associated gangliosides in cancer progression. Biochimie 85, 455-463.

Boch, J., H. Scholze, et al. (2009). "Breaking the code of DNA binding specificity of TAL-type III effectors." Science 326(5959): 1509-12.

Byrd, John. (2014). "Chronic Lymphocytic Leukemia." ASH Annual Meeting & Exposition.

Choulika, A., A. Perrin, et al. (1995). "Induction of homologous recombination in mammalian chromosomes by using the I-SceI system of Saccharomyces cerevisiae." Mol Cell Biol 15(4): 1968-73.

Christian, M., T. Cermak, et al. (2010). "Targeting DNA double-strand breaks with TAL effector nucleases." Genetics 186(2): 757-61.

Cong, L., F. A. Ran, et al. (2013). "Multiplex genome engineering using CRISPR/Cas systems." Science 339 (6121): 819-23.

Cros, E. et al. (2004). "Problems related to resistance to cytarabine in acute myeloid leukemia". Leukemia & Lymphoma. 45(6):1123-1132.

Deltcheva, E., K. Chylinski, et al. (2011). "CRISPR RNA maturation by trans-encoded small RNA and host factor RNase III." Nature 471(7340): 602-7.

Daniotti, J. L., Rosales Fritz, V., Kunda, P., Nishi, T., and Maccioni, H. J. (1997). Cloning, characterization and developmental expression of alpha2,8 sialyltransferase (GD3 synthase, ST8Sia I) gene in chick brain and retina. Int. J. Dev. Neurosci. Off. J. Int. Soc. Dev. Neurosci. 15, 767-776.

Donnelly, M. and G. Elliott (2001). "Nuclear localization and shuttling of herpes simplex virus tegument protein VP13/14." J Virol 75(6): 2566-74.

Doronina, V. A., C. Wu, et al. (2008). "Site-specific release of nascent chains from ribosomes at a sense codon." Mol Cell Biol 28(13): 4227-39.

Eisenschmidt, K., T. Lanio, et al. (2005). "Developing a programmed restriction endonuclease for highly specific DNA cleavage." Nucleic Acids Res 33(22): 7039-47.

Gardin, C. et al. (2007). "Postremission treatment of elderly patients with acute myeloid leukemia in first complete remission after intensive induction chemotherapy: results of the multicenter randomized Acute Leukemia French Association (ALFA) 9803 trial". Blood. 109(12):5129-5135.

Garneau, J. E., M. E. Dupuis, et al. (2010). "The CRISPR/Cas bacterial immune system cleaves bacteriophage and plasmid DNA." Nature 468(7320): 67-71.

Gasiunas, G., R. Barrangou, et al. (2012). "Cas9-crRNA ribonucleoprotein complex mediates specific DNA cleavage for adaptive immunity in bacteria." Proc Natl Acad Sci USA 109(39): E2579-86.

Gravotta, D., Landa, C. A., Panzetta, P., and Maccioni, H. J. (1989). In vivo and in vitro expression of gangliosides in chick retina Mueller cells. J. Neurochem. 52, 768-776.

Guest, R. D., Hawkins, R. E., Kirillova, N., Cheadle, E. J., Arnold, J., O'Neill, A., Irlam, J., Chester, K. A., Kemshead, J. T., Shaw, D. M., et al. (2005). The role of extracellular spacer regions in the optimal design of chimeric immune receptors: evaluation of four different scFvs and antigens. J. Immunother. Hagerstown Md. 1997 28, 203-211.

Haraguchi, M., Yamashiro, S., Yamamoto, A., Furukawa, K., Takamiya, K., Lloyd, K. O., Shiku, H., Furukawa, K. (1994) "Isolation of GD3 synthase gene by expression cloning of GM3 alpha-2,8-sialyltransferase cDNA using anti-GD2 monoclonal antibody." Proc. Natl. Acad. Sci. U.S.A. 91:10455-10459.

Henderson, D. J., I. Naya, et al. (1991). "Comparison of the effects of FK-506, cyclosporin A and rapamycin on IL-2 production." Immunology 73(3): 316-21.

Jinek, M., K. Chylinski, et al. (2012). "A programmable dual-RNA-guided DNA endonuclease in adaptive bacterial immunity." Science 337(6096): 816-21.

June, C. H. et al. (2011). "T Cells with Chimeric Antigen Receptors Have Potent Antitumor Effects and Can Establish Memory in Patients with Advanced Leukemia". Sci. Transl. Med. 3(95):ra73.

Kalish, J. M. and P. M. Glazer (2005). "Targeted genome modification via triple helix formation." Ann N Y Acad Sci 1058: 151-61.

Li, T., S. Huang, et al. (2011). "TAL nucleases (TALNs): hybrid proteins composed of TAL effectors and FokI DNA-cleavage domain." Nucleic Acids Res 39(1): 359-72.

Liu, J., M. W. Albers, et al. (1992). "Inhibition of T cell signaling by immunophilin-ligand complexes correlates with loss of calcineurin phosphatase activity." Biochemistry 31(16): 3896-901.

Lo, A. S. Y., Ma, Q., Liu, D. L., and Junghans, R. P. (2010). Anti-GD3 chimeric sFv-CD28/T-cell receptor zeta designer T cells for treatment of metastatic melanoma and other neuroectodermal tumors. Clin. Cancer Res. Off. J. Am. Assoc. Cancer Res. 16, 2769-2780.

Mali, P., L. Yang, et al. (2013). "RNA-guided human genome engineering via Cas9." Science 339(6121): 823-6.

Moscou, M. J. and A. J. Bogdanove (2009). "A simple cipher governs DNA recognition by TAL effectors." Science 326(5959): 1501.

Nakayama, J., Fukuda, M. N., Hirabayashi, Y., Kanamori, A., Sasaki, K., Nishi, T., Fukuda, M. (1996). "Expression cloning of a human GT3 synthase. GD3 and GT3 are synthesized by a single enzyme." J. Biol. Chem. 271: 3684-369.

Paques, F. and P. Duchateau (2007). "Meganucleases and DNA double-strand break-induced recombination: perspectives for gene therapy." Curr Gene Ther 7(1): 49-66.

Park, T. S., S. A. Rosenberg, et al. (2011). "Treating cancer with genetically engineered T cells." Trends Biotechnol 29(11): 550-7.

Peipp, M., D. Saul, et al. (2004). "Efficient eukaryotic expression of fluorescent scFv fusion proteins directed against CD antigens for FACS applications." J Immunol Methods 285(2): 265-80.

Perrin, A., M. Buckle, et al. (1993). "Asymmetrical recognition and activity of the I-SceI endonuclease on its site and on intron-exon junctions." Embo J 12(7): 2939-47.

Pingoud, A. and G. H. Silva (2007). "Precision genome surgery." Nat Biotechnol 25(7): 743-4.

Porteus, M. H. and D. Carroll (2005). "Gene targeting using zinc finger nucleases." Nat Biotechnol 23(8): 967-73.

Reaman, G. H., Taylor, B. J., and Merritt, W. D. (1990). Anti-GD3 monoclonal antibody analysis of childhood T-cell acute lymphoblastic leukemia: detection of a target antigen for antibody-mediated cytolysis. Cancer Res. 50, 202-205.

Rouet, P., F. Smih, et al. (1994). "Introduction of double-strand breaks into the genome of mouse cells by expression of a rare-cutting endonuclease." Mol Cell Biol 14(12): 8096-106.

Sorek, R., C. M. Lawrence, et al. (2013). "CRISPR-mediated Adaptive Immune Systems in Bacteria and Archaea." Annu Rev Biochem.

Yun, C. O., Nolan, K. F., Beecham, E. J., Reisfeld, R. A., and Junghans, R. P. (2000). Targeting of T lymphocytes to melanoma cells through chimeric anti-GD3 immunoglobulin T-cell receptors. Neoplasia New York N 2, 449-459.

---

The invention claimed is:

1. An anti-GD3 (NTRKR1) specific chimeric antigen receptor (CAR) comprising:
   (a) an extra cellular ligand binding-domain comprising a variable heavy chain comprising the CDR regions set forth in SEQ ID NO:42, SEQ ID NO:43, and SEQ ID NO:44, and a variable light chain comprising the CDR regions set forth in SEQ ID NO:45, SEQ ID NO:46, and SEQ ID NO:47,
   (b) a hinge comprising an amino acid sequence at least 95 percent identical to SEQ ID NO:4,
   (c) a transmembrane domain comprising the amino acid sequence set forth in SEQ ID NO:6, and
   (d) a cytoplasmic domain comprising (i) a signaling domain comprising an amino acid sequence at least 95 percent identical to SEQ ID NO:9 and (ii) a co-stimulatory domain comprising an amino acid sequence at least 95 percent identical to SEQ ID NO:8.

2. The anti-GD3 specific CAR according to claim 1, wherein said hinge comprises the amino acid sequence set forth in SEQ ID NO:4.

3. The anti-GD3 specific CAR according to claim 1, wherein said variable heavy chain comprises at least 95 percent identity to SEQ ID NO:13.

4. The anti-GD3 specific CAR according to claim 1, wherein said variable light chain comprises at least 95 percent identity to SEQ ID NO:14.

5. The anti-GD3 specific CAR according to claim 1, wherein said co-stimulatory domain comprises the amino acid sequence set forth in SEQ ID NO:8.

6. The anti-GD3 specific CAR according to claim 1, wherein said signaling domain comprises the amino acid sequence set forth in SEQ ID NO:9.

7. The anti-GD3 specific CAR according to claim 1 further comprising another extracellular ligand binding domain which is not specific for GD3.

8. The anti-GD3 specific CAR according to claim 1, wherein the CAR comprises a polypeptide sequence having at least 95 percent identity to SEQ ID NO:23.

9. The anti-GD3 specific CAR according to claim 1, wherein the CAR comprises the amino acid sequence set forth in SEQ ID NO:23.

10. The anti-GD3 specific CAR according to claim 1, further comprising a signal peptide.

11. The anti-GD3 specific CAR according to claim 1, wherein said variable heavy chain comprises the amino acid sequence set forth in SEQ ID NO:13.

12. The anti-GD3 specific CAR according to claim 1, wherein said variable light chain comprises the amino acid sequence set forth in SEQ ID NO:14.

* * * * *